(12) United States Patent
Regueiro-Ren et al.

(10) Patent No.: US 8,242,124 B2
(45) Date of Patent: Aug. 14, 2012

(54) DIKETOPIPERIDINE DERIVATIVES AS HIV ATTACHMENT INHIBITORS

(75) Inventors: Alicia Regueiro-Ren, Middletown, CT (US); Jacob Swidorski, Southington, CT (US); Zheng Liu, Beacon Falls, CT (US); Tao Wang, Farmington, CT (US); Zhongxing Zhang, Madison, CT (US); Lawrence G. Hamann, North Grafton, MA (US); Nicholas A. Meanwell, East Hampton, CT (US); David J. Carini, Wallingford, CT (US); Wenying Li, West Windsor, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 492 days.

(21) Appl. No.: 12/490,727

(22) Filed: Jun. 24, 2009

(65) Prior Publication Data
US 2009/0325985 A1 Dec. 31, 2009

Related U.S. Application Data

(60) Provisional application No. 61/075,376, filed on Jun. 25, 2008.

(51) Int. Cl.
*A61K 31/519* (2006.01)
*A61K 31/44* (2006.01)
*C07D 471/04* (2006.01)

(52) U.S. Cl. ............ 514/264.1; 514/300; 544/279; 546/113; 546/122

(58) Field of Classification Search .............. None
See application file for complete search history.

(56) References Cited

U.S. PATENT DOCUMENTS

| | | |
|---|---|---|
| 6,469,006 B1 | 10/2002 | Blair et al. |
| 6,476,034 B2 | 11/2002 | Wang et al. |
| 6,573,262 B2 | 6/2003 | Wallace et al. |
| 6,825,201 B2 | 11/2004 | Wang et al. |
| 6,900,206 B2 | 5/2005 | Kadow et al. |
| 6,900,323 B2 | 5/2005 | Wang et al. |
| 7,348,337 B2 | 3/2008 | Wang et al. |
| 7,354,924 B2 | 4/2008 | Wang et al. |
| 7,396,830 B2 | 7/2008 | Wang et al. |
| 7,449,476 B2 | 11/2008 | Ruediger et al. |
| 7,504,399 B2 | 3/2009 | Wang et al. |
| 2004/0063744 A1 | 4/2004 | Wang et al. |
| 2004/0063746 A1 | 4/2004 | Regueiro-Ren et al. |
| 2005/0209246 A1 | 9/2005 | Ueda et al. |
| 2005/0215543 A1 | 9/2005 | Lin et al. |
| 2005/0215544 A1 | 9/2005 | Lin et al. |
| 2005/0215545 A1 | 9/2005 | Lin et al. |
| 2005/0261296 A1 | 11/2005 | Yeung et al. |
| 2007/0155702 A1 | 7/2007 | Chen et al. |

FOREIGN PATENT DOCUMENTS

| | | |
|---|---|---|
| WO | WO 00/76521 | 12/2000 |
| WO | WO 02/062423 | 8/2002 |
| WO | WO 02/085301 | 10/2002 |
| WO | WO 03/068221 | 8/2003 |
| WO | WO 03/103607 | 12/2003 |
| WO | WO 2004/043375 | 5/2004 |
| WO | WO 2005/016344 | 2/2005 |
| WO | WO 2005/121094 | 12/2005 |
| WO | WO 2007/103456 | 9/2007 |
| WO | WO 2007/127635 | 11/2007 |

OTHER PUBLICATIONS

Chen et al., Quantitative structure-activity relationship studies on 1-aryl-tetrahydroisoquinoline analogs as active anti-HIV agents, 18 Bioorg. Med. Chem. Lett. 5381-5386 (2008).*

Blair, W.S. et al., "HIV-1 entry—an expanding portal for drug discovery", Drug Discovery Today, vol. 5, No. 5, pp. 183-194 (2000).

Dhar, T.G.M. et al., "Synthesis and SAR of p38α MAP kinase inhibitors based on heterobicyclic scaffolds", Bioorganic & Medicinal Chemistry Letters, vol. 17, pp. 5019-5024 (2007).

Hotoda, H., "Small-molecule inhibitors of HIV-1 entry via chemokine receptors", Drugs of the Future, vol. 24, No. 12, pp. 1355-1362 (1999).

Lu, R.-J. et al., "Design and Synthesis of Human Immunodeficiency Virus Entry Inhibitors: Sulfonamide as an Isotere for the α-Ketoamide Group", Journal of Medicinal Chemistry, vol. 50, No. 26, pp. 6535-6544 (2007).

Meanwell, N.A. et al., "Inhibitors of the entry of HIV into host cells", Current Opinion in Drug Discovery & Development, vol. 6, No. 4, pp. 451-461 (2003).

Sodroski, J.G., "HIV-1 Entry Inhibitors in the Side Pocket", Cell, vol. 99, pp. 243-246 (1999).

Wang, J. et al., "Modification and structure-activity relationship of a small molecule HIV-1 inhibitor targeting the viral envelope glycoprotein gp120", Org. Biomol. Chem., vol. 3, pp. 1781-1786 (2005).

* cited by examiner

*Primary Examiner* — Janet Andres
*Assistant Examiner* — Timothy R Rozof
(74) *Attorney, Agent, or Firm* — John F. Levis

(57) ABSTRACT

Compounds having drug and bio-affecting properties, their pharmaceutical compositions and methods of use are set forth. In particular, diketopiperidine derivatives that possess unique antiviral activity are provided. These compounds are useful for the treatment of HIV and AIDS.

15 Claims, No Drawings

DIKETOPIPERIDINE DERIVATIVES AS HIV ATTACHMENT INHIBITORS

CROSS-REFERENCE TO RELATED APPLICATION

This non-provisional application claims the benefit of U.S. Provisional Application Ser. No. 61/075,376 filed Jun. 25, 2008.

FIELD OF THE INVENTION

This invention provides compounds having drug and bio-affecting properties, their pharmaceutical compositions and methods of use. In particular, the disclosure is directed to diketopiperidine derivatives that possess unique antiviral activity. More particularly, the present disclosure relates to compounds useful for the treatment of HIV and AIDS.

BACKGROUND OF THE INVENTION

HIV-1 (human immunodeficiency virus-1) infection remains a major medical problem, with an estimated 45 million people infected worldwide at the end of 2007. The number of cases of HIV and AIDS (acquired immunodeficiency syndrome) has risen rapidly. In 2005, approximately 5.0 million new infections were reported, and 3.1 million people died from AIDS. Currently available drugs for the treatment of HIV include nucleoside reverse transcriptase (RT) inhibitors or approved single pill combinations: zidovudine (or AZT or RETROVIR®), didanosine (or VIDEX®), stavudine (or ZERIT®), lamivudine (or 3TC or EPIVIR®), zalcitabine (or DDC or HIVID®), abacavir succinate (or ZIAGEN®), tenofovir disoproxil fumarate salt (or VIREAD®), emtricitabine (or FTC-EMTRIVA®), COMBIVIR® (contains –3TC plus AZT), TRIZIVIR® (contains abacavir, lamivudine, and zidovudine), Epzicom (contains abacavir and lamivudine), TRUVADA® (contains VIREAD® and EMTRIVA®); non-nucleoside reverse transcriptase inhibitors: nevirapine (or VIRAMUNE®), delavirdine (or RESCRIPTOR®), etravirine, and efavirenz (or SUSTIVA®), Atripla (TRUVADA®+SUSTIVA®), and peptidomimetic protease inhibitors or approved formulations: saquinavir, indinavir, ritonavir, nelfinavir, amprenavir, lopinavir, KALETRA® (lopinavir and Ritonavir), atazanavir (REYATAZ®), darunavir and tipranavir, as well as the integrase inhibitor raltegravir, and the entry inhibitors enfuvirtide (FUZEON® or T-20) and maraviroc (Selzentry).

Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients may ultimately fail combination drug therapies. Insufficient drug potency, non-compliance, restricted tissue penetration and drug-specific limitations within certain cell types (e.g., most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when suboptimal drug concentrations are present. Therefore, novel anti-HIV agents exhibiting distinct resistance patterns, and favorable pharmacokinetic as well as safety profiles are needed to provide more treatment options. Improved HIV fusion inhibitors and HIV entry coreceptor antagonists are two examples of new classes of anti-HIV agents further being studied by a number of investigators.

HIV attachment inhibitors are a novel subclass of antiviral compounds that bind to the HIV surface glycoprotein gp120, and interfere with the interaction between the surface protein gp120 and the host cell receptor CD4. Thus, they prevent HIV from attaching to the human CD4 T-cell, and block HIV replication in the first stage of the HIV life cycle. The properties of HIV attachment inhibitors have been improved in an effort to obtain compounds with maximized utility and efficacy as antiviral agents. A disclosure describing indoles of which the structure shown below for BMS-705 is representative, has been disclosed (Antiviral Indoleoxoacetyl Piperazine Derivatives).

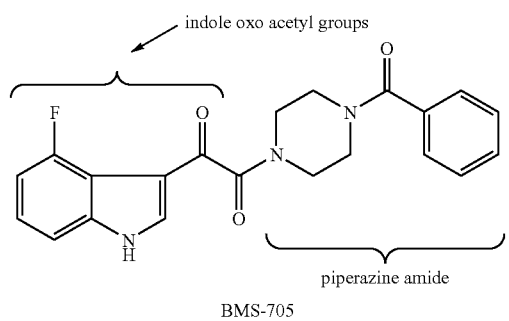

BMS-705

Two other compounds, referred to in the literature as BMS-806 and BMS-043 have been described in both the academic and patent art:

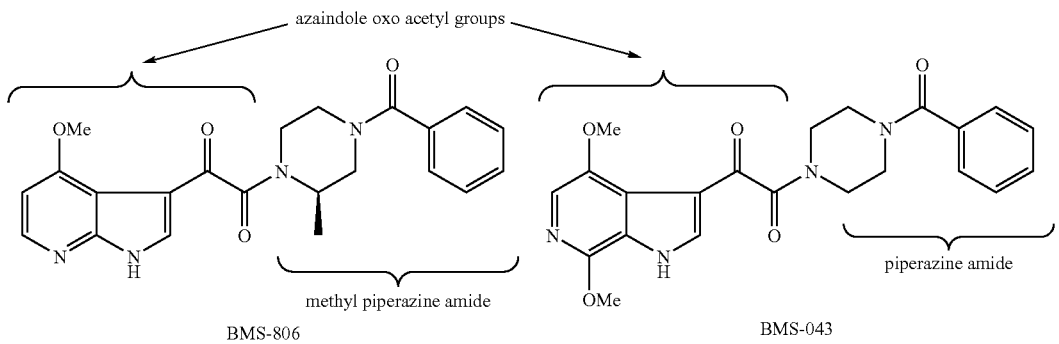

BMS-806

BMS-043

Some description of their properties in human clinical trials has been disclosed in the literature.

It should be noted that in all three of these structures, a piperazine amide (in these three structures a piperazine phenyl amide) is present and this group is directly attached to an oxoacetyl moiety. The oxoacetyl group is attached at the 3-position of 4-fluoro indole in BMS-705 and to the 3 position of substituted azaindoles in BMS-806 and BMS-043.

In an effort to obtain improved anti-HIV compounds, later publications described in part, modified substitution patterns on the indoles and azaindoles. Examples of such efforts include: (1) novel substituted indoleoxoacetic piperazine derivatives, (2) substituted piperazinyloxoacetylindole derivatives, and (3) substituted azaindoleoxoacetic piperazine derivatives.

Replacement of these groups with other heteroaromatics or substituted heteroaromatics or bicyclic hydrocarbons was also shown to be feasible. Examples include: (1) indole, azaindole and related heterocyclic amidopiperazine derivatives; (2) bicyclo 4.4.0 antiviral derivatives; and (3) diazaindole derivatives.

A select few replacements for the piperazine amide portion of the molecules have also been described in the art and among these examples are (1) some piperidine alkenes; (2) some pyrrolidine amides; (3) some N-aryl or heteroaryl piperazines; (4) some piperazinyl ureas; and (5) some carboline containing compounds.

Method(s) for preparing prodrugs for this class of compounds are disclosed in Prodrugs of Piperazine and Substituted Piperidine Antiviral Agents (Ueda et al., U.S. non-provisional application Ser. No. 11/066,745, filed Feb. 25, 2005 or U.S. Publication No. 2005/0209246 A1 or WO 2005/090367 A1).

A published PCT patent application WO2003103607A1 (Jun. 11, 2003) disclosures an assay useful for assaying some HIV inhibitors.

Several published patent applications describe combination studies with piperazine benzamide inhibitors, for example, U.S. Publication No. 2005/0215543 (WO 2005/102328 A1), U.S. Publication No. 2005/0215544 (WO 2005/102391 A1), and U.S. Publication No. 2005/0215545 (WO 2005/102392 A2).

A publication on new compounds in this class of attachment inhibitors (Wang, J. et al., *Org. Biol. Chem.*, 3:1781-1786 (2005).) and a patent application on some more remotely related compounds have appeared WO 2005/016344 published on Feb. 24, 2005.

Published patent applications WO 2005/016344 and WO 2005/121094 also describe piperazine derivatives which are HIV inhibitors. Other references in the HIV attachment area include U.S. Publication Nos. 2007/0155702, 2007/0078141 and 2007/0287712, WO 2007/103456, as well as U.S. Pat. Nos. 7,348,337 and 7,354,924. A literature reference is *J. Med. Chem.*, 50:6535 (2007).

What is therefore needed in the art are new HIV attachment inhibitor compounds, and compositions thereof, which are efficacious against HIV infection. The compounds described in the foregoing references are structurally distinct from the compounds of the present invention hereinafter described.

SUMMARY OF THE INVENTION

The present invention provides compounds of Formula I below, the pharmaceutically acceptable salts and/or solvates (e.g. hydrates) thereof, their pharmaceutical formulations, and their use in patients suffering from or susceptible to a virus such as HIV. The compounds of Formula I, their pharmaceutically acceptable salts and/or solvates are effective antiviral agents, particularly as inhibitors of HIV. They are useful for the treatment of HIV and AIDS.

One embodiment of the present invention is directed to a compound of Formula I, including pharmaceutically acceptable salts thereof:

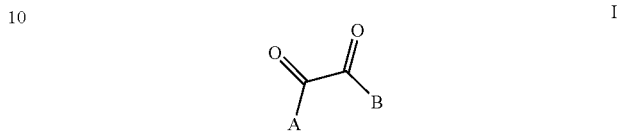

wherein A is selected from the group consisting of:

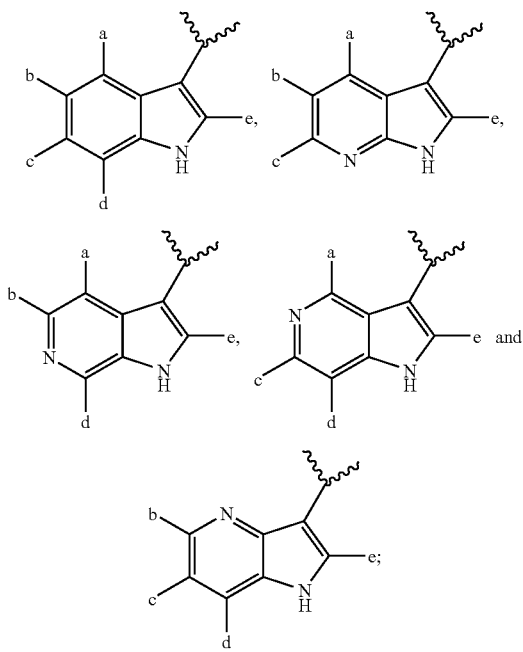

wherein B is selected from the group consisting of:

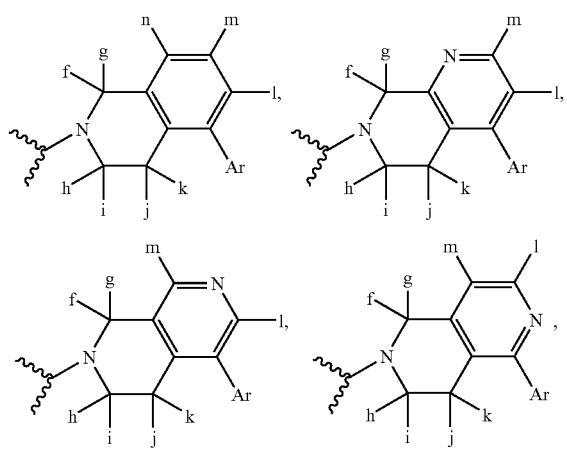

-continued

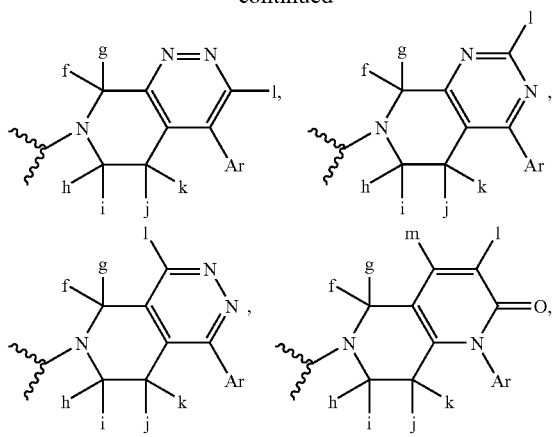

and further wherein a is selected from the group consisting of H, halogen and methoxy;

b and c are selected from the group consisting of H and halogen;

d is selected from the group consisting of H, halogen, methoxy and Group C;

e is H;

f and g are selected from the group consisting of H, ($C_1$-$C_4$)alkyl, and ($C_3$-$C_6$)cycloalkyl group, and wherein said alkyl or cycloalkyl group is optionally substituted with one to three substitutions selected from the group of F, OH, OR, $NR_1R_2$, COOR, and $CONR_1R_2$;

and wherein f and g can be connected by carbon, oxygen, nitrogen or sulfur atom to form a ring;

h and i are selected from the group consisting of H, ($C_1$-$C_4$)alkyl, and ($C_3$-$C_6$)cycloalkyl group wherein said alkyl or cycloalkyl group is optionally substituted with one to three substitutions selected from the group of F, OH, OR, $NR_1R_2$, COOR, and $CONR_1R_2$;

and wherein h and i can be connected by a carbon, oxygen, nitrogen or sulfur atom to form a ring;

j and k are selected from the group consisting of H, F, ($C_1$-$C_4$)alkyl, and ($C_3$-$C_6$)cycloalkyl group, and wherein said alkyl or cycloalkyl group is optionally substituted with one to three substitutions selected from the group of F, OH, OR, $NR_1R_2$, COOR, and $CONR_1R_2$;

and wherein j and k can be connected by carbon, oxygen, nitrogen or sulfur atom to form a ring;

and further wherein j+k is =O attached to the ring;

l, m and n are selected from the group consisting of H, OH, CN, ($C_1$-$C_4$)alkyl optionally substituted with one to three substitutions selected from F, OH, OR, $NR_1R_2$, COOR, $CONR_1R_2$, ($C_3$-$C_6$)cycloalkyl optionally substituted with one to three substitutions selected from F, OH, OR, $NR_1R_2$, COOR, $CONR_1R_2$, OR, halogen (attached to carbon only), $NR_1R_2$, COOR, $CONR_1R_2$, and Group D;

Ar is selected from the group consisting of phenyl and heteroaryl; wherein said phenyl and heteroaryl are independently optionally substituted with one to three same or different halogens or from one to three same or different substituents selected from Group E; heteroaryl is selected from the group consisting of pyridinyl, pyrazinyl, pyridazinyl, pyrimidinyl, furanyl, thienyl, thiazolyl, imidazolyl, oxadiazolyl, thiadiazolyl, pyrazolyl, tetrazolyl, and triazolyl;

Group C is selected from the group consisting of COOR, $CONR_1R_2$, and Group D;

Group D is selected from the group consisting of phenyl and heteroaryl; wherein said phenyl and heteroaryl are independently optionally substituted with one to three same or different halogens or from one to three same or different substituents selected from Group E; heteroaryl is selected from the group consisting of pyridinyl, pyrazinyl, pyridazinyl, pyrimidinyl, furanyl, thienyl, thiazolyl, imidazolyl, oxadiazolyl, thiadiazolyl, pyrazolyl, tetrazolyl, and triazolyl;

Group E is selected from the group consisting of OH, OR, CN, COOR, $CONR_1R_2$, ($C_1$-$C_4$)alkyl, ($C_3$-$C_6$)cycloalkyl, and wherein said alkyl or cycloalkyl group is optionally substituted with one to three substitutions selected from the group of F, OH, OR, $NR_1R_2$, COOR, and $CONR_1R_2$;

R, $R_1$ and $R_2$ are independently H, ($C_1$-$C_4$)alkyl, ($C_3$-$C_6$) cycloalkyl group; and wherein $R_1$ and $R_2$ can be connected by carbon, oxygen, nitrogen or sulfur atom to form a ring.

Another embodiment of the present invention is directed to a method for treating mammals infected with a virus, especially wherein said virus is HIV, comprising administering to said mammal an antiviral effective amount of a compound of Formula I above, and one or more pharmaceutically acceptable carriers, excipients or diluents. Optionally, the compound of Formula I can be administered in combination with an antiviral effective amount of an AIDS treatment agent selected from the group consisting of: (a) an AIDS antiviral agent; (b) an anti-infective agent; (c) an immunomodulator; and (d) other HIV entry inhibitors.

Another embodiment of the present invention is a pharmaceutical composition comprising an antiviral effective amount of a compound of Formula I and one or more pharmaceutically acceptable carriers, excipients, diluents and optionally in combination with an antiviral effective amount of an AIDS treatment agent selected from the group consisting of: (a) an AIDS antiviral agent; (b) an anti-infective agent; (c) an immunomodulator; and (d) other HIV entry inhibitors.

In another embodiment of the invention there is provided one or more methods for making the compounds of Formula I.

The present invention is directed to these, as well as other important ends, hereinafter described.

DETAILED DESCRIPTION OF THE EMBODIMENTS

Since the compounds of the present disclosure may possess asymmetric centers and therefore occur as mixtures of diastereomers and enantiomers, the present disclosure includes the individual diastereoisomeric and enantiomeric forms of the compounds of Formula I in addition to the mixtures thereof.

Definitions

Unless otherwise specifically set forth elsewhere in the application, one or more of the following terms may be used herein, and shall have the following meanings:

The term "$C_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"$C_1$-$C_4$ fluoroalkyl" refers to F-substituted $C_1$-$C_4$ alkyl wherein at least one H atom is substituted with F atom, and each H atom can be independently substituted by F atom;

"Halogen" refers to chlorine, bromine, iodine or fluorine.

An "aryl" or "Ar" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —NR$^x$R$^y$, wherein R$^x$ and R$^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl, diazinyl, pyrazine, triazinyl, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thioalkoxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and –NR$^x$R$^y$, wherein R$^x$ and R$^y$ are as defined above.

As used herein, a "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encompass systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —NR$^x$R$^y$, wherein R$^x$ and R$^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexene, cycloheptane, cycloheptene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —NR$^x$R$^y$ with R$^x$ and R$^y$ as defined above.

An "alkenyl" group refers to an alkyl group, as defined herein, having at least two carbon atoms and at least one carbon-carbon double bond.

An "alkynyl" group refers to an alkyl group, as defined herein, having at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroalicyclic group.

A "trihalomethanecarbonyl" group refers to a $Z_3CC(=O)$— group with said Z being a halogen.

A "C-carboxy" group refers to a —C(=O)O—R" groups, with R" as defined herein.

An "O-carboxy" group refers to a R"C(=O)O-group, with R" as defined herein.

A "carboxylic acid" group refers to a C-carboxy group in which R" is hydrogen.

A "trihalomethyl" group refers to a —$CZ_3$ group wherein Z is a halogen group as defined herein.

A "trihalomethanesulfonyl" group refers to an $Z_3CS(=O)_2$— groups with Z as defined above.

A "trihalomethanesulfonamido" group refers to a $Z_3CS(=O)_2NR^x$— group with Z as defined above and $R^x$ being H or $(C_{1-6})$alkyl.

A "sulfinyl" group refers to a —S(=O)—R" group, with R" being $(C_{1-6})$alkyl.

A "sulfonyl" group refers to a —$S(=O)_2R"$ group with R" being $(C_{1-6})$alkyl.

A "S-sulfonamido" group refers to a —$S(=O)_2NR^XR^Y$, with $R^X$ and $R^Y$ independently being H or $(C_{1-6})$alkyl.

A "N-Sulfonamido" group refers to a $R"S(=O)_2NR_X$— group, with $R_x$ being H or $(C_{1-6})$alkyl.

A "O-carbamyl" group refers to a —$OC(=O)NR^xR^y$ group, with $R^X$ and $R^Y$ independently being H or $(C_{1-6})$alkyl.

A "N-carbamyl" group refers to a $R^xOC(=O)NR^y$ group, with $R^x$ and $R^y$ independently being H or $(C_{1-6})$alkyl.

A "O-thiocarbamyl" group refers to a —$OC(=S)NR^xR^y$ group, with $R^x$ and $R^y$ independently being H or $(C_{1-6})$alkyl.

A "N-thiocarbamyl" group refers to a $R^xOC(=S)NR^y$— group, with $R^x$ and $R^y$ independently being H or $(C_{1-6})$alkyl.

An "amino" group refers to an —$NH_2$ group.

A "C-amido" group refers to a —$C(=O)NR^xR^y$ group, with $R^x$ and $R^y$ independently being H or $(C_{1-6})$alkyl.

A "C-thioamido" group refers to a —$C(=S)NR^xR^y$ group, with $R^x$ and $R^y$ independently being H or $(C_{1-6})$alkyl.

A "N-amido" group refers to a $R^xC(=O)NR^y$— group, with $R^x$ and $R^y$ independently being H or $(C_{1-6})$alkyl.

An "ureido" group refers to a —$NR^xC(=O)NR^yR^{y2}$ group, with $R^x$, $R^y$, and $R^{y2}$ independently being H or $(C_{1-6})$alkyl.

A "guanidino" group refers to a —$R^xNC(=N)NR^yR^{y2}$ group, with $R^x$, $R^y$, and $R^{y2}$ independently being H or $(C_{1-6})$alkyl.

A "guanyl" group refers to a $R^xR^yNC(=N)$— group, with $R^x$ and $R^y$ independently being H or $(C_{1-6})$alkyl.

A "cyano" group refers to a —CN group.

A "silyl" group refers to a —$Si(R")_3$, with R" being $(C_{1-6})$ alkyl or phenyl.

A "phosphonyl" group refers to a $P(=O)(OR^x)_2$ with $R^x$ being $(C_{1-6})$alkyl.

A "hydrazino" group refers to a —$NR^xNR^yR^{y2}$ group, with $R^x$, $R^y$, and $R^{y2}$ independently being H or $(C_{1-6})$alkyl.

A "4, 5, or 6 membered ring cyclic N-lactam" group refers to

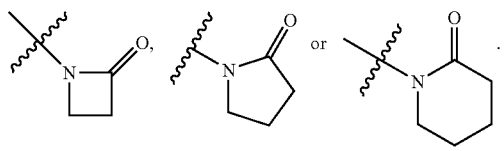

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present disclosure are based on the known general principles of chemical bonding. It is understood that the claims do not encompass structures known to be unstable or not able to exist based on the literature.

Pharmaceutically acceptable salts and prodrugs of compounds disclosed herein are within the scope of this disclosure. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g., hydroxyl-substituted alkylamines such as diethanolamine, triethanolamine or tris (hydroxymethyl)-aminomethane), or with bases such as piperidine or morpholine.

As stated above, the compounds of the invention also include "prodrugs". The term "prodrug" as used herein encompasses both the term "prodrug esters" and the term "prodrug ethers". The term "prodrug esters" as employed herein includes esters and carbonates formed by reacting one or more hydroxyls of compounds of Formula I with either alkyl, alkoxy, or aryl substituted acylating agents or phosphorylating agent employing procedures known to those skilled in the art to generate acetates, pivalates, methylcarbonates, benzoates, amino acid esters, phosphates, half acid esters such as malonates, succinates or glutarates, and the like. In certain embodiments, amino acid esters may be especially preferred.

Examples of such prodrug esters include

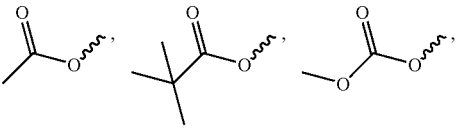

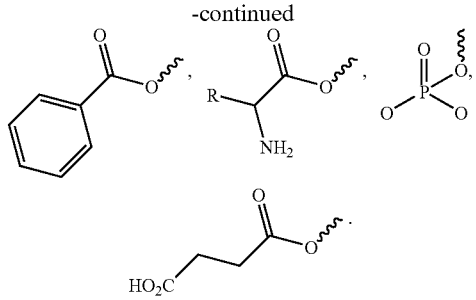

The term "prodrug ethers" include both phosphate acetals and O-glucosides. Representative examples of such prodrug ethers include

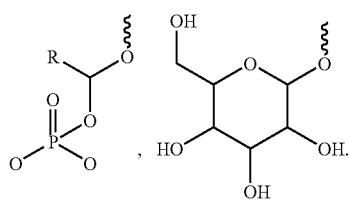

As set forth above, the invention is directed to compounds of Formula I, including pharmaceutically acceptable salts thereof:

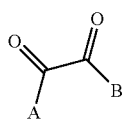

I wherein A is selected from the group consisting of:

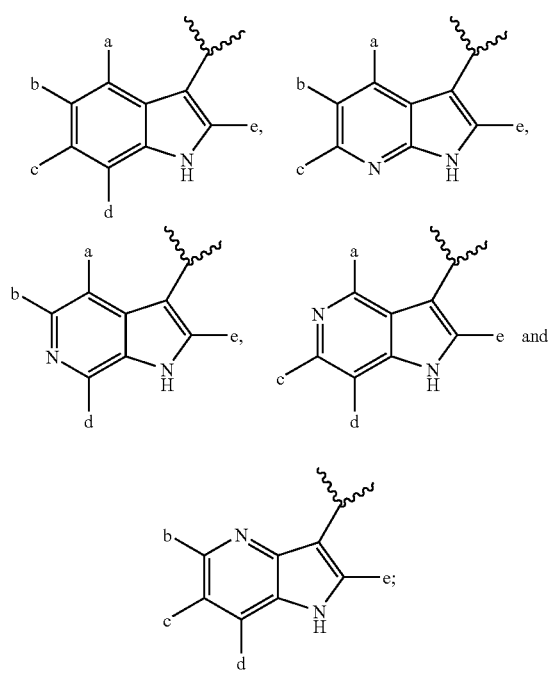

wherein B is selected from the group consisting of:

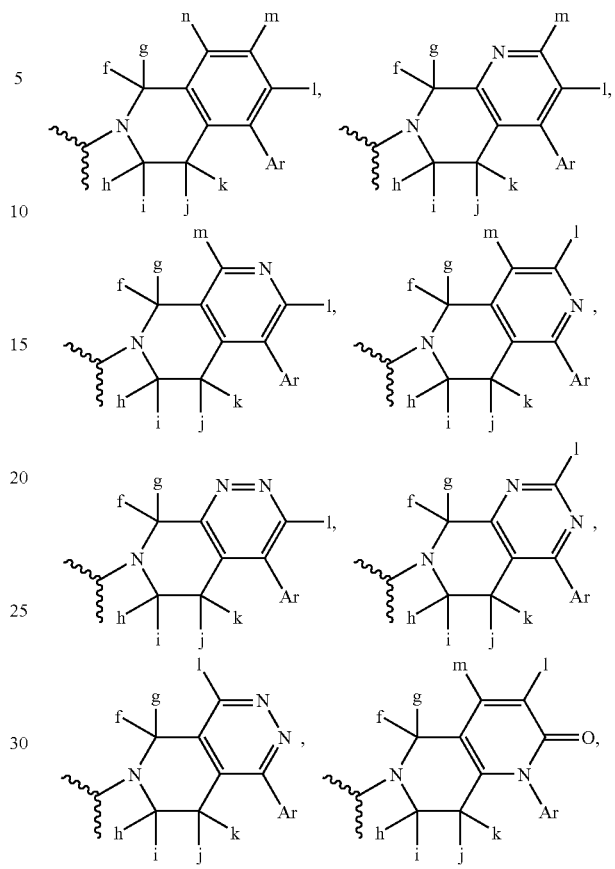

and further wherein
a is selected from the group consisting of H, halogen and methoxy;
b and c are selected from the group consisting of H and halogen;
d is selected from the group consisting of H, halogen, methoxy and Group C;
e is H;
f and g are selected from the group consisting of H, ($C_1$-$C_4$)alkyl, and ($C_3$-$C_6$)cycloalkyl group, and wherein said alkyl or cycloalkyl group is optionally substituted with one to three substitutions selected from the group of F, OH, OR, $NR_1R_2$, COOR, and $CONR_1R_2$;
and wherein f and g can be connected by carbon, oxygen, nitrogen or sulfur atom to form a ring;
h and i are selected from the group consisting of H, ($C_1$-$C_4$)alkyl, and ($C_3$-$C_6$)cycloalkyl group wherein said alkyl or cycloalkyl group is optionally substituted with one to three substitutions selected from the group of F, OH, OR, $NR_1R_2$, COOR, and $CONR_1R_2$;
and wherein h and i can be connected by a carbon, oxygen, nitrogen or sulfur atom to form a ring;
j and k are selected from the group consisting of H, F, ($C_1$-$C_4$)alkyl, and ($C_3$-$C_6$)cycloalkyl group, and wherein said alkyl or cycloalkyl group is optionally substituted with one to three substitutions selected from the group of F, OH, OR, $NR_1R_2$, COOR, and $CONR_1R_2$;
and wherein j and k can be connected by carbon, oxygen, nitrogen or sulfur atom to form a ring;
and further wherein j+k is =O attached to the ring;
l, m and n are selected from the group consisting of H, OH, CN, ($C_1$-$C_4$)alkyl optionally substituted with one to three substitutions selected from F, OH, OR, $NR_1R_2$, COOR, CONR$_1$R$_2$, (C$_3$-C$_6$)cycloalkyl optionally substituted with one to three substitutions selected from F, OH, OR, NR$_1$R$_2$, COOR, CONR$_1$R$_2$, OR, halogen (attached to carbon only), NR$_1$R$_2$, COOR, CONR$_1$R$_2$, and Group D;

Ar is selected from the group consisting of phenyl and heteroaryl; wherein said phenyl and heteroaryl are independently optionally substituted with one to three same or different halogens or from one to three same or different substituents selected from Group E; heteroaryl is selected from the group consisting of pyridinyl, pyrazinyl, pyridazinyl, pyrimidinyl, furanyl, thienyl, thiazolyl, imidazolyl, oxadiazolyl, thiadiazolyl, pyrazolyl, tetrazolyl, and triazolyl;

Group C is selected from the group consisting of COOR, CONR$_1$R$_2$, and Group D;

Group D is selected from the group consisting of phenyl and heteroaryl; wherein said phenyl and heteroaryl are independently optionally substituted with one to three same or different halogens or from one to three same or different substituents selected from Group E; heteroaryl is selected from the group consisting of pyridinyl, pyrazinyl, pyridazinyl, pyrimidinyl, furanyl, thienyl, thiazolyl, imidazolyl, oxadiazolyl, thiadiazolyl, pyrazolyl, tetrazolyl, and triazolyl;

Group E is selected from the group consisting of OH, OR, CN, COOR, CONR$_1$R$_2$, (C$_1$-C$_4$)alkyl, (C$_3$-C$_6$)cycloalkyl, and wherein said alkyl or cycloalkyl group is optionally substituted with one to three substitutions selected from the group of F, OH, OR, NR$_1$R$_2$, COOR, and CONR$_1$R$_2$;

R, R$_1$ and R$_2$ are independently H, (C$_1$-C$_4$)alkyl, (C$_3$-C$_6$) cycloalkyl group; and wherein R$_1$ and R$_2$ can be connected by carbon, oxygen, nitrogen or sulfur atom to form a ring.

More preferred compounds of the Formula I include those wherein A=

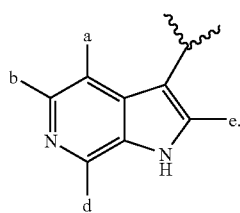

Also preferred compounds of the Formula I include those wherein B is selected from the group consisting of:

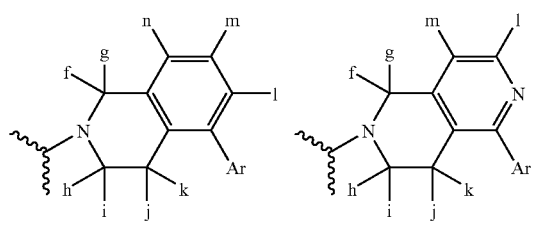

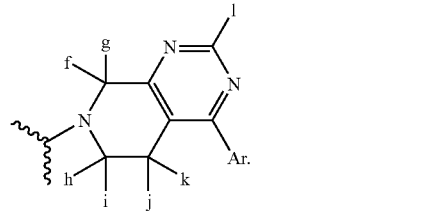

In another embodiment, both the preferred forms of A and B in the compound of Formula I are as set forth above.

Particularly preferred compounds of the invention as part of Formula I include the following:

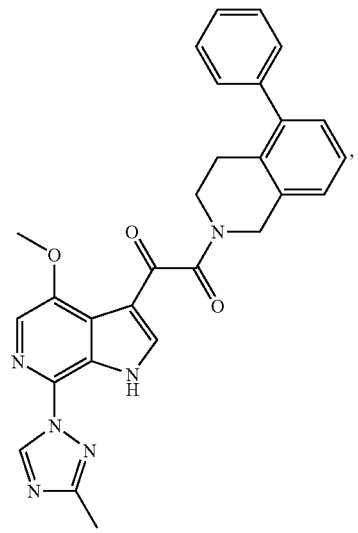

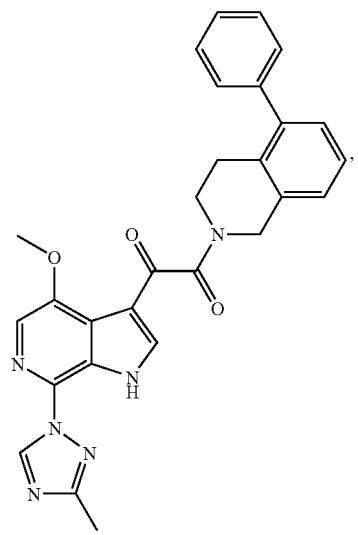

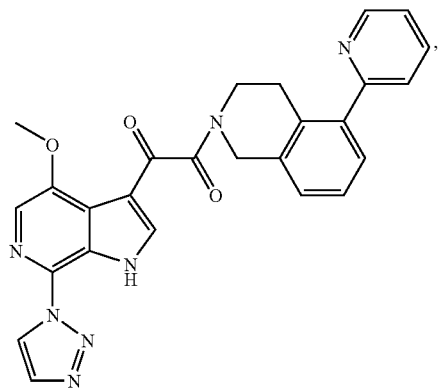

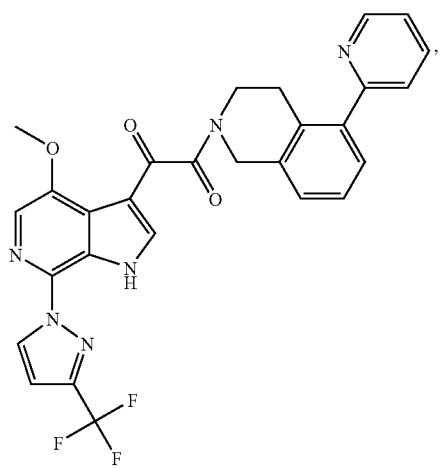
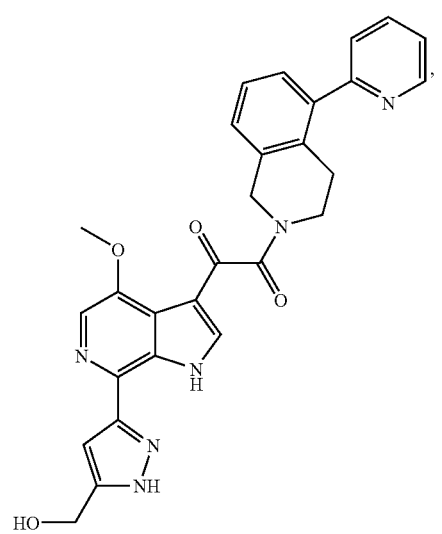
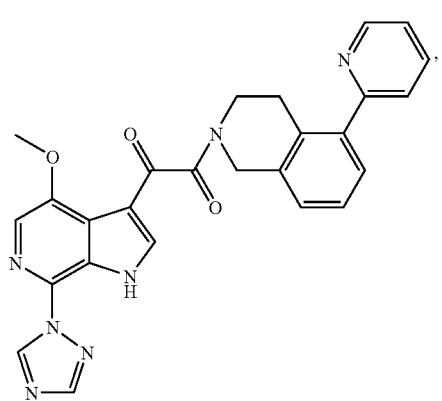
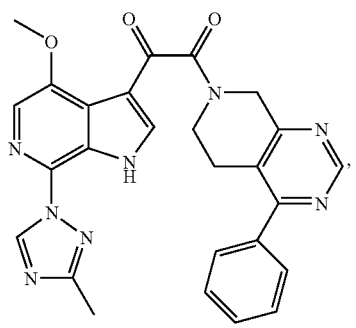
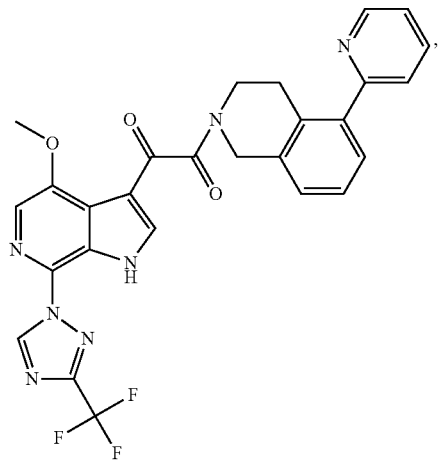
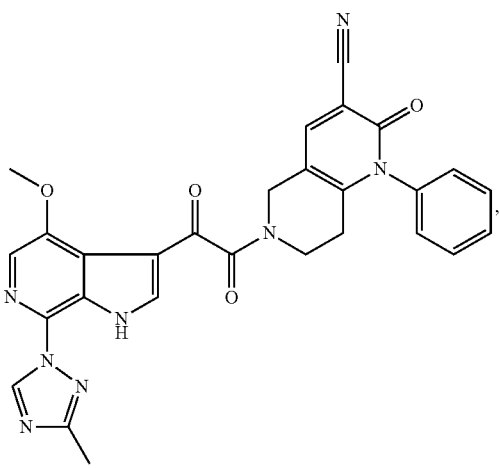

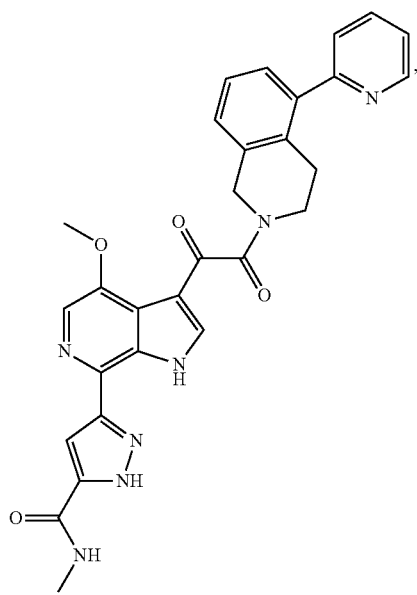
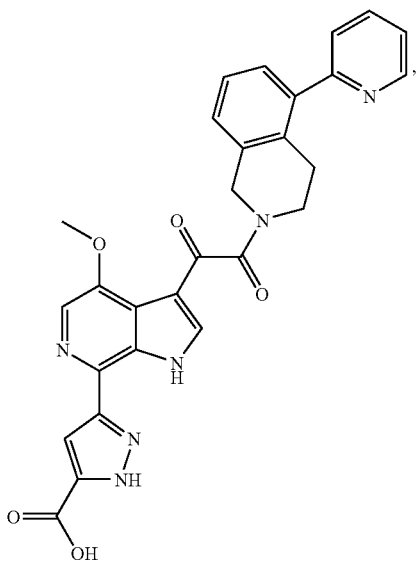

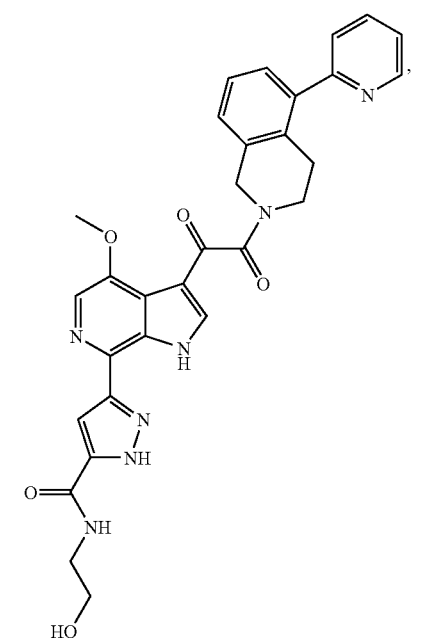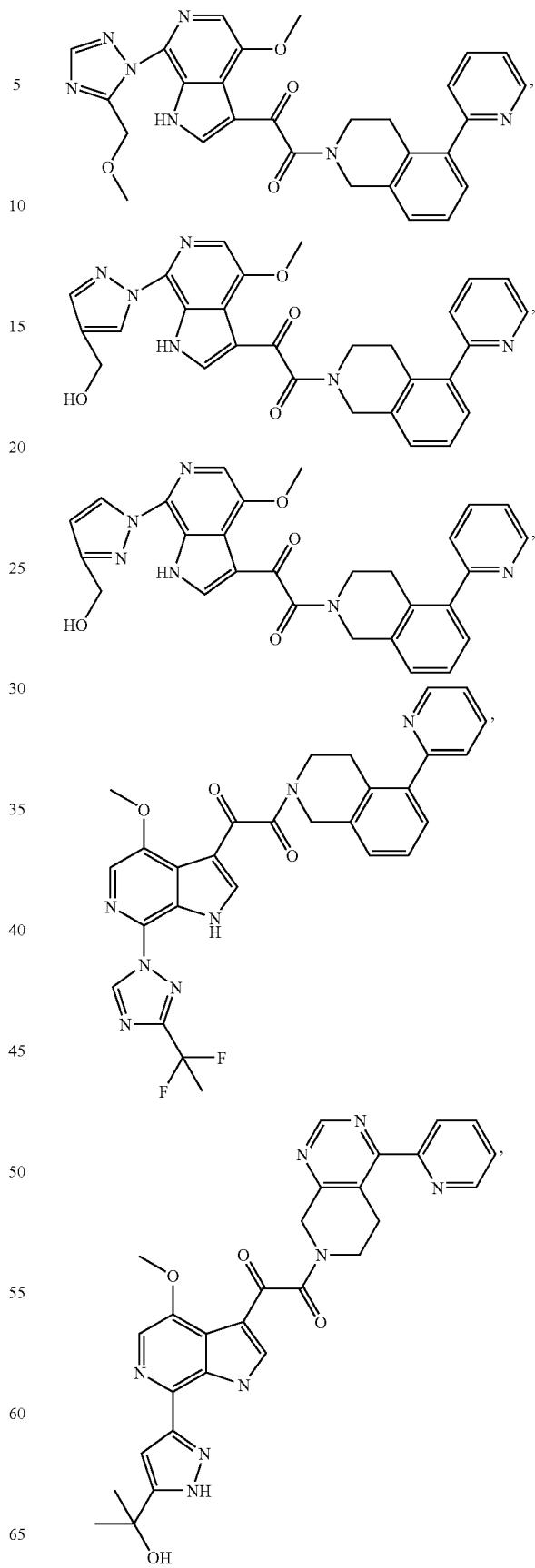

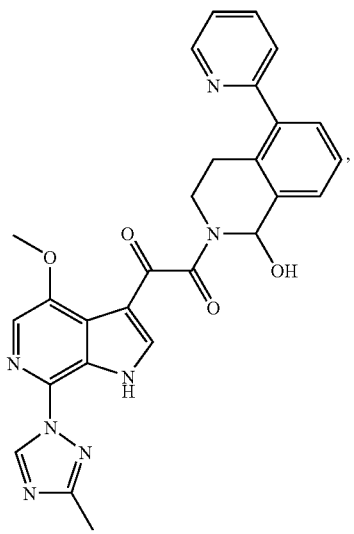

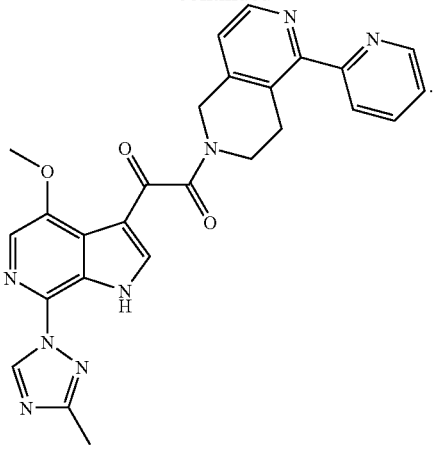

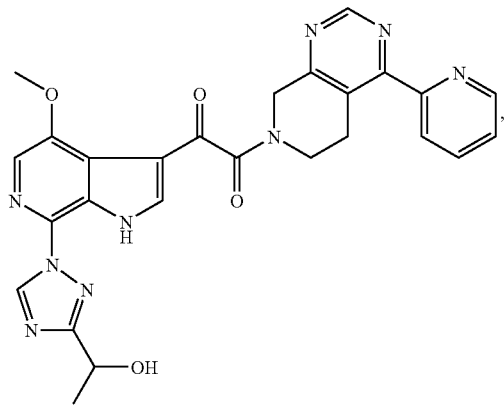

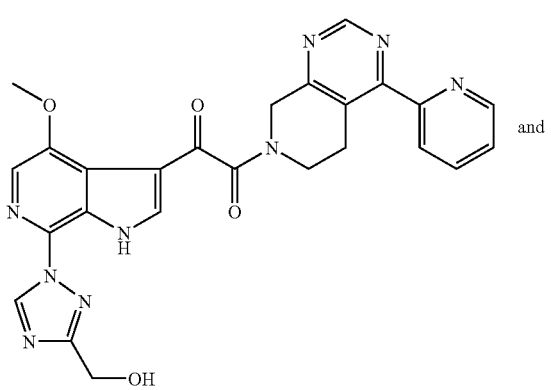

and

The compounds of the present invention, according to all the various embodiments described above, may be administered orally, parenterally (including subcutaneous injections, intravenous, intramuscular, intrasternal injection or infusion techniques), by inhalation spray, or rectally, and by other means, in dosage unit formulations containing non-toxic pharmaceutically acceptable carriers, excipients and diluents available to the skilled artisan. One or more adjuvants may also be included.

Thus, in accordance with the present disclosure, there is further provided a method of treatment, and a pharmaceutical composition, for treating viral infections such as HIV infection and AIDS. The treatment involves administering to a patient in need of such treatment a pharmaceutical composition which contains an antiviral effective amount of one or more of the compounds of Formula I, together with one or more pharmaceutically acceptable carriers, excipients or diluents. As used herein, the term "antiviral effective amount" means the total amount of each active component of the composition and method that is sufficient to show a meaningful patient benefit, i.e., inhibiting, ameliorating, or healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing, ameliorating or healing diseases associated with HIV infection.

The pharmaceutical compositions of the invention may be in the form of orally administrable suspensions or tablets; as well as nasal sprays, sterile injectable preparations, for example, as sterile injectable aqueous or oleaginous suspensions or suppositories. Pharmaceutically acceptable carriers, excipients or diluents may be utilized in the pharmaceutical compositions, and are those utilized in the art of pharmaceutical preparations.

When administered orally as a suspension, these compositions are prepared according to techniques typically known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds of this disclosure can be administered orally to humans in a dosage range of 1 to 100 mg/kg body weight in divided doses, usually over an extended period such as days, weeks, months or even years. One preferred dosage range is 1 to 10 mg/kg body weight orally in divided doses. Another preferred dosage range is 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also contemplated herein are combinations of the compounds of Formula I herein set forth, together with one or more agents useful in the treatment of AIDS. For example, the compounds of this disclosure may be effectively administered, whether at periods of pre-exposure and/or post-exposure, in combination with effective amounts of the AIDS antivirals, immunomodulators, anti-infectives, or vaccines, such as those in the following non-limiting table:

| ANTIVIRALS | | |
|---|---|---|
| Drug Name | Manufacturer | Indication |
| 097 | Hoechst/Bayer | HIV infection, AIDS, ARC (non-nucleoside reverse transcriptase (RT) inhibitor) |
| Amprenavir 141 W94 GW 141 | GlaxoWellcome | HIV infection, AIDS, ARC (protease inhibitor) |
| Abacavir (1592U89) GW 1592 | GlaxoWellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences Ethigen | HIV infection, ARC, PGL, |
| AL-721 | (Los Angeles, CA) | HIV positive, AIDS |
| Alpha Interferon | GlaxoWellcome | Kaposi's sarcoma, HIV in combination with RETROVIR ® |
| Ansamycin LM 427 | Adria Laboratories (Dublin, OH) Erbamont (Stamford, CT) | ARC |
| Antibody which neutralizes pH labile alpha aberrant interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | Sight threatening CMV peripheral CMV retinitis |
| Darunavir (Prezista) | Tibotec - J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI | Bristol-Myers Squibb | HIV infection, AIDS, |

ANTIVIRALS

| Drug Name | Manufacturer | Indication |
|---|---|---|
| Dideoxyinosine | | ARC; combination with AZT/d4T |
| DMP-450 | AVID (Camden, NJ) | HIV infection, AIDS, ARC (protease inhibitor) |
| Efavirenz (DMP 266, SUSTIVA ®) (−)6-Chloro-4-(S)-cyclopropylethynyl-4(S)-trifluoro-methyl-1,4-dihydro-2H-3,1-benzoxazin-2-one, Stocrin | Bristol Myers Squibb | HIV infection, AIDS, ARC (non-nucleoside RT inhibitor) |
| EL10 | Elan Corp, PLC (Gainesville, GA) | HIV infection |
| Etravirine | Tibotec - J & J | HIV infection, AIDS, ARC (non-nucleoside reverse transcriptase inhibitor) |
| Famciclovir | SmithKline | Herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | GlaxoWellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | GlaxoWellcome | Genital HSV and CMV infections |
| VIRAZOLE ® (Ribavirin) | Viratek/ICN (Costa Mesa, CA) | Asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |

-continued

ANTIVIRALS

| Drug Name | Manufacturer | Indication |
|---|---|---|
| Zidovudine; AZT | GlaxoWellcome | HIV infection, AIDS, ARC, Kaposi's sarcoma, in combination with other therapies |
| Tenofovir disoproxil, fumarate salt (VIREAD ®) | Gilead | HIV infection, AIDS, (reverse transcriptase inhibitor) |
| EMTRIVA ® (Emtricitabine) FTC | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| REYATAZ ® (or atazanavir) | Bristol-Myers Squibb | HIV infection, AIDS, protease inhibitor |
| FUZEON ® (enfuvirtide or T-20) | Roche/Trimeris | HIV infection, AIDS, viral fusion inhibitor |
| LEXIVA ® (or Fosamprenavir calcium) | GSK/Vertex | HIV infection, AIDS, viral protease inhibitor |
| Selzentry (maraviroc) (UK 427857) | Pfizer | HIV infection, AIDS, (CCR5 antagonist, in development) |
| TRIZIVIR ® | GSK | HIV infection, AIDS, (three drug combination) |
| Bevirimat | Panacos | HIV infection, AIDS, (maturation inhibitor, in development) |
| Sch-417690 (vicriviroc) | Schering-Plough | HIV infection, AIDS, (CCR5 antagonist, in development) |
| TAK-652 | Takeda | HIV infection, AIDS, (CCR5 antagonist, in development) |
| GSK 873140 (ONO-4128) | GSK/ONO | HIV infection, AIDS, (CCR5 antagonist, in development) |
| Integrase Inhibitor MK-0518 Raltegravir | Merck | HIV infection, AIDS |
| TRUVADA ® | Gilead | Combination of Tenofovir disoproxil fumarate salt (VIREAD ®) and EMTRIVA ® (Emtricitabine) |
| Integrase Inhibitor GS917/JTK-303 Elvitegravir | Gilead/Japan Tobacco | HIV infection, AIDS, viral integrase inhibitor in development |
| Triple drug combination Atripla | Gilead/Bristol-Myers Squibb | Combination of Tenofovir disoproxil fumarate salt (VIREAD ®), EMTRIVA ® (Emtricitabine), and SUSTIVA ®(Efavirenz) |

IMMUNOMODULATORS

| Drug Name | Manufacturer | Indication |
|---|---|---|
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination with TNF (tumor necrosis factor) |

IMMUNOMODULATORS

| Drug Name | Manufacturer | Indication |
|---|---|---|
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, in combination with AZT |
| HIV Core Particle Immunostimulant | Rorer | Seropositive HIV |
| IL-2 Interleukin-2 | Cetus | AIDS, in combination with AZT |
| IL-2 Interleukin-2 | Hoffman-LaRoche Immunex | AIDS, ARC, HIV, in combination with AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination with AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering-Plough | Kaposi's sarcoma with AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination with AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma, AIDS, ARC, in combination with AZT |
| SK&F106528 Soluble T4 | SmithKline | HIV infection |
| Thymopentin | Immunobiology Research Institute (Annandale, NJ) | HIV infection |
| Tumor Necrosis Factor; TNF | Genentech | ARC, in combination with gamma interferon |

ANTI-INFECTIVES

| Drug Name | Manufacturer | Indication |
|---|---|---|
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin Intraconazole-R51211 | Rhone-Poulenc Janssen Pharm. | Cryptosporidial diarrhea Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia associated with AZT therapy |
| Recombinant Human Growth Hormone | Serono | AIDS-related wasting, cachexia |
| Megestrol Acetate | Bristol-Myers Squibb | Treatment of anorexia associated with AIDS |
| Testosterone | ALZA ®, SmithKline | AIDS-related wasting |
| Total Enteral Nutrition | Norwich Eaton Pharmaceuticals | Diarrhea and malabsorption related to AIDS |

Additionally, the compounds of the disclosure herein set forth may be used in combination with other HIV entry inhibitors. Examples of such HIV entry inhibitors are discussed in *Drugs of the Future,* 24(12):1355-1362 (1999); *Cell,* 9:243-246 (Oct. 29, 1999); and *Drug Discovery Today,* 5(5):183-194 (May 2000) and Meanwell, N. A. et al., "Inhibitors of the entry of HIV into host cells", *Curr. Op. Drug Dis. Dev.,* 6(4):451-461 (2003). Specifically the compounds can be utilized in combination with other attachment inhibitors, fusion inhibitors, and chemokine receptor antagonists aimed at either the CCR5 or CXCR4 coreceptor.

It will be understood that the scope of combinations of the compounds of this disclosure with AIDS antivirals, immunomodulators, anti-infectives, HIV entry inhibitors or vaccines is not limited to the list in the above Table but includes, in principle, any combination with any pharmaceutical composition useful for the treatment of AIDS.

Preferred combinations are simultaneous or alternating treatments with a compound of the present disclosure and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is REYATAZ® (active ingredient Atazanavir). Typically a dose of 300 to 600 mg is administered once a day. This may be co-administered with a low dose of Ritonavir (50 to 500 mgs). Another preferred inhibitor of HIV protease is KALETRA®. Another useful inhibitor of HIV protease is indinavir, which is the sulfate salt of N-(2 (R)-hydroxy-1-(S)-indanyl)-2(R)-phenylmethyl-4-(S)-hydroxy-5-(1-(4-(3-pyridyl-methyl)-2(S)—N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine. (The preparation of ddC, ddI and AZT are also described in EP 0 484 071.)

In such combinations the compound of the present disclosure and other active agents may be administered separately or in conjunction. In addition, the administration of one element may be prior to, concurrent to, or subsequent to the administration of other agent(s).

GENERAL CHEMISTRY (METHODS OF SYNTHESIS)

The present invention comprises compounds of Formula I, their pharmaceutical formulations, and their use in patients suffering from or susceptible to HIV infection. The compounds of Formula I include pharmaceutically acceptable salts thereof. General procedures to construct compounds of Formula I and intermediates useful for their synthesis are described in the following Schemes (after the Abbreviations).

Abbreviations

One or more of the following abbreviations, most of which are conventional abbreviations well known to those skilled in the art, may be used throughout the description of the disclosure and the examples:

| | |
|---|---|
| h = | hour(s) |
| rt = | room temperature |
| mol = | mole(s) |
| mmol = | millimole(s) |
| g = | gram(s) |
| mg = | milligram(s) |
| mL = | milliliter(s) |
| TFA = | trifluoroacetic Acid |
| DCE = | 1,2-dichloroethane |
| $CH_2Cl_2$ = | dichloromethane |
| TPAP = | tetrapropylammonium perruthenate |
| THF = | tetrahydrofuran |
| DEPBT = | 3-(diethoxyphosphoryloxy)-1,2,3-benzotriazin-4(3H)-one |
| DMAP = | 4-dimethylaminopyridine |
| P-EDC = | polymer supported 1-(3-dimethylaminopropyl)-3-ethylcarbodiimide |
| EDC = | 1-(3-dimethylaminopropyl)-3-ethylcarbodiimide |
| DMF = | N,N-dimethylformamide |
| Hunig's Base = | N,N-diisopropylethylamine |
| MCPBA = | meta-chloroperbenzoic Acid |
| azaindole = | 1H-pyrrolo-pyridine |
| 4-azaindole = | 1H-pyrrolo[3,2-b]pyridine |
| 5-azaindole = | 1H-pyrrolo[3,2-c]pyridine |
| 6-azaindole = | 1H-pyrrolo[2,3-c]pyridine |
| 7-azaindole = | 1H-pyrrolo[2,3-b]pyridine |
| PMB = | 4-methoxybenzyl |
| DDQ = | 2,3-dichloro-5,6-dicyano-1,4-benzoquinone |
| OTf = | trifluoromethanesulfonoxy |
| NMM = | 4-methylmorpholine |
| PIP-COPh = | 1-benzoylpiperazine |
| NaHMDS = | sodium hexamethyldisilazide |
| EDAC = | 1-(3-dimethylaminopropyl)-3-ethylcarbodiimide |
| TMS = | trimethylsilyl |
| DCM = | dichloromethane |
| DCE = | dichloroethane |
| MeOH = | methanol |
| THF = | tetrahydrofuran |
| EtOAc = | ethyl acetate |
| LDA = | lithium diisopropylamide |
| TMP-Li = | 2,2,6,6-tetramethylpiperidinyl lithium |
| DME = | dimethoxyethane |
| DIBALH = | diisobutylaluminum hydride |
| HOBT = | 1-hydroxybenzotriazole |
| CBZ = | benzyloxycarbonyl |
| PCC = | pyridinium chlorochromate |
| TBTU = | O-(benzotriazol-1-yl)-N,N,N',N'-tetramethyluronium tetrafluoroborate |
| DEBPT = | 3-(diethoxyphosphoryloxy)-1,2,3-benzotriazin-4(3H)-one |
| BOP = | benzotriazole-1-yl-oxy-tris-(dimethylamino)-phosphoniumhexafluorophosphate |

Preparation of Compounds of Formula I, Chemistry Schemes:

A general reaction scheme is set forth as follows:

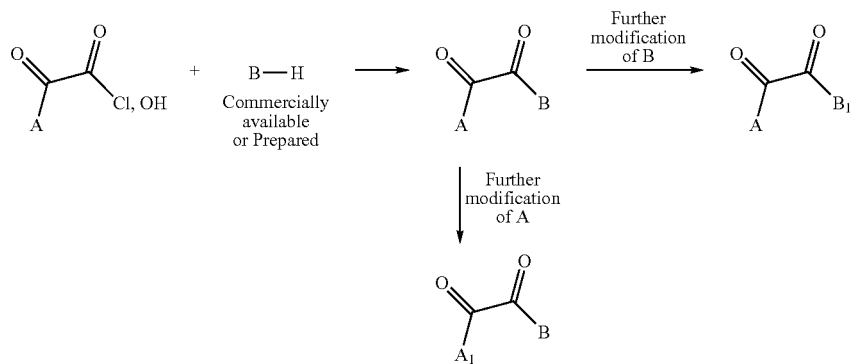
For the preparation of substituent "A" above, the procedures set forth in U.S. Pat. Nos. 6,476,034, 6,573,262, 6,469,006 and 7,354,924, as well as WO 2004/04337 are useful, and are incorporated herein by reference in their entirety.
Other specialized procedures are as follows:
For Compound 1:
Compounds 2, 3:
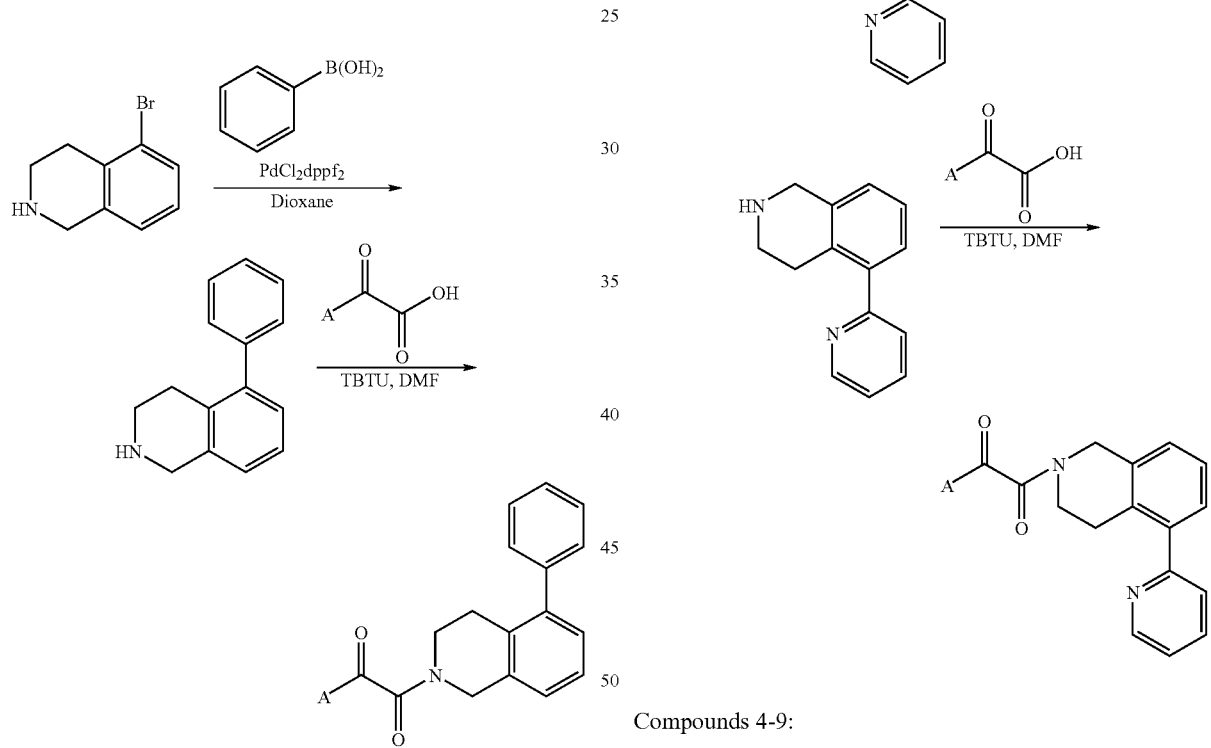
Compounds 4-9:
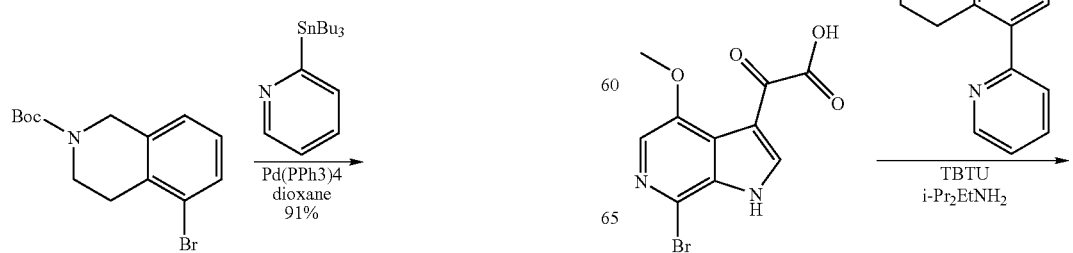

Compounds 18-20:
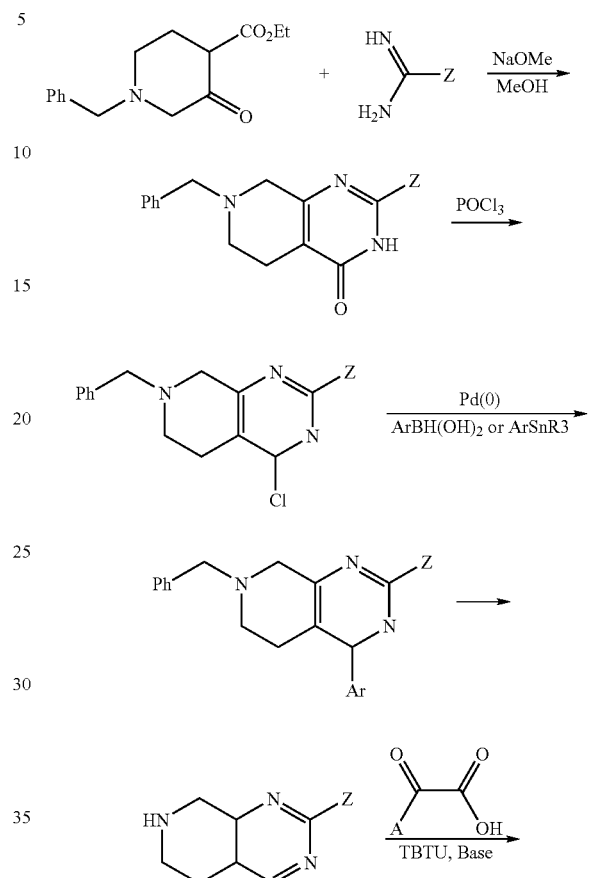
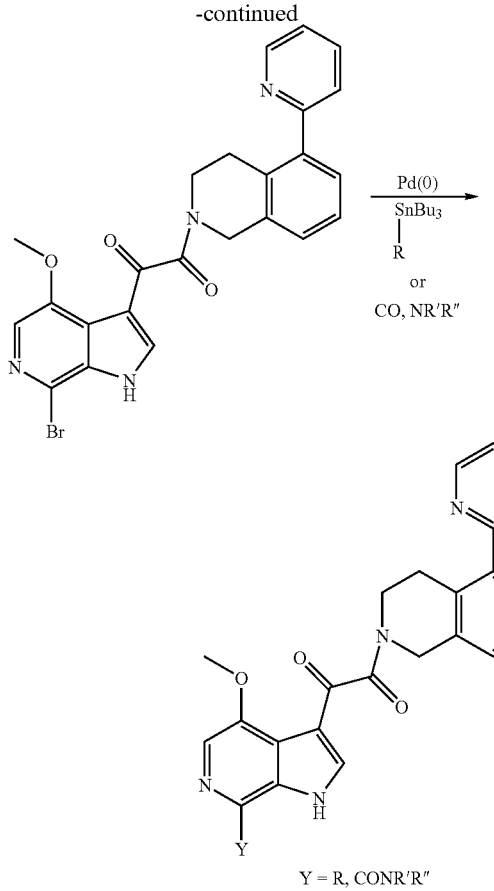
Y = R, CONR'R"
Compounds 10-17:
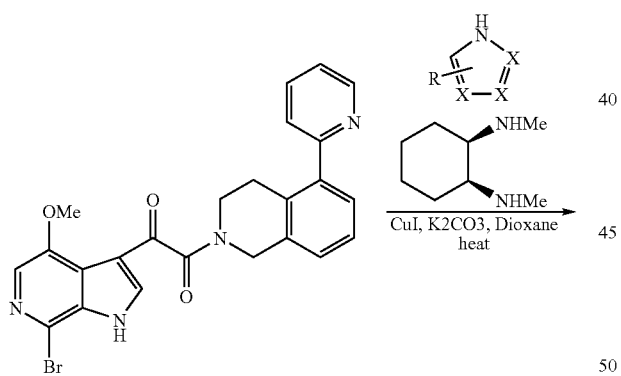
Z = H, Me, c-Pr, NMe2, etc.
Compounds 21 and 22:
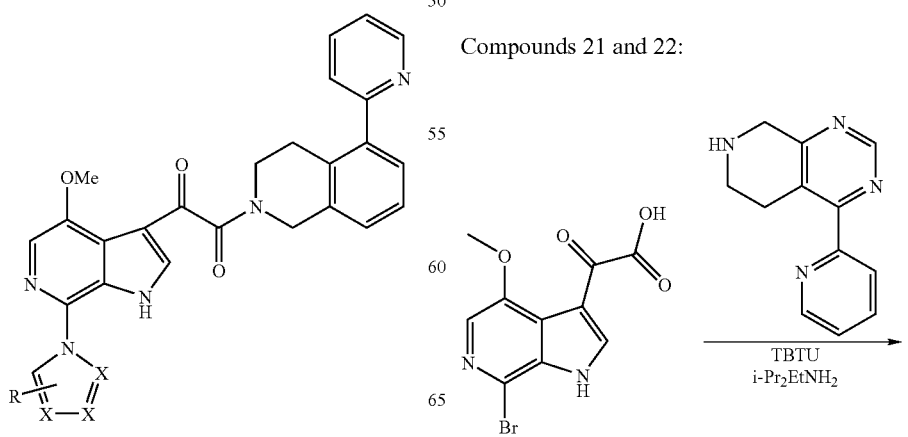

37
-continued
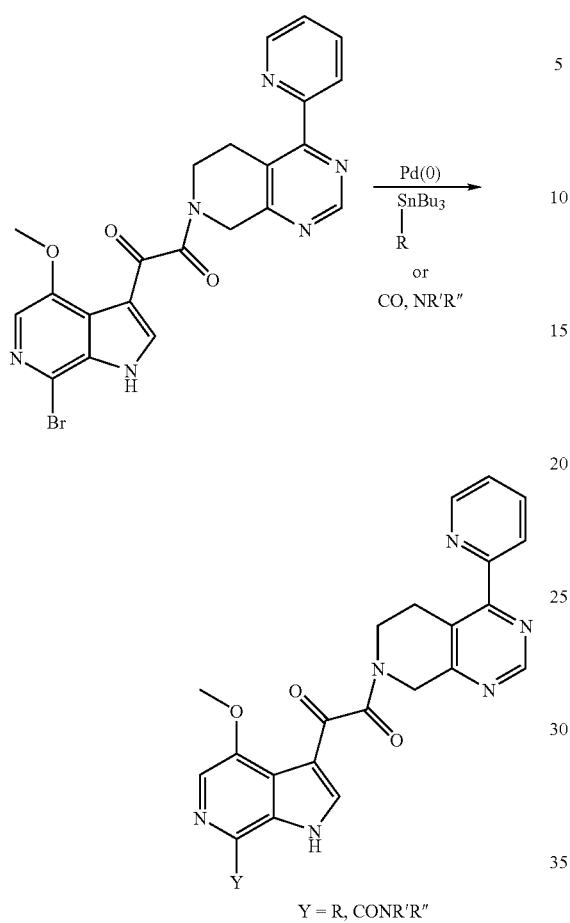
Compound 23:
38
-continued
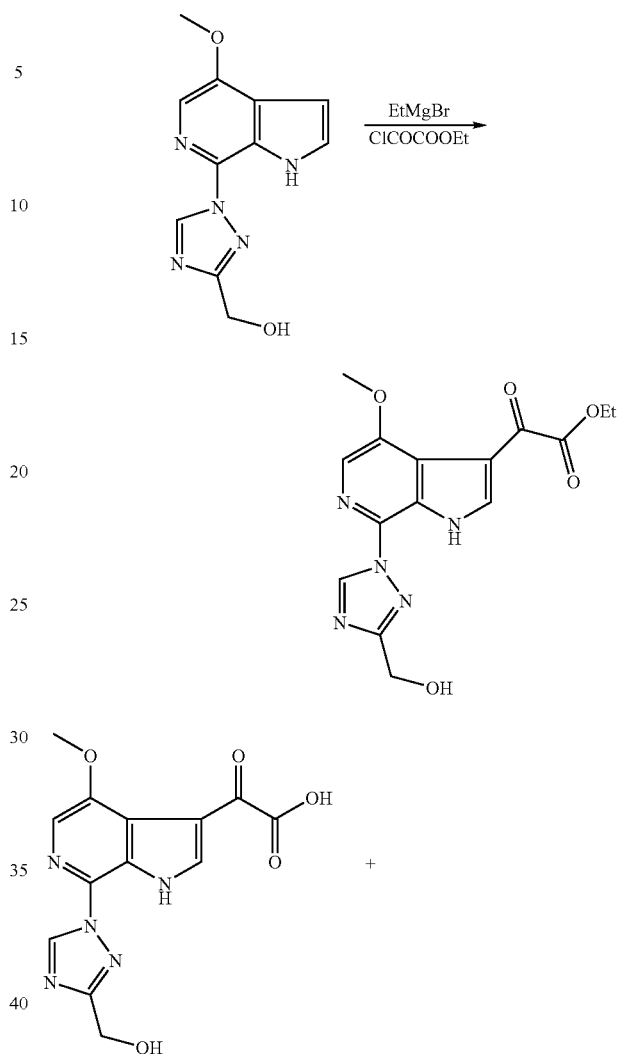
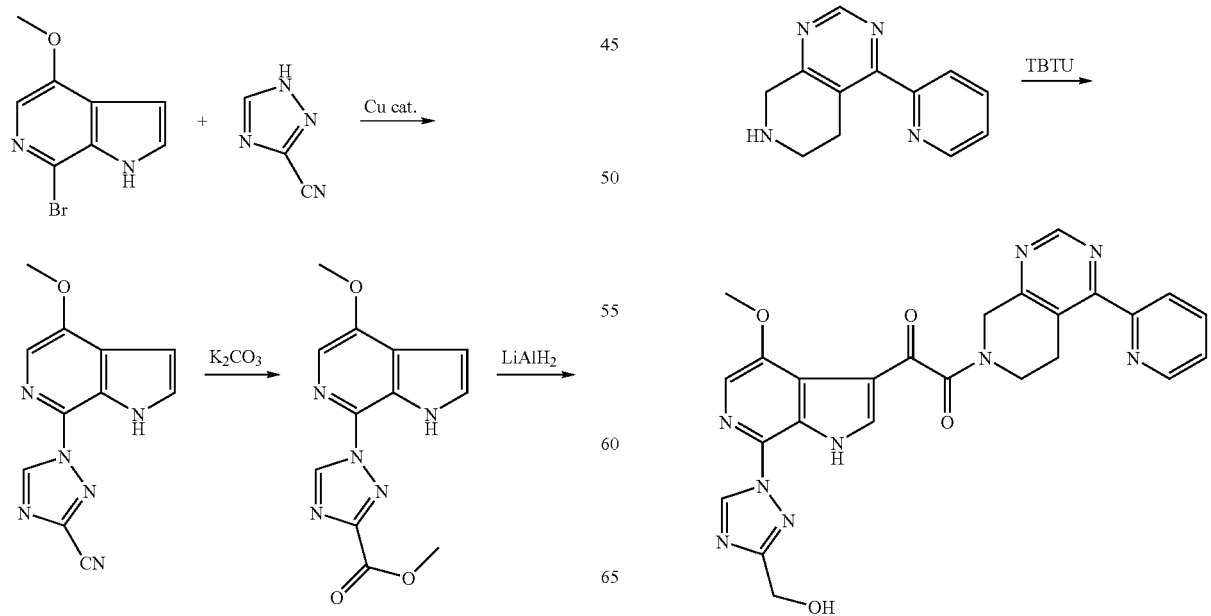

Compound 24:
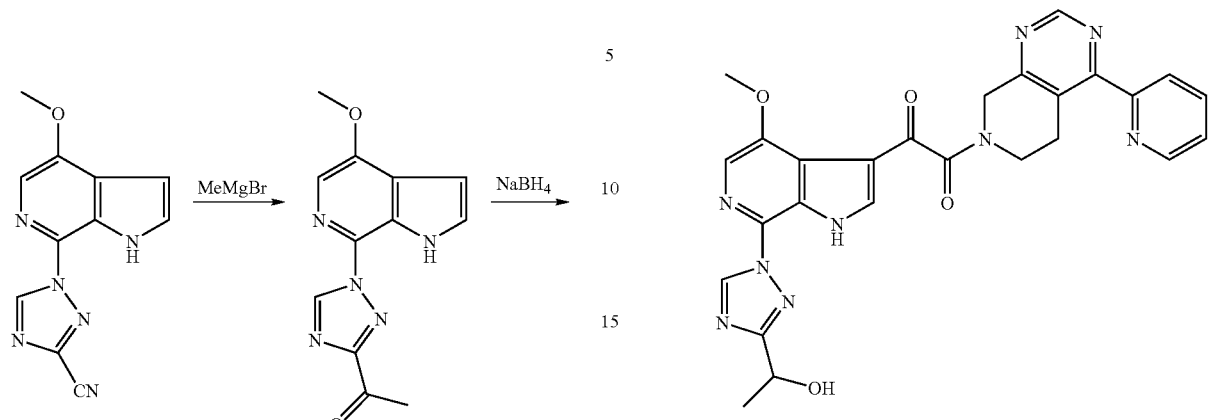
Compound 25:
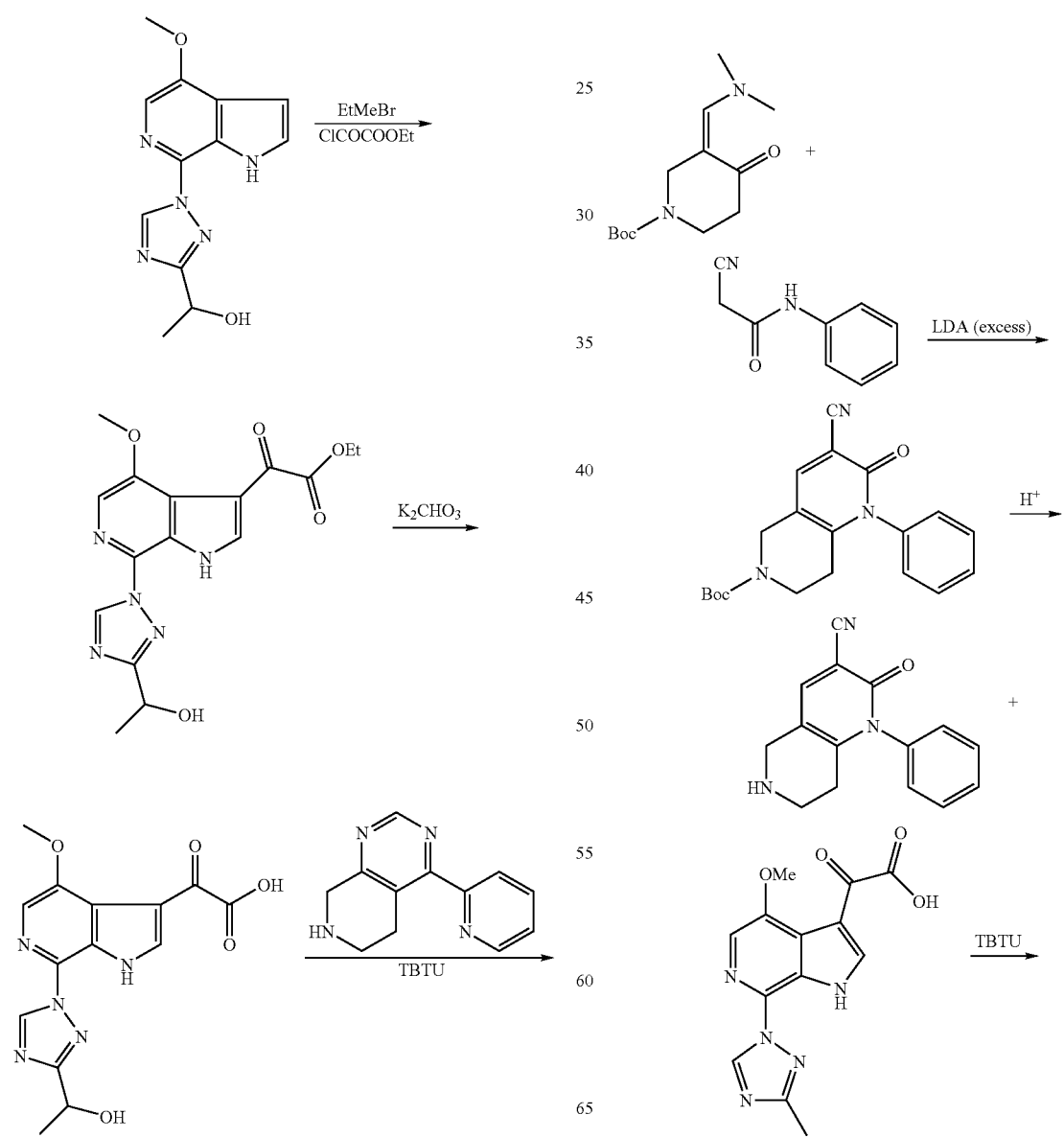

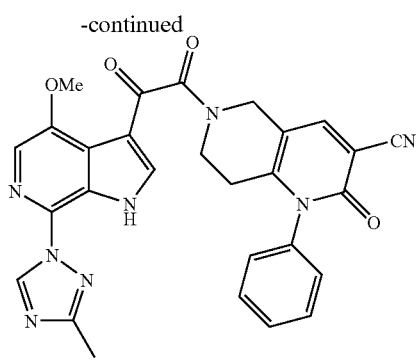

Compounds 26 and 27:

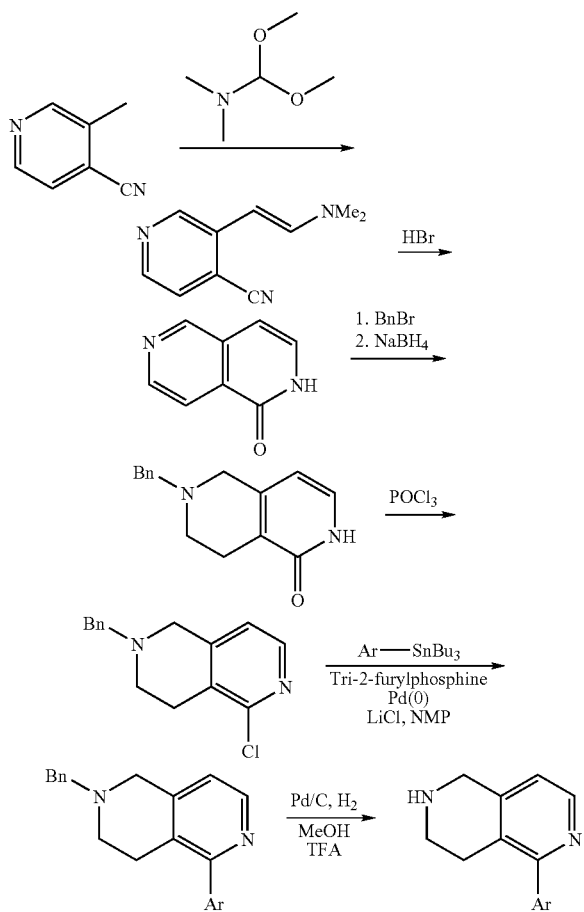

EXAMPLES

The following examples illustrate typical syntheses of the compounds of Formula I as described generally above. These examples are illustrative only and are not intended to limit the disclosure in any way. The reagents and starting materials are readily available to one of ordinary skill in the art.

Chemistry

Typical Procedures and Characterization of Selected Examples:

Unless otherwise stated, solvents and reagents were used directly as obtained from commercial sources, and reactions were performed under a nitrogen atmosphere. Flash chromatography was conducted on Silica gel 60 (0.040-0.063 particle size; EM Science supply). $^1$H NMR spectra were recorded on Bruker DRX-500f at 500 MHz (or Bruker DPX-300B or Varian Gemini 300 at 300 MHz as stated). The chemical shifts were reported in ppm on the δ scale relative to δTMS=0. The following internal references were used for the residual protons in the following solvents: CDCl$_3$ ($\delta_H$ 7.26), CD$_3$OD ($\delta_H$ 3.30), and DMSO-d$_6$ ($\delta_H$ 2.50). Standard acronyms were employed to describe the multiplicity patterns: s (singlet), d (doublet), t (triplet), q (quartet), m (multiplet), b (broad), app (apparent). The coupling constant (J) is in Hertz. All Liquid Chromatography (LC) data were recorded on a Shimadzu LC-10AS liquid chromatograph using a SPD-10AV UV-Vis detector with Mass Spectrometry (MS) data determined using a MICROMASS® Platform for LC in electrospray mode.

The preparation of templates A-CO—CO—Cl and A-CO—CO—OH unless specifically noted has been described in detail in U.S. Pat. Nos. 6,469,006 B1, 6,573,262 B2 and 6,900,323 B2, U.S. Publication No. 2005/0090522 A1, U.S. Pat. No. 6,825,201, U.S. Publication Nos. 2005/0261296 A1, 2004/0186292 A1 and 2005/0267130 A1, U.S. Pat. No. 6,900,206 B2, U.S. Publication No. 2004/0063746, WO 00/076521, WO 00/162255, WO 00/204440, WO 02/062423, WO 02/085301, WO 03/068221 or U.S. Publication No. 2004/0063744, each of which are incorporated herein in their entirety by reference.

LC/MS Methods (i.e., Compound Identification)

LC/MS Methods:
Method 1:
Start % B=0, Final % B=100 over 3 minute gradient (1 minutes collected after run)
Flow Rate=4 mL/min
Solvent A=5% ACN-95% H$_2$O-10 mm Ammonium Acetate
Solvent B=95% ACN-5% H$_2$O-10 mm Ammonium Acetate
Column: PHENOMENEX® Luna 4.6×50 mm S10
Method 2:
Start % B=0, Final % B=100 over 3 minute gradient (1 minutes collected after run)
Flow Rate=4 mL/min
Solvent A=10% ACN-90% H$_2$O-0.1% TFA
Solvent B=90% ACN-10% H$_2$O-0.1% TFA
Column: Sunfire C18 4.6×50 mm 5μ
Method 3:
Start % B=0, Final % B=100 over 3 minute gradient (1 minutes collected after run)
Flow Rate=4 mL/min
Solvent A=10% MeOH-90% H$_2$O-0.1% TFA
Solvent B=90% MeOH-10% H$_2$O-0.1% TFA
Column: PHENOMENEX® Luna 3.0×50 mm S10
Method 4:
Start % B=0, Final % B=100 over 3 minute gradient
Flow Rate=4 mL/min
Solvent A=5% ACN-95% H$_2$O-10 mm Ammonium Acetate
Solvent B=95% ACN-5% H$_2$O-10 mm Ammonium Acetate
Column: PHENOMENEX® Luna 4.6×50 mm S10
Method 5:
Start % B=0, Final % B=100 over 3 minute gradient
Flow Rate=4 mL/min
Solvent A=10% ACN-90% H$_2$O-0.1% TFA
Solvent B=90% ACN-10% H$_2$O-0.1% TFA
Column: Sunfire C18 4.6×50 mm 5μ
Method 6:
Start % B=0, Final % B=100 over 2 minute gradient (1 minutes collected after run)

Flow Rate=4 mL/min
Solvent A=10% ACN-90% H$_2$O-0.1% TFA
Solvent B=90% ACN-10% H$_2$O-0.1% TFA
Column: Sunfire C18 4.6×50 mm 5μ
Method 7:
Start % B=0, Final % B=100 over 2 minute gradient (1 minutes collected after run)
Flow Rate=4 mL/min
Solvent A=5% ACN-95% H$_2$O-10 mm Ammonium Acetate
Solvent B=95% ACN-5% H$_2$O-10 mm Ammonium Acetate
Column: PHENOMENEX® Luna 4.6×50 mm S10
Method 8:
Start % B=0, Final % B=100 over 2 minute gradient (1 minutes collected after run)
Flow Rate=4 mL/min
Solvent A=10% MeOH-90% H$_2$O-0.1% TFA
Solvent B=90% MeOH-10% H$_2$O-0.1% TFA
Column: PHENOMENEX® Luna 3.0×50 mm S10
Method 9:
Start % B=0, Final % B=100 over 3 minute gradient (1 minutes collected after run)
Flow Rate=4 mL/min
Solvent A=5% ACN-95% H$_2$O-10 mm Ammonium Acetate
Solvent B=95% ACN-5% H$_2$O-10 mm Ammonium Acetate
Column: Xbridge C18 4.6×50 mm S5
Method 10:
Start % B=0, Final % B=100 over 3 minute gradient (1 minutes collected after run)
Flow Rate=4 mL/min
Solvent A=10% MeOH-90% H$_2$O-0.1% TFA
Solvent B=90% MeOH-10% H$_2$O-0.1% TFA
Column: PHENOMENEX® 10μ 3.0×50 mm

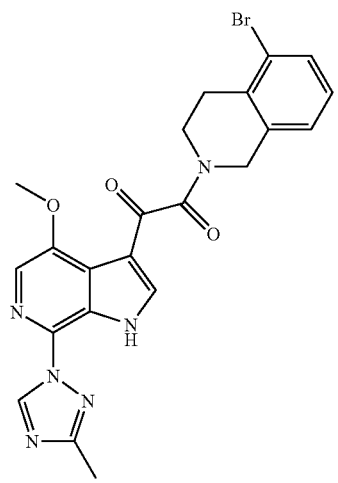

Preparation of 1-(5-bromo-3,4-dihydroisoquinolin-2 (1H)-yl)-2-(4-methoxy-7-(3-methyl-1H-1,2,4-triazol-1-yl)-1H-pyrrolo[2,3-c]pyridin-3-yl)ethane-1,2-dione A 20 mL vial was charged with 2-(4-methoxy-7-(3-methyl-1H-1,2,4-triazol-1-yl)-1H-pyrrolo[2,3-c]pyridin-3-yl)-2-oxoacetic acid (0.1 g, 0.332 mmol), 5-bromo-1,2,3,4-tetrahydroisoquinoline (0.083 g, 0.332 mmol), o-benzotriazol-1-yl-N,N,N',N'-tetramethyluronium tetrafluoroborate (0.133 g, 0.415 mmol), Hunig's Base (0.580 mL, 3.32 mmol), and DMF (3 mL). The vial was sealed and stirred at rt. After stirring the mixture for 70.5 h, the reaction was quenched with water. The solids that formed were collected by filtration. The mother liquor was concentrated under reduced pressure, and a second batch of solids was collected by recrystallizing from MeOH and water. The expected product, 1-(5-bromo-3,4-dihydroisoquinolin-2(1H)-yl)-2-(4-methoxy-7-(3-methyl-1H-1,2,4-triazol-1-yl)-1H-pyrrolo[2,3-c]pyridin-3-yl) ethane-1,2-dione (0.145 g, 0.293 mmol, 88% yield), was isolated as an off-white solid. LC/MS: m/z 495 (M+H)$^+$, 497.02 (M+3H)$^+$ 1.935 min (method 1). $^1$H NMR (500 MHz, DMSO-d$_6$) δ ppm 12.42 (s, 1H) 9.22-9.27 (m, 1H) 8.18-8.31 (m, 1H) 7.84 (s, 1H) 7.09-7.59 (m, 3H) 4.59-4.87 (m, 2H) 3.67-3.95 (m, 5H) 2.73-2.96 (m, 2H) 2.47-2.52 (m, 3H).

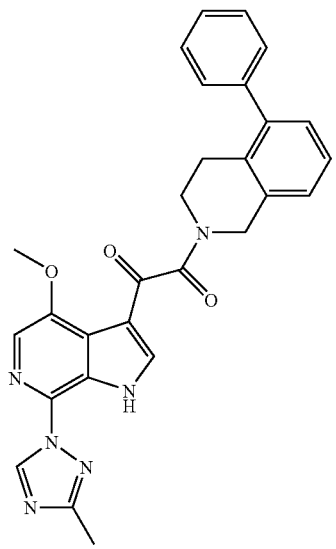

Preparation of 1-(4-methoxy-7-(3-methyl-1H-1,2,4-triazol-1-yl)-1H-pyrrolo[2,3-c]pyridin-3-yl)-2-(5-phenyl-3,4-dihydroisoquinolin-2(1H)-yl)ethane-1,2-dione, Compound 1

To a sealable vial containing 1-(5-bromo-3,4-dihydroisoquinolin-2(1H)-yl)-2-(4-methoxy-7-(3-methyl-1H-1,2,4-triazol-1-yl)-1H-pyrrolo[2,3-c]pyridin-3-yl)ethane-1,2-dione (0.05 g, 0.101 mmol) was added phenylboronic acid (0.018 g, 0.151 mmol), PdCl$_2$(dppf)-CH$_2$Cl$_2$ adduct (0.016 g, 0.020 mmol), K$_2$CO$_3$ (0.06 g, 0.434 mmol), 1,4-dioxane (2 mL), and water (0.5 mL). The vessel was flushed with N$_2$, then the vial was sealed and heated to 85° C. After 2 h the mixture was cooled to rt, and concentrated under reduced pressure. The residue was diluted with water (30 mL) and extracted with dichloromethane (3×30 mL). The organic solution was dried with Na$_2$SO$_4$, the drying agent was removed by filtration, and the organic solution was concentrated under reduced pressure. The residue was purified by prep HPLC. Some impurities were still present by LC/MS, so the mixture was further purified by flash chromatography using a 0-5% MeOH in dichloromethane gradient. The expected product, 1-(4-methoxy-7-(3-methyl-1H-1,2,4-triazol-1-yl)-1H-pyrrolo[2,3-c]pyridin-3-yl)-2-(5-phenyl-3,4-dihydroisoquinolin-2(1H)-yl)ethane-1,2-dione (0.024 g, 0.049 mmol, 48.3% yield), was isolated as an off-white solid. LC/MS: m/z 493.25 (M+H)$^+$, 2.12 min (method 1). $^1$H NMR (500 MHz, chloroform-d) δ ppm 11.01 (br. s., 1H) 9.14 (s, 1H) 8.19-8.27 (m, 1H) 7.67-7.72 (m, 1H) 7.01-7.50 (m, 8H) 4.74-5.00 (m, 2H) 3.67-3.87 (m, 5H) 2.79-2.98 (m, 2H) 2.55-2.61 (m, 3H).

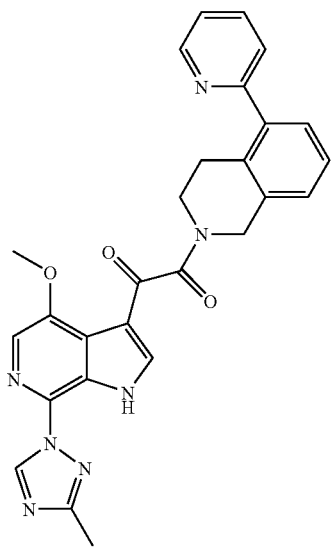

Preparation of 1-(4-methoxy-7-(3-methyl-1H-1,2,4-triazol-1-yl)-1H-pyrrolo[2,3-c]pyridin-3-yl)-2-(5-(pyridin-2-yl)-3,4-dihydroisoquinolin-2(1H)-yl)ethane-1,2-dione, TFA, compound 2

To a sealable flask containing 1-(5-bromo-3,4-dihydroisoquinolin-2(1H)-yl)-2-(4-methoxy-7-(3-methyl-1H-1,2,4-triazol-1-yl)-1H-pyrrolo[2,3-c]pyridin-3-yl)ethane-1,2-dione (0.15 g, 0.303 mmol) was added 2-tri-n-butylstannylpyridine (0.116 mL, 0.363 mmol) and tetrakis(triphenylphosphine)palladium(0) (0.035 g, 0.030 mmol). The mixture was diluted with 1,4-dioxane (3 mL), and was flushed with $N_2$. The flask was sealed and was heated to 100° C. overnight. The reaction showed almost entirely starting material by LC/MS. To the mixture was added 0.07 g of $Pd(PPh_3)_4$, and 0.116 mL of 2-tri-n-butylstannylpyridine. The mixture was flushed with $N_2$, the flask was sealed and was heated for 71 h at 100° C. The mixture was cooled to rt and was diluted with MeOH and dichloromethane then was filtered through a pad of CELITE® to remove solids. The organic solution was concentrated under reduced pressure and was purified by BIOTAGE® flash chromatography using a 0-7% MeOH in dichloromethane gradient. The expected product still contained impurities, so the mixture was purified further by prep HPLC. The expected product, 1-(4-methoxy-7-(3-methyl-1H-1,2,4-triazol-1-yl)-1H-pyrrolo[2,3-c]pyridin-3-yl)-2-(5-(pyridin-2-yl)-3,4-dihydroisoquinolin-2(1H)-yl)ethane-1,2-dione, TFA (0.048 g, 0.079 mmol, 26.1% yield), was isolated as an off-white solid. LC/MS: m/z 492.35 (M+H)$^+$, 1.635 min (method 1). $^1$H NMR (500 MHz, DMSO-$d_6$) δ ppm 12.40-12.46 (m, 1H) 9.24 (s, 1H) 8.69-8.81 (m, 1H) 8.24-8.30 (m, 1H) 8.03-8.16 (m, 1H) 7.83-7.87 (m, 1H) 7.64-7.77 (m, 1H) 7.51-7.62 (m, 1H) 7.26-7.50 (m, 3H) 4.65-4.93 (m, 2H) 3.78-3.84 (m, 3H) 3.57-3.78 (m, 2H) 2.82-3.01 (m, 2H) 2.48-2.53 (m, J=6.10 Hz, 3H).

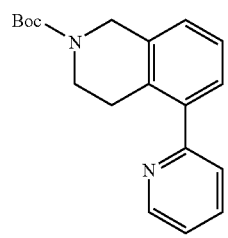

Preparation of t-butyl 5-(pyridin-2-yl)-3,4-dihydroisoquinoline-2(1H)-carboxylate To a 350 mL sealable flask was added t-butyl 5-bromo-3,4-dihydroisoquinoline-2(1H)-carboxylate (3.67 g, 11.77 mmol) and tri-n-butyl(2-pyridyl)tin (5.2 g, 14.12 mmol. The mixture was dissolved in dioxane (100 mL) and tetrakis(triphenylphosphine)palladium(0) (2.72 g, 2.354 mmol) was added. The mixture was flushed with $N_2$ and the flask was sealed and heated to 110° C. After heating the mixture for 65 h, the mixture was cooled to rt and was filtered through a pad of CELITE® to remove the solids. The CELITE® was washed with MeOH and the organic solution was concentrated under reduced pressure. The residue was purified using BIOTAGE® flash chromatography and a 10-50% EtOAc in hexanes gradient. The expected product, tert-butyl 5-(pyridin-2-yl)-3,4-dihydroisoquinoline-2(1H)-carboxylate (3.33 g, 10.72 mmol, 91% yield), was isolated as a thick yellow oil. LC/MS: m/z 311.02 (M+H)$^+$, 2.257 min (method 1). $^1$H NMR (500 MHz, chloroform-d) δ ppm 8.70 (d, J=4.88 Hz, 1H) 7.77 (t, J=7.32 Hz, 1H) 7.40 (d, J=7.93 Hz, 1H) 7.23-7.32 (m, 3H) 7.19 (br. s., 1H) 4.64 (br. s., 2H) 3.55 (br. s., 2H) 2.86 (t, J=5.95 Hz, 2H) 1.48 (br. s., 9H).

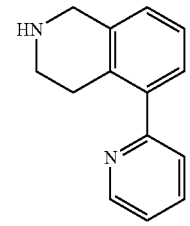

Preparation of 5-(pyridin-2-yl)-1,2,3,4-tetrahydroisoquinoline, TFA

To a solution of tert-butyl 5-(pyridin-2-yl)-3,4-dihydroisoquinoline-2(1H)-carboxylate (3.32 g, 10.70 mmol) in $CH_2Cl_2$ (40 mL) was added TFA (10 mL, 130 mmol). After 6 h of stirring at rt, the solvent was removed under reduced pressure to give the expected product as a light-red oil (10.70 mmol, 3.29 g, 100% yield). The product was used directly in the next step with no additional purification. LC/MS: m/z 211.09 (M+H)$^+$, 1.485 min (method 1).

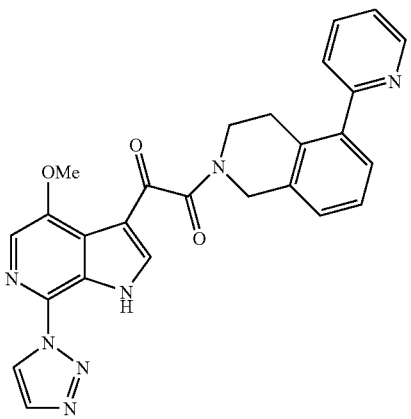

Preparation of 1-(4-methoxy-7-(1H-1,2,3-triazol-1-yl)-1H-pyrrolo[2,3-c]pyridin-3-yl)-2-(5-(pyridin-2-yl)-3,4-dihydroisoquinolin-2(1H)-yl)ethane-1,2-dione, Compound 3

A mixture of 5-(pyridin-2-yl)-1,2,3,4-tetrahydroisoquinoline (81 mg, 0.383 mmol), 2-(1H-benzo[d][1,2,3]triazol-1-yl)-1,1,3,3-tetramethylisouronium tetrafluoroborate (134 mg, 0.418 mmol) and N-ethyl-N-isopropylpropan-2-amine (225 mg, 1.741 mmol) in DMF (2 mL) was stirred for 1 hour at room temperature, LCMS indicated the formation of the desired product. The reaction mixture was filtered and the clear solution was purified by prep. HPLC to give 1-(4-methoxy-7-(1H-1,2,3-triazol-1-yl)-1H-pyrrolo[2,3-c]pyridin-3-yl)-2-(5-(pyridin-2-yl)-3,4-dihydroisoquinolin-2(1H)-yl)ethane-1,2-dione as white solid (29 mg, 16%). LCMS: m/e 480.11 (M+H)$^+$, 1.63 min (method 9). $^1$H NMR (500 MHz, DMSO-$d_6$) d ppm 2.79-3.08 (m, 2H) 3.54-3.80 (m, 2H) 3.81-3.92 (m, 3H) 4.65-4.97 (m, 2H) 7.23-7.56 (m, 4H) 7.59-7.75 (m, 1H) 7.91-8.15 (m, 3H) 8.21-8.33 (m, 1H) 8.63-8.83 (m, 1H) 8.94 (s, 1H) 12.79 (s, 1H).

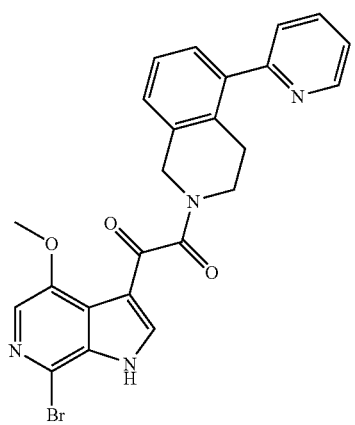

Preparation of 1-(7-bromo-4-methoxy-1H-pyrrolo[2,3-c]pyridin-3-yl)-2-(5-(pyridin-2-yl)-3,4-dihydroisoquinolin-2(1H)-yl)ethane-1,2-dione To a 250 mL flask was added 5-(pyridin-2-yl)-1,2,3,4-tetrahydroisoquinoline (2.250 g, 10.7 mmol) and 2-(7-bromo-4-methoxy-1H-pyrrolo[2,3-c]pyridin-3-yl)-2-oxoacetic acid (2.75 g, 9.19 mmol). The mixture was diluted with DMF (100 mL) and Hunig's Base (16.6 mL, 95 mmol) and o-benzotriazol-1-yl-N,N,N',N'-tetramethyluronium tetrafluoroborate (4 g, 12.46 mmol) was added to the mixture. The mixture was stirred at rt for 70 h, quenched with water (50 mL) and the solvent removed under reduced pressure. The residue was diluted with water (100 mL) and extracted with dichloromethane (3×100 mL). The combined organic layers were dried with Na$_2$SO$_4$. The drying agent was removed by filtration and the residue purified by BIOTAGE® flash chromatography using a 0-5% MeOH in dichloromethane gradient. The residue still had impurities by $^1$H NMR so it was dissolved in dichloromethane (150 mL) and washed with sat. NaHCO$_3$ (100 mL) then with sat. ammonium chloride (150 mL). The organic solution was dried with Na$_2$SO$_4$, the drying agent was removed by filtration, and the solution was concentrated under reduced pressure to give 1-(7-bromo-4-methoxy-1H-pyrrolo[2,3-c]pyridin-3-yl)-2-(5-(pyridin-2-yl)-3,4-dihydroisoquinolin-2(1H)-yl)ethane-1,2-dione (3.40 g, 6.92 mmol, 75% yield) as a blue solid. The product still had some impurities by 1H NMR, but was used in the next step with no additional purification. LC/MS: m/z 489.14 (M+H)$^+$, 1.169 min (method 1). $^1$H NMR (500 MHz, chloroform-d) δ ppm 10.89 (br. s., 1H) 8.62-8.80 (m, 1H) 7.64-7.95 (m, 3H) 6.98-7.49 (m, 5H) 4.66-4.99 (m, 2H) 3.60-3.87 (m, 5H) 2.87-3.12 (m, 2H).

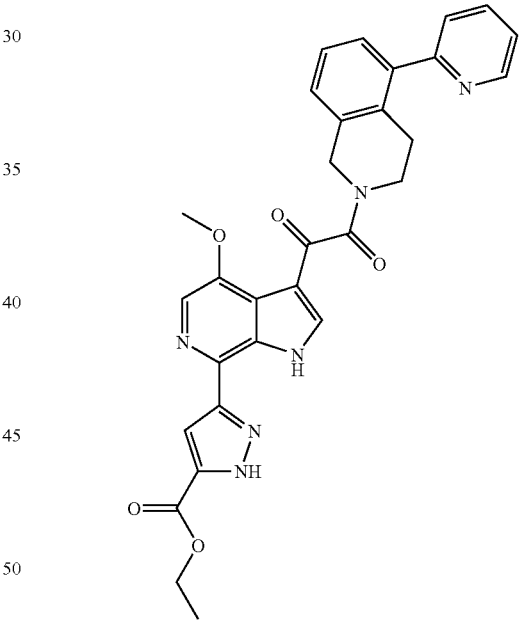

Preparation of ethyl 3-(4-methoxy-3-(2-oxo-2-(5-(pyridin-2-yl)-3,4-dihydroisoquinolin-2(1H)-yl)acetyl)-1H-pyrrolo[2,3-c]pyridin-7-yl)-1H-pyrazole-5-carboxylate To a sealable rb flask containing 1-(7-bromo-4-methoxy-1H-pyrrolo[2,3-c]pyridin-3-yl)-2-(5-(pyridin-2-yl)-3,4-dihydroisoquinolin-2(1H)-yl)ethane-1,2-dione (0.5 g, 1.018 mmol) and ethyl 3-(tributylstannyl)-1H-pyrazole-5-carboxylate (0.480 g, 1.119 mmol) in 1,4-dioxane (2 mL) was added tetrakis(triphenylphosphine)palladium(0) (0.235 g, 0.204 mmol). The flask was flushed with N$_2$, sealed, and heated to 110° C. After heating the mixture for 17 h, the mixture was cooled to rt. The crude LC/MS showed no starting material remained and the mass for the expected product was present. The crude mixture was diluted with MeOH and was passed through a plug of CELITE® to remove solids. The CELITE® was washed with MeOH, and the organic solution was concentrated under reduced pressure. The residue was diluted with MeOH and ether was added slowly to the mixture. The product that formed was collected by filtration and washed with MeOH. The mother liquor was concentrated under reduced pressure. A second recrystallization was performed using hot MeOH and Et$_2$O. The expected product, ethyl 3-(4-methoxy-3-(2-oxo-2-(5-(pyridin-2-yl)-3,4-dihydroisoquinolin-2(1H)-yl)acetyl)-1H-pyrrolo[2,3-c]pyridin-7-yl)-1H-pyrazole-5-carboxylate (0.17 g, 0.309 mmol, 30.3% yield), was isolated as a light-brown solid and was used in the next step although impurities were still apparent by $^1$H NMR. LC/MS: m/z 551.18 (M+H)$^+$, 1.778 min (method 1). $^1$H NMR (500 MHz, DMSO-d$_6$) δ ppm 14.04-14.50 (m, 1H) 11.90-12.88 (m, 1H) 8.58-8.76 (m, 1H) 7.81-8.28 (m, 3H) 7.14-7.67 (m, 6H) 4.29-4.96 (m, 4H) 3.53-3.89 (m, 5H) 2.79-3.06 (m, 2H) 1.36 (t, J=7.02 Hz, 3H).

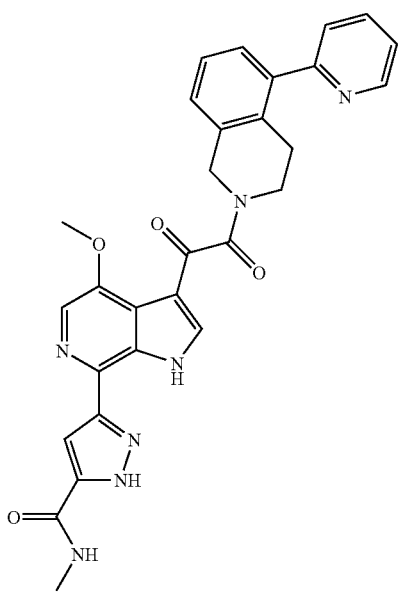

Preparation of 3-(4-methoxy-3-(2-oxo-2-(5-(pyridin-2-yl)-3,4-dihydroisoquinolin-2(1H)-yl)acetyl)-1H-pyrrolo[2,3-c]pyridin-7-yl)-N-methyl-1H-pyrazole-5-carboxamide, TFA, Compound 4

To a sealable vial containing ethyl 3-(4-methoxy-3-(2-oxo-2-(5-(pyridin-2-yl)-3,4-dihydroisoquinolin-2(1H)-yl)acetyl)-1H-pyrrolo[2,3-c]pyridin-7-yl)-1H-pyrazole-5-carboxylate (0.051 g, 0.093 mmol) was added methylamine (1.5 mL, 3.00 mmol). The vial was sealed and heated to 40° C. for 15 h. The mixture was cooled to rt and methylamine (1.5 mL, 3.00 mmol) was added. The flask was sealed and heated to 60° C. After heating the mixture for 22 h, the mixture was cooled to rt. To the mixture was added methylamine (1.5 mL, 3.00 mmol). The vial was sealed and the mixture was heated to 60° C. for 118 h. The mixture was cooled to rt and the solvent was removed under reduced pressure. The residue was dissolved in DMF and passed through a plug of glass wool. The DMF solution was purified by prep HPLC. The fractions containing the product were stripped of solvent under reduced pressure. The residue was dissolved in DMF and was purified further by prep HPLC. The expected product, 3-(4-methoxy-3-(2-oxo-2-(5-(pyridin-2-yl)-3,4-dihydroisoquinolin-2(1H)-yl)acetyl)-1H-pyrrolo[2,3-c]pyridin-7-yl)-N-methyl-1H-pyrazole-5-carboxamide, TFA (0.016 g, 0.023 mmol, 25.3% yield), was isolated as a light-yellow solid. LC/MS: m/z 536.05 (M+H)$^+$ 0.830 min (method 2). $^1$H NMR (500 MHz, DMSO-d$_6$) δ ppm 12.27 (br. s., 1H) 8.67-8.79 (m, 1H) 8.59 (br. s., 1H) 8.24-8.33 (m, 1H) 7.97-8.14 (m, 2H) 7.22-7.73 (m, 6H) 4.66-4.91 (m, 2H) 3.80-3.88 (m, 3H) 3.54-3.79 (m, 2H) 2.78-3.03 (m, 5H).

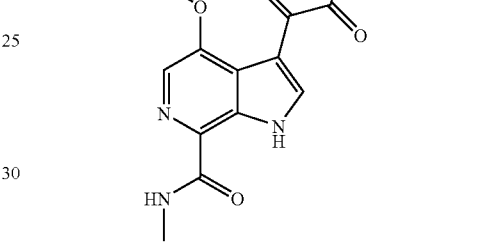

Preparation of 4-methoxy-N-methyl-3-(2-oxo-2-(5-(pyridin-2-yl)-3,4-dihydroisoquinolin-2(1H)-yl)acetyl)-1H-pyrrolo[2,3-c]pyridine-7-carboxamide, Compound 5

To a stainless steel pressure vessel containing 1-(7-bromo-4-methoxy-1H-pyrrolo[2,3-c]pyridin-3-yl)-2-(5-(pyridin-2-yl)-3,4-dihydroisoquinolin-2(1H)-yl)ethane-1,2-dione (0.2 g, 0.407 mmol) was added 1,4-dioxane (5 mL), water (0.037 mL, 2.035 mmol), tetrakis(triphenylphosphine)palladium(0) (0.071 g, 0.061 mmol), triethylamine (0.567 mL, 4.07 mmol), and methylamine (2M in THF) (2.035 mL, 4.07 mmol). The vessel was sealed and purged with N$_2$ 3 times. The vessel was filled with carbon monoxide to 50 psi, and purged 2 times, then finally was filled to 80 psi of carbon monoxide. The vessel was heated to 80° C. for 16 h then was cooled to rt. The mixture was transferred to a rb flask and the solvent was removed under reduced pressure. The residue was dissolved in DMF and was passed through a plug of CELITE® to remove the solids. The DMF solution was purified by prep HPLC. The fractions containing the expected product were concentrated under reduced pressure. The residue was dissolved in dichloromethane and was partitioned with aq. sat. NaHCO$_3$. The organic layer was collected, and dried with MgSO$_4$. The drying agent was removed by filtration and the organic solution was concentrated under reduced pressure. The residue was purified by BIOTAGE® flash chromatography using a 0-5% MeOH in dichloromethane gradient using a BIOTAGE® flash chromatography. The expected product, 4-methoxy-N-methyl-3-(2-oxo-2-(5-(pyridin-2-yl)-3,4-dihydroisoquinolin-2(1H)-yl)acetyl)-1H-pyrrolo[2,3-c]pyridine-7-carboxamide (0.065 g, 0.133 mmol, 32.7% yield), was isolated as an off-white solid. LC/MS: m/z 470.24 (M+H)+, 1.582 min (method 1). $^1$H NMR (500 MHz, DMSO-d$_6$) δ ppm 11.13 (br. s., 1H) 8.60-8.77 (m, 1H) 8.14-8.26 (m, 1H) 7.70-7.94 (m, 3H) 7.02-7.47 (m, 5H) 4.73-5.01 (m, 2H) 3.88-3.97 (m, 3H) 3.66-3.88 (m, 2H) 2.92-3.11 (m, 5H).

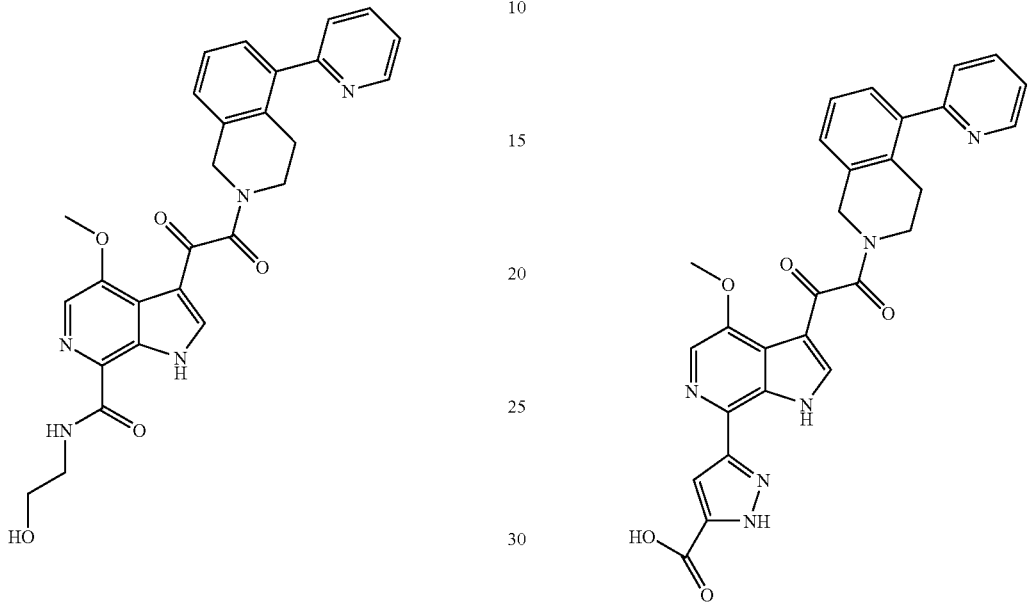

Preparation of N-(2-hydroxyethyl)-4-methoxy-3-(2-oxo-2-(5-(pyridin-2-yl)-3,4-dihydroisoquinolin-2(1H)-yl)acetyl)-1H-pyrrolo[2,3-c]pyridine-7-carboxamide, TFA, Compound 6

To a stainless steel pressure vessel containing 1-(7-bromo-4-methoxy-1H-pyrrolo[2,3-c]pyridin-3-yl)-2-(5-(pyridin-2-yl)-3,4-dihydroisoquinolin-2(1H)-yl)ethane-1,2-dione (0.2 g, 0.407 mmol) was added 1,4-dioxane (5 mL), water (0.037 mL, 2.035 mmol), tetrakis(triphenylphosphine)palladium(0) (0.071 g, 0.061 mmol), triethylamine (0.567 mL, 4.07 mmol), and ethanolamine (0.074 mL, 1.221 mmol). The vessel was sealed and was purged with N$_2$ three times. The vessel was filled with carbon monoxide to 50 psi, and purged 2 times, then finally was filled to 80 psi of carbon monoxide. The vessel was heated to 80° C. for 16 h then was cooled to rt. The mixture was transferred to a rb flask and the solvent was removed under reduced pressure. The residue was diluted with 5 mL of 1N HCl and was heated to 60° C. for 1.5 h. The mixture was filtered though a pad of CELITE® and washed with MeOH, then stripped of solvent under reduced pressure. The residue was dissolved in DMF and purified by prep HPLC. Fractions containing the expected product were concentrated under reduced pressure. The residue was diluted with sat. NaHCO$_3$ (10 mL) and extracted with dichloromethane (3×10 mL). The combined organic layers were dried with MgSO$_4$, the drying agent was removed by filtration, and the solution was concentrated under reduced pressure to give N-(2-hydroxyethyl)-4-methoxy-3-(2-oxo-2-(5-(pyridin-2-yl)-3,4-dihydroisoquinolin-2(1H)-yl)acetyl)-1H-pyrrolo[2,3-c]pyridine-7-carboxamide, TFA (0.05 g, 0.077 mmol, 19.02% yield) as an off-white solid. LC/MS: m/z 500.05 (M+H)+, 0.837 min (method 2). $^1$H NMR (500 MHz, DMSO-d$_6$) δ ppm 12.45-12.58 (m, 1H) 8.58-8.74 (m, 2H) 7.84-8.19 (m, 3H) 7.17-7.61 (m, 5H) 4.61-4.92 (m, 2H) 3.81-3.94 (m, 3H) 3.37-3.77 (m, 7H) 2.78-3.03 (m, 2H).

Preparation of 3-(4-methoxy-3-(2-oxo-2-(5-(pyridin-2-yl)-3,4-dihydroisoquinolin-2(1H)-yl)acetyl)-1H-pyrrolo[2,3-c]pyridin-7-yl)-1H-pyrazole-5-carboxylic acid, TFA, Compound 7

To a round bottom flask containing ethyl 3-(4-methoxy-3-(2-oxo-2-(5-(pyridin-2-yl)-3,4-dihydroisoquinolin-2(1H)-yl)acetyl)-1H-pyrrolo[2,3-c]pyridin-7-yl)-1H-pyrazole-5-carboxylate (0.623 g, 1.132 mmol) was added methanol (7 mL) and water (7 mL) followed by K$_2$CO$_3$ (0.782 g, 5.66 mmol). The mixture was heated to 60° C. After 2 h of heating, the mixture was cooled to rt, and acidified to pH=1 by adding 1N HCl. The solvent was removed under reduced pressure, and the crude residue was divided into 4 equal fractions. Three of these fractions were carried forward with no further purification to subsequent synthetic steps. The final fraction was diluted with warm DMF and passed through a plug of glass wool to remove the solids. The DMF solution was purified by prep HPLC. 55 mg of the expected product, 3-(4-methoxy-3-(2-oxo-2-(5-(pyridin-2-yl)-3,4-dihydroisoquinolin-2(1H)-yl)acetyl)-1H-pyrrolo[2,3-c]pyridin-7-yl)-1H-pyrazole-5-carboxylic acid, TFA, was isolated as a white solid. LC/MS: m/z 523.03 (M+H)+, 0.830 min (method 2). $^1$H NMR (500 MHz, DMSO-d$_6$) δ ppm 12.44 (br. s., 1H) 8.65-8.80 (m, 1H) 8.31-8.40 (m, 1H) 7.98-8.13 (m, 2H) 7.22-7.74 (m, 6H) 4.66-4.95 (m, 2H) 3.81-3.89 (m, 3H) 3.56-3.79 (m, 2H) 2.81-3.04 (m, 2H).

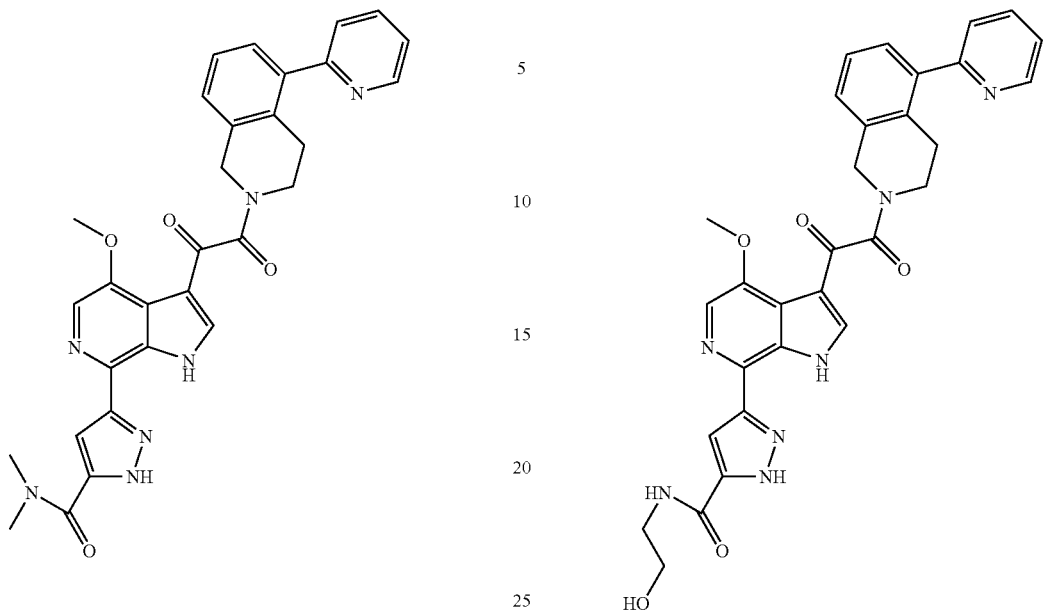

Preparation of 3-(4-methoxy-3-(2-oxo-2-(5-(pyridin-2-yl)-3,4-dihydroisoquinolin-2(1H)-yl)acetyl)-1H-pyrrolo[2,3-c]pyridin-7-yl)-N,N-dimethyl-1H-pyrazole-5-carboxamide, TFA, Compound 8

To a suspension of 3-(4-methoxy-3-(2-oxo-2-(5-(pyridin-2-yl)-3,4-dihydroisoquinolin-2(1H)-yl)acetyl)-1H-pyrrolo[2,3-c]pyridin-7-yl)-1H-pyrazole-5-carboxylic acid (146 mg, 0.28 mmol) in DMF (5 mL) was added Hunig's Base (0.489 mL, 2.80 mmol) followed by TBTU (117 mg, 0.364 mmol) and finally dimethylamine (2M in THF) (0.420 mL, 0.840 mmol). The mixture was stirred at rt in a sealed vial for 6 h. The mixture was quenched with water (3 mL) and the solvent was removed under reduced pressure. The residue was diluted with water and the solids that formed were collected by filtration and were washed with water and Et$_2$O. The solids were dissolved in DMF and passed through a plug of glass wool. The DMF solution was purified by prep HPLC. The fractions containing the expected product were concentrated under reduced pressure, then were further purified by prep HPLC. The product, 3-(4-methoxy-3-(2-oxo-2-(5-(pyridin-2-yl)-3,4-dihydroisoquinolin-2(1H)-yl)acetyl)-1H-pyrrolo[2,3-c]pyridin-7-yl)-N,N-dimethyl-1H-pyrazole-5-carboxamide, TFA (65.9 mg, 0.094 mmol, 33.7% yield), was isolated as an off-white solid. LC/MS: m/z 550.17 (M+H)$^+$, 1.565 min (method 1). $^1$H NMR (500 MHz, DMSO-d$_6$) δ ppm 12.36 (br. s., 1H) 8.68 (br. s., 1H) 8.34 (s, 1H) 7.92-8.11 (m, 2H) 7.20-7.71 (m, 7H) 4.64-4.93 (m, 2H) 3.80-3.89 (m, 3H) 3.57-3.79 (m, 2H) 3.29 (s, 3 H) 3.07 (s, 3H) 2.81-3.03 (m, 2H).

Preparation of N-(2-hydroxyethyl)-3-(4-methoxy-3-(2-oxo-2-(5-(pyridin-2-yl)-3,4-dihydroisoquinolin-2(1H)-yl)acetyl)-1H-pyrrolo[2,3-c]pyridin-7-yl)-1H-pyrazole-5-carboxamide, TFA, Compound 9

To a suspension of 3-(4-methoxy-3-(2-oxo-2-(5-(pyridin-2-yl)-3,4-dihydroisoquinolin-2(1H)-yl)acetyl)-1H-pyrrolo[2,3-c]pyridin-7-yl)-1H-pyrazole-5-carboxylic acid (146 mg, 0.28 mmol) in DMF (5 mL) was added Hunig's Base (0.489 mL, 2.80 mmol) followed by TBTU (117 mg, 0.364 mmol) and finally ethanolamine (0.025 mL, 0.420 mmol). The mixture was stirred at rt in a sealed vial for 6 h. The mixture was quenched with water (3 mL) and the solvent was removed under reduced pressure. The residue was diluted with water and the solids that formed were collected by filtration and were washed with water and Et$_2$O. The solids were dissolved in DMF and passed through a plug of glass wool. The DMF solution was purified by prep HPLC. The fractions containing the expected product were combined and concentrated under reduced pressure. The residue was purified further by prep HPLC. The expected product, N-(2-hydroxyethyl)-3-(4-methoxy-3-(2-oxo-2-(5-(pyridin-2-yl)-3,4-dihydroisoquinolin-2(1H)-yl)acetyl)-1H-pyrrolo[2,3-c]pyridin-7-yl)-1H-pyrazole-5-carboxamide, TFA (50.4 mg, 0.070 mmol, 25.2% yield), was isolated as an off-white solid. LC/MS: m/z 566.14 (M+H)$^+$, 1.427 min (method 1). $^1$H NMR (500 MHz, DMSO-d$_6$) δ ppm 12.25 (br. s., 1H) 8.65-8.78 (m, 1H) 8.56 (br. s., 1H) 8.24-8.33 (m, 1H) 7.94-8.11 (m, 2H) 7.22-7.73 (m, 6H) 4.63-4.95 (m, 2H) 3.80-3.87 (m, 3H) 3.30-3.79 (m, 6H) 2.79-3.05 (m, 2H).

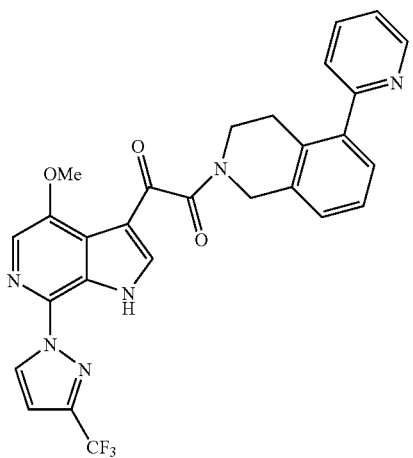

Preparation of 1-(4-methoxy-7-(3-(trifluoromethyl)-1H-pyrazol-1-yl)-1H-pyrrolo[2,3-c]pyridin-3-yl)-2-(5-(pyridin-2-yl)-3,4-dihydroisoquinolin-2(1H)-yl)ethane-1,2-dione, Compound 10

A mixture of 1-(7-bromo-4-methoxy-1H-pyrrolo[2,3-c]pyridin-3-yl)-2-(5-(pyridin-2-yl)-3,4-dihydroisoquinolin-2(1H)-yl)ethane-1,2-dione (100 mg, 0.204 mmol), 3-(trifluoromethyl)-1H-pyrazole (55.4 mg, 0.407 mmol), (1R,2S)—N1,N2-dimethylcyclohexane-1,2-diamine (5.79 mg, 0.041 mmol), copper(I) iodide (19.38 mg, 0.102 mmol) and potassium carbonate (84 mg, 0.611 mmol) in dioxane (1 mL) was heated up at 100° C. for 36 hours. LCMS indicated desired product was formed. The reaction mixture was filtered and the clear solution was dissolved in methanol and purified by prep. HPLC to give 1-(4-methoxy-7-(3-(trifluoromethyl)-1H-pyrazol-1-yl)-1H-pyrrolo[2,3-c]pyridin-3-yl)-2-(5-(pyridin-2-yl)-3,4-dihydroisoquinolin-2(1H)-yl)ethane-1,2-dione as white solid (37 mg, 32%). LCMS: m/e 547.05 (M+H)$^+$, 2.17 min (method 9). $^1$H NMR (500 MHz, MeOD) δ ppm 2.85-3.09 (m, 2H) 3.74-3.99 (m, 5H) 4.84 (s, 1H) 5.04 (s, 1H) 6.94 (d, J=2.44 Hz, 1H) 7.36-7.67 (m, 3H) 7.80-7.88 (m, 1H) 7.97-8.16 (m, 2H) 8.31-8.40 (m, 1H) 8.52-8.67 (m, 1H) 8.79 (s, 1H) 8.84-8.96 (m, 1H).

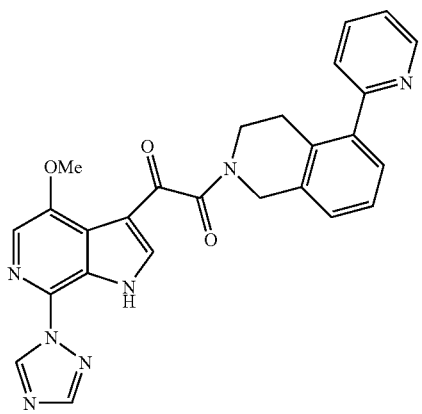

Preparation of 1-(4-methoxy-7-(1H-1,2,4-triazol-1-yl)-1H-pyrrolo[2,3-c]pyridin-3-yl)-2-(5-(pyridin-2-yl)-3,4-dihydroisoquinolin-2(1H)-yl)ethane-1,2-dione, Compound 11

A mixture of 1-(7-bromo-4-methoxy-1H-pyrrolo[2,3-c]pyridin-3-yl)-2-(5-(pyridin-2-yl)-3,4-dihydroisoquinolin-2(1H)-yl)ethane-1,2-dione (80 mg, 0.163 mmol), 1H-1,2,4-triazole (45.0 mg, 0.651 mmol) and copper (20.69 mg, 0.326 mmol) in pyridine (1 mL) was heated at 145° C. for 10 hours, LCMS indicated the formation of desired product. The reaction mixture was filtered and the clear solution purified by prep. HPLC to give 1-(4-methoxy-7-(1H-1,2,4-triazol-1-yl)-1H-pyrrolo[2,3-c]pyridin-3-yl)-2-(5-(pyridin-2-yl)-3,4-dihydroisoquinolin-2(1H)-yl)ethane-1,2-dione as pale yellow solid (28 mg, 35%). LCMS: m/e 480.11 (M+H)$^+$, 1.52 min (method 9). $^1$H NMR (500 MHz, MeOD) δ ppm 2.81-3.10 (m, 2H) 3.70-4.04 (m, 5H) 4.76-5.10 (m, 2H) 7.37-7.72 (m, 3H) 7.80-7.93 (m, 1H) 8.00-8.22 (m, 2H) 8.30-8.42 (m, 2H) 8.55-8.75 (m, 1H) 8.83-8.99 (m, 1H) 9.39 (s, 1H).

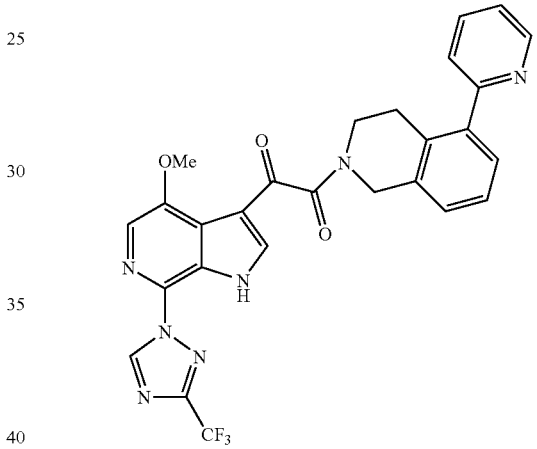

Preparation of 1-(4-methoxy-7-(3-(trifluoromethyl)-1H-1,2,4-triazol-1-yl)-1H-pyrrolo[2,3-c]pyridin-3-yl)-2-(5-(pyridin-2-yl)-3,4-dihydroisoquinolin-2(1H)-yl)ethane-1,2-dione, Compound 12

A mixture of 1-(7-bromo-4-methoxy-1H-pyrrolo[2,3-c]pyridin-3-yl)-2-(5-(pyridin-2-yl)-3,4-dihydroisoquinolin-2(1H)-yl)ethane-1,2-dione (100 mg, 0.204 mmol), 3-(trifluoromethyl)-1H-1,2,4-triazole (55.8 mg, 0.407 mmol), (1R,2S)—N1,N2-dimethylcyclohexane-1,2-diamine (5.79 mg, 0.041 mmol), copper (I) iodide (19.38 mg, 0.102 mmol) and potassium carbonate (84 mg, 0.611 mmol) in dioxane (1 mL) was heated at 100° C. for 4 hours. LCMS indicated that the desired product was generated. The reaction mixture was filtered and the clear solution was purified by prep. HPLC to give 1-(4-methoxy-7-(3-(trifluoromethyl)-1H-1,2,4-triazol-1-yl)-1H-pyrrolo[2,3-c]pyridin-3-yl)-2-(5-(pyridin-2-yl)-3,4-dihydroisoquinolin-2(1H)-yl)ethane-1,2-dione as white solid (35 mg, 30%). LCMS: m/e 548.18 (M+H)$^+$, 2.50 min (method 10). $^1$H NMR (500 MHz, MeOD) δ ppm 2.85-3.08 (m, 2H) 3.74-4.04 (m, 5H) 4.81-5.09 (m, 2H) 7.37-7.71 (m, 3H) 7.88-7.96 (m, 1H) 7.97-8.18 (m, 2H) 8.33-8.43 (m, 1H) 8.52-8.70 (m, 1H) 8.82-8.96 (m, 1H) 9.51 (s, 1H).

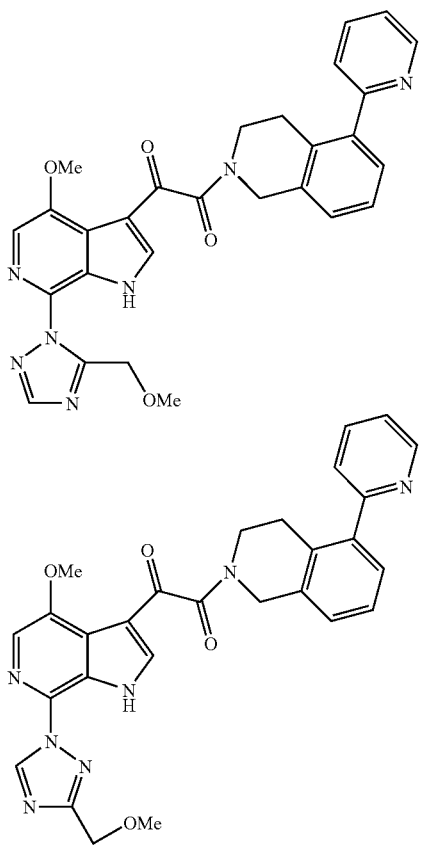

Preparation of 1-(4-methoxy-7-(5-(methoxymethyl)-1H-1,2,4-triazol-1-yl)-1H-pyrrolo[2,3-c]pyridin-3-yl)-2-(5-(pyridin-2-yl)-3,4-dihydroisoquinolin-2(1H)-yl)ethane-1,2-dione, compound 13 and 1-(4-methoxy-7-(3-(methoxymethyl)-1H-1,2,4-triazol-1-yl)-1H-pyrrolo[2,3-c]pyridin-3-yl)-2-(5-(pyridin-2-yl)-3,4-dihydroisoquinolin-2(1H)-yl)ethane-1,2-dione, Compound 14

A mixture of 1-(7-bromo-4-methoxy-1H-pyrrolo[2,3-c]pyridin-3-yl)-2-(5-(pyridin-2-yl)-3,4-dihydroisoquinolin-2(1H)-yl)ethane-1,2-dione (150 mg, 0.305 mmol), 3-(methoxymethyl)-1H-1,2,4-triazole (69.1 mg, 0.611 mmol) and copper (38.8 mg, 0.611 mmol) in pyridine (1 mL) was heated at 145° C. for 4 hours. LCMS indicated the formation of the desired product. The reaction mixture was filtered and the clear solution was purified by prep. HPLC to give 1-(4-methoxy-7-(5-(methoxymethyl)-1H-1,2,4-triazol-1-yl)-1H-pyrrolo[2,3-c]pyridin-3-yl)-2-(5-(pyridin-2-yl)-3,4-dihydroisoquinolin-2(1H)-yl)ethane-1,2-dione as white solid (24.2 mg, 14%). LCMS: m/e 524.09 (M+H)+, 1.31 min (method 2). 1H NMR (500 MHz, MeOD) δ ppm 2.82-3.08 (m, 2H) 3.48 (s, 3H) 3.72-4.03 (m, 5H) 4.80-5.06 (m, 2H) 5.11 (s, 2H) 7.36-7.69 (m, 3H) 7.88-7.96 (m, 1H) 7.98-8.19 (m, 2H) 8.25-8.39 (m, J=4.27 Hz, 2H) 8.55-8.69 (m, 1H) 8.84-8.95 (m, 1H) and 1-(4-methoxy-7-(3-(methoxymethyl)-1H-1,2,4-triazol-1-yl)-1H-pyrrolo[2,3-c]pyridin-3-yl)-2-(5-(pyridin-2-yl)-3,4-dihydroisoquinolin-2(1H)-yl)ethane-1,2-dione as white solid (34.7 mg, 21%). LCMS: m/e 524.04 (M+H)+, 1.63 min (method 9). 1H NMR (500 MHz, MeOD) δ ppm 2.85-3.10 (m, 2H) 3.47-3.63 (m, 3H) 3.70-4.05 (m, 5H) 4.69-5.10 (m, 4H) 7.29-7.68 (m, 3H) 7.81-8.05 (m, 3H) 8.32-8.53 (m, 2H) 8.74-8.92 (m, 1H) 9.31-9.42 (m, 1H).

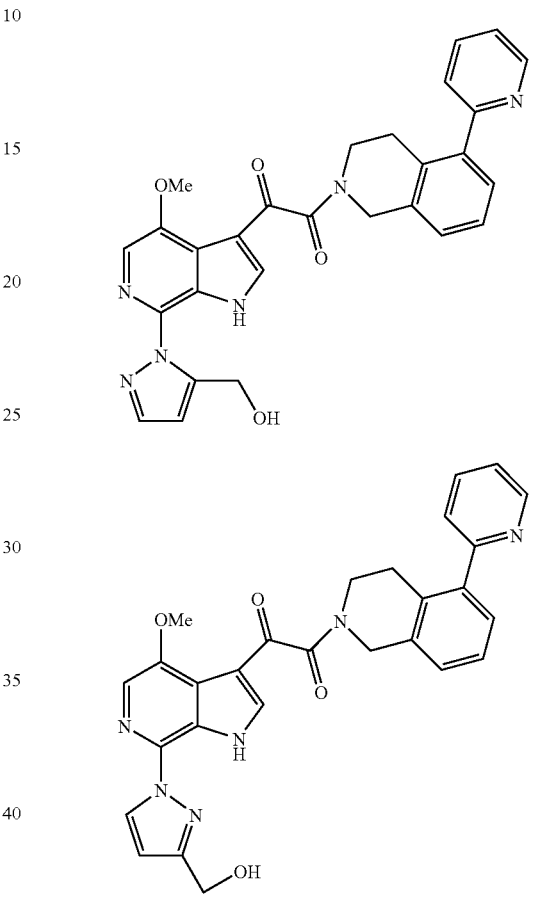

Preparation of 1-(7-(5-(hydroxymethyl)-1H-pyrazol-1-yl)-4-methoxy-1H-pyrrolo[2,3-c]pyridin-3-yl)-2-(5-(pyridin-2-yl)-3,4-dihydroisoquinolin-2(1H)-yl)ethane-1,2-dione, Compound 15 and 1-(7-(3-(hydroxymethyl)-1H-pyrazol-1-yl)-4-methoxy-1H-pyrrolo[2,3-c]pyridin-3-yl)-2-(5-(pyridin-2-yl)-3,4-dihydroisoquinolin-2(1H)-yl)ethane-1,2-dione, Compound 16

A mixture of 1-(7-bromo-4-methoxy-1H-pyrrolo[2,3-c]pyridin-3-yl)-2-(5-(pyridin-2-yl)-3,4-dihydroisoquinolin-2(1H)-yl)ethane-1,2-dione (50 mg, 0.102 mmol), (1H-pyrazol-3-yl)methanol (19.97 mg, 0.204 mmol), (1R,2S)—N1,N2-dimethylcyclohexane-1,2-diamine (2.89 mg, 0.020 mmol), copper (I) iodide (9.69 mg, 0.051 mmol) and potassium carbonate (42.2 mg, 0.305 mmol) in dioxane (1 mL) was heated at 100° C. for 18 hours. LCMS indicated that the desired product was generated. The reaction mixture was filtered and the clear solution was purified by prep. HPLC to give 1-(7-(5-(hydroxymethyl)-1H-pyrazol-1-yl)-4-methoxy-1H-pyrrolo[2,3-c]pyridin-3-yl)-2-(5-(pyridin-2-yl)-3,4-dihydroisoquinolin-2(1H)-yl)ethane-1,2-dione as colorless oil (3.1 mg, 6%). LCMS: m/e 509.04 (M+H)+, 1.13 min (method 2). ¹H NMR (500 MHz, MeOD) δ ppm 2.82-3.05 (m, 2H) 3.70-3.97 (m, 5H) 4.74-5.07 (m, 4H) 6.53-6.64 (m, 1H) 7.31-7.66 (m, 3H) 7.74-7.90 (m, 2H) 7.92-8.14 (m, 2H) 8.26-8.37 (m, 1H) 8.49-8.64 (m, 1H) 8.80-8.94 (m, 1H) and 1-(7-(3-(hydroxymethyl)-1H-pyrazol-1-yl)-4-methoxy-1H-pyrrolo[2,3-c]pyridin-3-yl)-2-(5-(pyridin-2-yl)-3,4-dihydroisoquinolin-2(1H)-yl)ethane-1,2-dione as colorless oil (3.7 mg, 7%). LCMS: m/e 509.04 (M+H)+, 1.13 min (method 2). ¹H NMR (500 MHz, MeOD) δ ppm 2.83-3.05 (m, 2H) 3.68-3.95 (m, 5H) 4.71-5.11 (m, 4H) 6.55 (d, J=2.75 Hz, 1H) 7.49 (d, J=36.66 Hz, 3H) 7.73-7.81 (m, 1H) 8.00 (s, 2H) 8.29-8.38 (m, 1H) 8.57 (t, J=2.64 Hz, 2H) 8.77-8.90 (m, 1H).

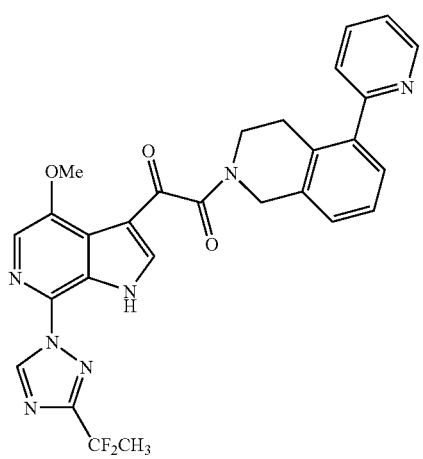

Preparation of 1-(7-(3-(1,1-difluoroethyl)-1H-1,2,4-triazol-1-yl)-4-methoxy-1H-pyrrolo[2,3-c]pyridin-3-yl)-2-(5-(pyridin-2-yl)-3,4-dihydroisoquinolin-2(1H)-yl)ethane-1,2-dione, Compound 17

A mixture of 1-(7-bromo-4-methoxy-1H-pyrrolo[2,3-c]pyridin-3-yl)-2-(5-(pyridin-2-yl)-3,4-dihydroisoquinolin-2(1H)-yl)ethane-1,2-dione (100 mg, 0.204 mmol), 3-(1,1-difluoroethyl)-1H-1,2,4-triazole (54.2 mg, 0.407 mmol), (1R,2S)-N1,N2-dimethylcyclohexane-1,2-diamine (5.79 mg, 0.041 mmol), K₂CO₃ (84 mg, 0.611 mmol) and copper (I) iodide (19.38 mg, 0.102 mmol) in dioxane (1 mL) was heated at 100° C. for 8 hours. LCMS indicated the formation of desired product. The reaction mixture was filtered and the clear solution purified by prep. HPLC to give 1-(7-(3-(1,1-difluoroethyl)-1H-1,2,4-triazol-1-yl)-4-methoxy-1H-pyrrolo[2,3-c]pyridin-3-yl)-2-(5-(pyridin-2-yl)-3,4-dihydroisoquinolin-2(1H)-yl)ethane-1,2-dione as white solid (53.4 mg, 47%). LCMS: m/e 543.97 (M+H)+, 1.56 min (method 2). ¹H NMR (500 MHz, MeOD) δ ppm 2.13-2.33 (m, 3H) 2.85-3.09 (m, 2H) 3.72-4.04 (m, 5H) 4.93-5.11 (m, 2H) 7.30-7.67 (m, 3H) 7.82-8.08 (m, 3H) 8.33-8.57 (m, 2H) 8.75-8.93 (m, 1H) 9.43 (s, 1H).

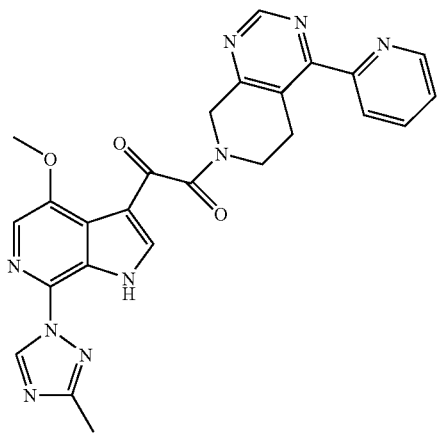

Preparation of 1-(4-methoxy-7-(3-methyl-1H-1,2,4-triazol-1-yl)-1H-pyrrolo[2,3-c]pyridin-3-yl)-2-(4-(pyridin-2-yl)-5,6-dihydropyrido[3,4-d]pyrimidin-7(8H)-yl)ethane-1,2-dione, Compound 18

Part A: To a solution of sodium methoxide (25 wgt-% in methanol) (67.6 mL, 296 mmol) and methanol (70 mL) at 25° C. was added formamidine acetate (11.00 g, 106 mmol) and then ethyl N-benzyl-3-oxo-4-piperidine carboxylate hydrochloride (25.16 g, 84 mmol). The resulting mixture was stirred at 25° C. for 20 h. The mixture was cooled to 0° C. Water (90 mL) was added, followed by the dropwise addition of acetic acid (6.05 mL, 106 mmol), and the reaction mixture was stirred at 25° C. for another 3 h. The mixture was reduced in volume under vacuum until most of the methanol had been removed. The suspension was filtered. The solids were washed with water and then dried under vacuum to afford 7-benzyl-5,6,7,8-tetrahydropyrido[3,4-d]pyrimidin-4(3H)-one (16.10 g, 79%) as an off-white solid; Mass Spec.: m/e: 242.06 (M+H)+ [calc'd: 242.12]; ¹H NMR (500 MHz, CDCl₃) δ 12.61 (br s, 1H), 7.99 (s, 1H), 7.38-7.26 (m, 5H), 3.73 (m, 2H), 3.50 (m, 2H), 2.74 (m, 2H), 2.66 (m, 2H).

Part B: To a mixture of 7-benzyl-5,6,7,8-tetrahydropyrido[3,4-d]pyrimidin-4(3H)-one 4.83 g, 20.0 mmol) in toluene (80 mL) at 25° C. was added N,N-diisopropylethylamine (3.48 mL, 20.0 mmol), followed by phosphorous oxychloride (2.24 mL, 24.0 mmol). The reaction mixture was heated at reflux for 2.00 h. After cooling to room temperature, the mixture was diluted with water and ethyl acetate. The aqueous phase was adjusted to ~pH 7 employing saturated aqueous sodium bicarbonate solution. The phases were separated. The organic phase was washed with water and brine, dried over anhyd. sodium sulfate, filtered, and concentrated. The residue was dissolved in 1-chlorobutane, and the resulting mixture was filtered. The filtrate was concentrated under vacuum to provide 7-benzyl-4-chloro-5,6,7,8-tetrahydropyrido[3,4-d]pyrimidine (4.75 g, 91%) as an orange-red oil; Mass Spec.: m/e: 260.10/262.05 (M+H)+ [calc'd: 260.09/262.08].

Part C: To a solution of 7-benzyl-4-chloro-5,6,7,8-tetrahydropyrido[3,4-d]pyrimidine (4.75 g, 18.3 mmol) in 1,4-dioxane (80 mL) at 25° C. was added sequentially 2-(tributylstannyl)pyridine (98%, 5.95 mL, 18.3 mmol), tri-2-furylphosphine (0.85 g, 3.66 mmol), and palladium (II) acetate (0.205 g, 0.914 mmol). The resulting mixture was heated slowly to reflux over ~0.25 h and then was stirred at reflux for 5.0 h. After cooling to room temperature the mixture was diluted with water and ethyl acetate, and the mixture filtered. The phases were separated, and the organic phase washed with water and brine, dried over anhyd. sodium sulfate, filtered, and concentrated. Column chromatography (elution: 0-5% 2M ammonia in methanol/chloroform) afforded 7-benzyl-4-(pyridin-2-yl)-5,6,7,8-tetrahydropyrido[3,4-d]pyrimidine (2.15 g, 39%) as a red oil; Mass Spec.: m/c: 303.15 (M+H)+ [calc'd: 303.15]; $^1$H NMR (500 MHz, CDCl$_3$) δ 9.02 (s, 1H), 8.68 (m, 1H), 8.01 (m, 1H), 7.83 (m, 1H), 7.42-7.27 (m, 6H), 3.80 (m, 4H), 3.31 (m, 2H), 2.80 (m, 2H).

Part D: To a solution of 7-benzyl-4-(pyridin-2-yl)-5,6,7,8-tetrahydropyrido[3,4-d]pyrimidine (2.15 g, 7.1 mmol) and N,N-diisopropylethylamine (2.48 mL, 14.2 mmol) in dichloromethane (30 mL) at 0° C. was added 1-chloroethyl chloroformate (1.15 mL, 10.7 mmol) over several minutes. The resulting solution was stirred at 0° C. for 1.0 h and then at 25° C. for 20 h. To this solution was added a saturated aqueous sodium bicarbonate solution (50 mL), and the resulting two-phase mixture was stirred at 25° C. for 1.0 h. The phases were separated, and the aqueous phase was washed with dichloromethane. The combined organic phases were dried over anhyd. sodium sulfate, filtered, and concentrated. The residue was dissolved in methanol, and the solution was heated at reflux for 1.0 h. After cooling to room temperature the mixture was concentrated under vacuum. The residue was triturated with ethyl acetate, and the resulting solids were recovered by filtration and dried under vacuum to provide a purple solid. These solids were dissolved in a mixture of concentrated aqueous sodium carbonate solution and chloroform. The phases were separated, and the aqueous phase was washed twice with chloroform. The combined organic phases were washed with brine, dried over anhyd. sodium sulfate, filtered, and concentrated. The residue was maintained under high vacuum overnight and then dissolved in methanol. This solution was filtered to remove a dark solid and then concentrated under vacuum. Finally, this residue was dissolved in 1,4-dioxane at 25° C. To this solution was added dropwise an excess (~1 mL) of 4N HCl in 1,4-dioxane. The resulting precipitate was recovered by filtration and dried under vacuum to furnish 4-(pyridin-2-yl)-5,6,7,8-tetrahydropyrido[3,4-d]pyrimidine hydrochloride (0.93 g, 53%) as a brick-red solid; Mass Spec.: m/e: 213.05 (M+H)+ [calc'd: 213.11]; $^1$HNMR (500 MHz, DMSO-d$_6$) δ 9.81 (br s, 2H), 9.17 (s, 1H), 8.76 (m, 1H), 8.15 (m, 1H), 7.59 (m, 1H), 4.49 (m, 2H), 3.41 (m, 4H).

Part E: To a solution of 4-(pyridin-2-yl)-5,6,7,8-tetrahydropyrido[3,4-d]pyrimidine hydrochloride (0.137 g, 0.55 mmol) in DMF (15 mL) at 25° C. was added sequentially 2-(4-methoxy-7-(3-methyl-1H-1,2,4-triazol-1-yl)-1H-pyrrolo[2,3-c]pyridin-3-yl)-2-oxoacetic acid (0.151 g, 0.50 mmol), N-methylmorpholine (0.220 mL, 2.00 mmol), and TBTU (0.177 g, 0.55 mmol), and the mixture was stirred at 25° C. for 18 h. The reaction mixture was concentrated under vacuum, and the residue dissolved in hot methanol. The solution was allowed to cool slowly to room temperature. The precipitate was recovered by filtration, washed with methanol, and dried under vacuum to provide 1-(4-methoxy-7-(3-methyl-1H-1,2,4-triazol-1-yl)-1H-pyrrolo[2,3-c]pyridin-3-yl)-2-(4-(pyridin-2-yl)-5,6-dihydropyrido[3,4-d]pyrimidin-7(8H)-yl)ethane-1,2-dione (0.122 g, 49%) as an off-white solid; HRMS: 496.1835 (M+H)+ [calc'd: 496.1840]; $^1$H NMR (500 MHz, DMSO-d$_6$) δ 12.44 (br s, 1H), 9.24 (m, 1H), 9.17 (s, 2/3H), 9.08 (s, 1/3H), 8.77 (m, 1/3H), 8.67 (m, 2/3H), 8.34 (s, 2/3H), 8.26 (s, 1/3H), 8.12-8.00 (m, 2H), 7.87 (m, 1H), 7.58 (m, 1/3H), 7.53 (m, 2/3H), 4.92 (s, 4/3H), 4.72 (s, 2/3H), 3.93 (m, 1/3H), 3.91 (s, 1H), 3.85 (s, 2H), 3.70 (m, 2/3H), 3.32 (m, 1/3H), 3.18 (m, 2/3H), 2.50 (s, 2H), 2.49 (s, 1H).

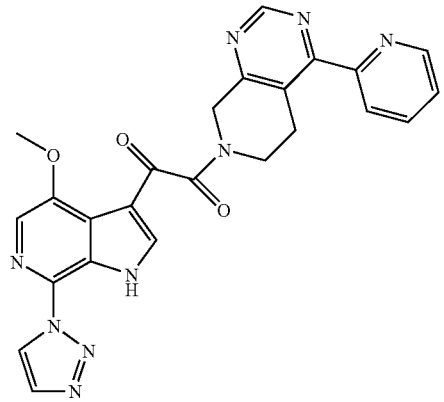

Preparation of 1-(4-methoxy-7-(1H-1,2,3-triazol-1-yl)-1H-pyrrolo[2,3-c]pyridin-3-yl)-2-(4-(pyridin-2-yl)-5,6-dihydropyrido[3,4-d]pyrimidin-7(8H)-yl)ethane-1,2-dione, Compound 19

The procedure described in Part E of preparation of compound 18 above was employed for the coupling of 4-(pyridin-2-yl)-5,6,7,8-tetrahydropyrido[3,4-d]pyrimidine hydrochloride with 2-(4-methoxy-7-(1H-1,2,3-triazol-1-yl)-1H-pyrrolo[2,3-c]pyridin-3-yl)-2-oxoacetic acid to afford 1-(4-methoxy-7-(1H-1,2,3-triazol-1-yl)-1H-pyrrolo[2,3-c]pyridin-3-yl)-2-(4-(pyridin-2-yl)-5,6-dihydropyrido[3,4-d]pyrimidin-7(8H)-yl)ethane-1,2-dione; HRMS: 486.1677 (M+H)+ [calc'd: 486.1684]; $^1$HNMR (500 MHz, DMSO-d$_6$) δ 12.82 (br s, 1H), 9.18 (s, 2/3H), 9.09 (s, 1/3H), 8.95 (s, 1H), 8.78 (m, 1/3H), 8.68 (m, 2/3H), 8.34 (s, 2/3H), 8.26 (s, 1/3H), 8.12-8.01 (m, 3H), 7.97 (s, 1H), 7.58 (m, 1/3H), 7.53 (m, 2/3H), 4.93 (s, 4/3H), 4.73 (s, 2/3H), 3.96 (s, 1H), 3.93 (m, 2/3H), 3.90 (s, 2H), 3.70 (m, 4/3H), 3.32 (m, 2/3), 3.18 (m, 4/3H).

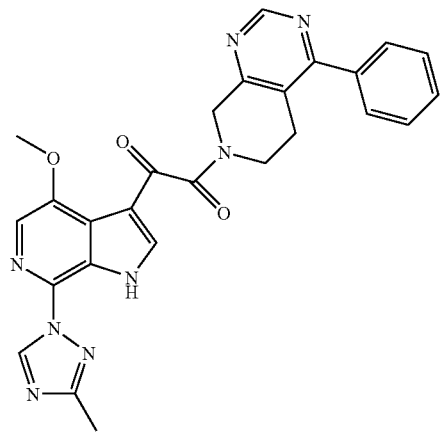

Preparation of 1-(4-methoxy-7-(3-methyl-1H-1,2,4-triazol-1-yl)-1H-pyrrolo[2,3-c]pyridin-3-yl)-2-(4-phenyl)-5,6-dihydropyrido[3,4-d]pyrimidin-7(8H)-yl)ethane-1,2-dione, Compound 20

The procedures described in Parts C, D, and E of preparation of compound 18 above were employed, with phenylboronic acid replacing 2-(tributylstannyl)pyridine, for the preparation of 1-(4-methoxy-7-(1H-1,2,3-triazol-1-yl)-1H-pyrrolo[2,3-c]pyridin-3-yl)-2-(4-phenyl)-5,6-dihydropyrido[3,4-d]pyrimidin-7(8H)-yl)ethane-1,2-dione; HRMS: 495.1879 (M+H)+ [calc'd: 495.1888]; 1H NMR (500 MHz, DMSO-$d_6$) δ 12.45 (br s, 1H), 9.25 (s, 1H), 9.14 (s, 2/3H), 9.05 (s, 1/3H), 8.34 (s, 2/3H), 8.29 (s, 1/3H), 7.88 (m, 1H), 7.72 (m, 2/3H), 7.64 (m, 4/3H), 7.57 (m, 1H), 7.52 (m, 2H), 4.89 (s, 4/3H), 4.70 (s, 2/3H), 3.94 (s, 1H), 3.90 (m, 2/3H), 3.87 (s, 2H), 3.67 (m, 4/3H), 3.04 (m, 2/3H), 2.89 (m, 4/3H), 2.50 (s, 3H).

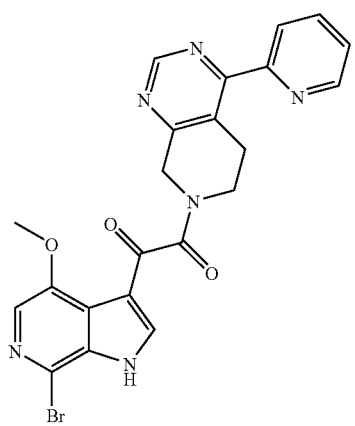

Preparation of 1-(7-bromo-4-methoxy-1H-pyrrolo[2,3-c]pyridin-3-yl)-2-(4-(pyridin-2-yl)-5,6-dihydropyrido[3,4-d]pyrimidin-7(8H)-yl)ethane-1,2-dione To a flask containing 2-(7-bromo-4-methoxy-1H-pyrrolo[2,3-c]pyridin-3-yl)-2-oxoacetic acid (0.264 g, 0.884 mmol) was added a solution of 4-(pyridin-2-yl)-5,6,7,8-tetrahydropyrido[3,4-d]pyrimidine, TFA (0.5 g, 1.149 mmol) in DMF (8 mL) followed by Hunig's Base (0.772 mL, 4.42 mmol) and finally TBTU (0.369 g, 1.149 mmol). After stirring the mixture at rt for 4 h, it was quenched with 10 mL of water and concentrated under reduced pressure. The residue was diluted with water (25 mL) and sat. aq. ammonium chloride (25 mL) added to the mixture. The mixture was extracted with dichloromethane (3×40 mL). The combined organic layers were washed with sat. aq. NaHCO$_3$, dried with MgSO$_4$, filtered and concentrated under reduced pressure. The residue was purified by BIOTAGE® flash chromatography using a 0-6% MeOH in dichloromethane gradient. The expected product, 1-(7-bromo-4-methoxy-1H-pyrrolo[2,3-c]pyridin-3-yl)-2-(4-(pyridin-2-yl)-5,6-dihydropyrido[3,4-d]pyrimidin-7(8H)-yl)ethane-1,2-dione (0.333 g, 0.675 mmol, 76% yield), was isolated as a brown solid. LC/MS: m/z 493 (M+H)+, 495.13 (M+3H)+, 2.177 min (method 3). 1H NMR (500 MHz, DMSO-$d_6$) δ ppm 13.11 (br. s., 1H) 9.05-9.19 (m, 1H) 8.66-8.78 (m, 1H) 8.33-8.44 (m, 1H) 7.99-8.12 (m, 2H) 7.82 (s, 1H) 7.50-7.60 (m, 1H) 4.66-4.91 (m, 2H) 3.63-3.92 (m, 5H) 3.11-3.32 (m, 2H).

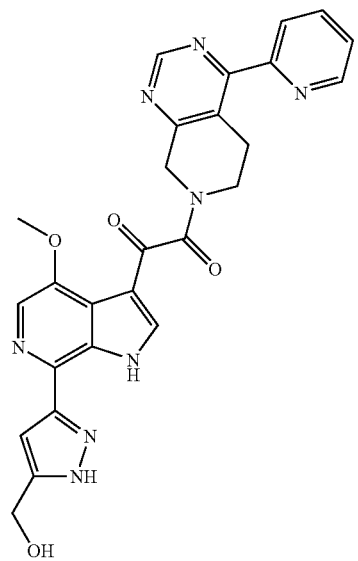

Preparation of 1-(7-(5-(hydroxymethyl)-1H-pyrazol-3-yl)-4-methoxy-1H-pyrrolo[2,3-c]pyridin-3-yl)-2-(4-(pyridin-2-yl)-5,6-dihydropyrido[3,4-d]pyrimidin-7(8H)-yl)ethane-1,2-dione, TFA, Compound 21

To a sealable vial containing 1-(7-bromo-4-methoxy-1H-pyrrolo[2,3-c]pyridin-3-yl)-2-(4-(pyridin-2-yl)-5,6-dihydropyrido[3,4-d]pyrimidin-7(8H)-yl)ethane-1,2-dione (0.14 g, 0.284 mmol) and (3-(tributylstannyl)-1H-pyrazol-5-yl)methanol (0.132 g, 0.341 mmol) was added tetrakis(triphenylphosphine)palladium (0) (0.066 g, 0.057 mmol) followed by dioxane (4 mL). The mixture was flushed with N$_2$, and the vial was sealed and heated to 110° C. After 3.5 h of heating, the mixture was cooled to rt. The solvent was removed under reduced pressure. The residue was diluted with DMF and was passed through a plug of glass wool to remove any solids. The DMF solution was purified by prep HPLC. The fractions containing the expected product were combined and concentrated under reduced pressure to give 1-(7-(5-(hydroxymethyl)-1H-pyrazol-3-yl)-4-methoxy-1H-pyrrolo[2,3-c]pyridin-3-yl)-2-(4-(pyridin-2-yl)-5,6-dihydropyrido[3,4-d]pyrimidin-7(8H)-yl)ethane-1,2-dione, TFA (86.4 mg, 0.136 mmol, 47.8% yield) as an off-white solid. LC/MS: m/z 511.17 (M+H)+, 1.212 min (method 1). 1H NMR (500 MHz, DMSO-$d_6$) δ ppm 12.75 (br. s., 1H) 9.06-9.20 (m, 1H) 8.65-8.80 (m, 1H) 8.46-8.55 (m, 1H) 7.97-8.16 (m, 3H) 7.50-7.62 (m, 1H) 7.08 (s, 1H) 4.93 (s, 2H) 4.74 (s, 1H) 4.64 (s, 2H) 3.67-4.00 (m, 5H) 3.15-3.36 (m, 2H).

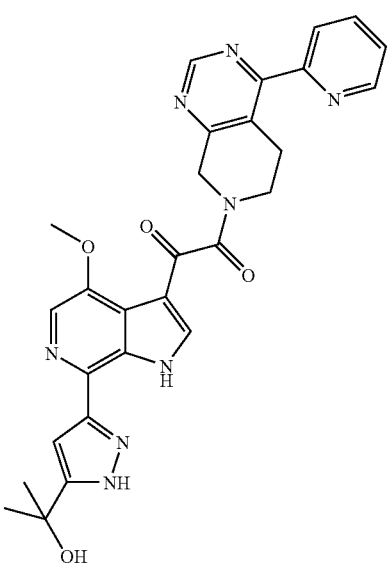

Preparation of 1-(7-(5-(2-hydroxypropan-2-yl)-1H-pyrazol-3-yl)-4-methoxy-1H-pyrrolo[2,3-c]pyridin-3-yl)-2-(4-(pyridin-2-yl)-5,6-dihydropyrido[3,4-d]pyrimidin-7(8H)-yl)ethane-1,2-dione, TFA, Compound 22

To a sealable vial containing 1-(7-bromo-4-methoxy-1H-pyrrolo[2,3-c]pyridin-3-yl)-2-(4-(pyridin-2-yl)-5,6-dihydropyrido[3,4-d]pyrimidin-7(8H)-yl)ethane-1,2-dione (0.14 g, 0.284 mmol) and 2-(3-(tributylstannyl)-1H-pyrazol-5-yl)propan-2-ol (0.141 g, 0.341 mmol) was added tetrakis(triphenylphosphine)palladium (0) (0.066 g, 0.057 mmol) followed by 1,4-dioxane (4 mL). The mixture was flushed with $N_2$, and the vial was sealed and heated to 110° C. After 3.5 h the mixture was cooled to rt and stripped of solvent under reduced pressure. The residue was diluted with DMF and passed through a plug of glass wool to remove any solids. The DMF solution was purified by prep HPLC. The fractions containing the product were combined and concentrated under reduced pressure. The expected product, 1-(7-(5-(2-hydroxypropan-2-yl)-1H-pyrazol-3-yl)-4-methoxy-1H-pyrrolo[2,3-c]pyridin-3-yl)-2-(4-(pyridin-2-yl)-5,6-dihydropyrido[3,4-d]pyrimidin-7(8H)-yl)ethane-1,2-dione, TFA (72.2 mg, 0.110 mmol, 38.6% yield) was isolated as a light-yellow solid. LC/MS: m/z 539.20 (M+H)$^+$, 1.312 min (method 1). $^1$H NMR (500 MHz, DMSO-$d_6$) δ ppm 12.70 (br. s., 1H) 9.07-9.20 (m, 1H) 8.65-8.79 (m, 1H) 8.49-8.58 (m, 1H) 8.00-8.14 (m, 3H) 7.50-7.61 (m, 1H) 7.02 (s, 1H) 4.72-4.96 (m, 2H) 3.68-3.99 (m, 5H) 3.16-3.35 (m, 2H) 1.57 (s, 6H).

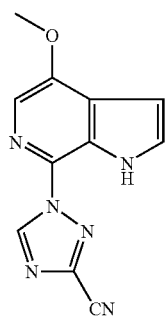

Preparation of 1-(4-methoxy-1H-pyrrolo[2,3-c]pyridin-7-yl)-1H-1,2,4-triazole-3-carbonitrile 7-Chloro-4-methoxy-1H-pyrrolo[2,3-c]pyridine (4 g, 21.90 mmol), 1H-1,2,4-triazole-3-carbonitrile (6.18 g, 65.7 mmol) and copper (I) iodide (1.252 g, 6.57 mmol) were combined in pyridine (6 mL) in a sealed tube. The mixture was heated to 150° C. for 6 hrs. After cooling to room temperature, the mixture was diluted with EtOAc (3000 mL), washed with 5% NaHCO$_3$ (100 mL), brine (100 mL) and concentrated. The residue was purified by silica gel column using 30% EtOAc in hexanes mixture to give 1-(4-methoxy-1H-pyrrolo[2,3-c]pyridin-7-yl)-1H-1,2,4-triazole-3-carbonitrile (2 g, 8.33 mmol, 38.0% yield). LCMS: m/z 241.1 (M+H), 1.67 min (method 8).

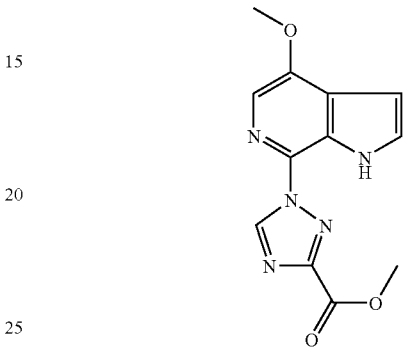

Preparation of methyl 1-(4-methoxy-1H-pyrrolo[2,3-c]pyridin-7-yl)-1H-1,2,4-triazole-3-carboxylate 1-(4-Methoxy-1H-pyrrolo[2,3-c]pyridin-7-yl)-1H-1,2,4-triazole-3-carbonitrile (1 g, 4.16 mmol) and K$_2$CO$_3$ (0.863 g, 6.24 mmol) were combined in MeOH (20 mL) and water (20 mL). The mixture was stirred at room temperature overnight. The mixture was neutralized with 1N HCl to pH=3. The precipitate was collected by filtration to give methyl 1-(4-methoxy-1H-pyrrolo[2,3-c]pyridin-7-yl)-1H-1,2,4-triazole-3-carboxylate (1.03 g, 3.77 mmol, 91% yield). LCMS: m/z 274.2 (M+H)$^+$, 1.63 min (method 8). $^1$H NMR (500 MHz, MeOD) d ppm 9.22 (s, 1H) 7.47 (s, 1H) 7.39 (d, J=3.05 Hz, 1H) 6.62 (d, J=3.05 Hz, 1H) 4.03 (s, 3H) 4.00 (s, 3H).

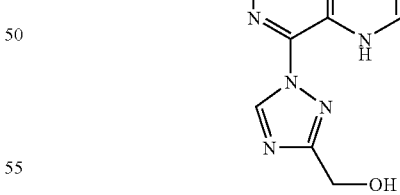

Preparation of (1-(4-methoxy-1H-pyrrolo[2,3-c]pyridin-7-yl)-1H-1,2,4-triazol-3-yl)methanol To a solution of methyl 1-(4-methoxy-1H-pyrrolo[2,3-c]pyridin-7-yl)-1H-1,2,4-triazole-3-carboxylate (220 mg, 0.805 mmol) in THF (20 mL) was added LiAlH$_4$ (1.208 mL, 2.415 mmol) dropwise over 5 min period at room temperature. The solution was refluxed for 1H and then cooled in an ice bath. The reaction mixture was quenched with water and extracted with EtOAc (3×100 ml). The organic layers were combined, washed with brine (30 ml), dried under MgSO₄ and concentrated. The residue was purified by prep. HPLC to give (1-(4-methoxy-1H-pyrrolo[2,3-c]pyridin-7-yl)-1H-1,2,4-triazol-3-yl)methanol (100 mg, 0.408 mmol, 50.6% yield). LCMS: m/z 246.2 (M+H)⁺, 1.36 min (method 8). ¹H NMR (500 MHz, MeOD) δ ppm 9.24 (s, 1H) 7.53 (s, 1H) 7.47 (d, J=3.05 Hz, 1H) 6.68 (d, J=2.75 Hz, 1H) 4.84 (s, 2H) 4.03 (s, 3H).

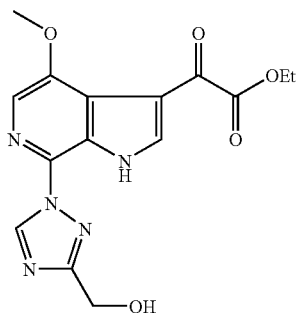

Preparation of ethyl 2-(7-(3-(hydroxymethyl)-1H-1,2,4-triazol-1-yl)-4-methoxy-1H-pyrrolo[2,3-c]pyridin-3-yl)-2-oxoacetate To a solution of (1-(4-methoxy-1H-pyrrolo[2,3-c]pyridin-7-yl)-1H-1,2,4-triazol-3-yl)methanol (70 mg, 0.285 mmol) in THF (5 mL) was added ethylmagnesium bromide (1.284 mL, 1.284 mmol) at −40° C. After stirring at −5° C. for 1H, pyridine (0.012 mL, 0.143 mmol) was added quickly. The mixture was cooled to −40° C. and ethyl 2-chloro-2-oxoacetate (0.130 mL, 1.142 mmol) was added. After stirring at −40° C. for 30 min, the reaction mixture was quenched by adding i-PrOH and water. The mixture was extracted with EtOAc (2×40 mL). The organic layers were combined, washed with brine (30 mL), dried over MgSO₄ and concentrated under vacuum to give crude product ethyl 2-(7-(3-(hydroxymethyl)-1H-1,2,4-triazol-1-yl)-4-methoxy-1H-pyrrolo[2,3-c]pyridin-3-yl)-2-oxoacetate (70 mg, 0.203 mmol, 71.0% yield). LCMS: m/z 346.1 (M+H)⁺, 1.42 min (method 8).

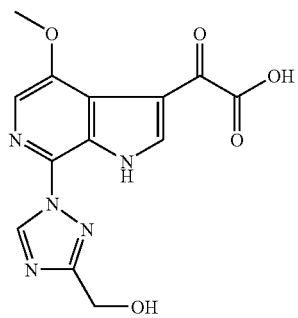

Preparation of 2-(7-(3-(hydroxymethyl)-1H-1,2,4-triazol-1-yl)-4-methoxy-1H-pyrrolo[2,3-c]pyridin-3-yl)-2-oxoacetic acid Ethyl 2-(7-(3-(hydroxymethyl)-1H-1,2,4-triazol-1-yl)-4-methoxy-1H-pyrrolo[2,3-c]pyridin-3-yl)-2-oxoacetate (70 mg, 0.203 mmol) and K₂CO₃ (56.0 mg, 0.405 mmol) were dissolved in MeOH (2 mL) and water (2.000 mL). The mixture was stirred at room temperature overnight, and neutralized with 1N HCl to pH 3. All solvents were removed under vacuum to give 2-(7-(3-(hydroxymethyl)-1H-1,2,4-triazol-1-yl)-4-methoxy-1H-pyrrolo[2,3-c]pyridin-3-yl)-2-oxoacetic acid. LCMS: m/z 318.2 (M+H)⁺, 1.04 min (method 8).

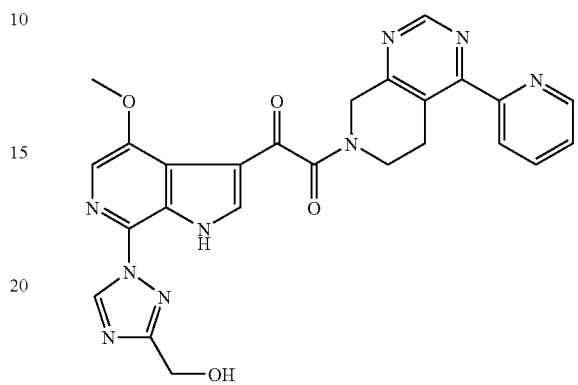

Preparation of 1-(7-(3-(hydroxymethyl)-1H-1,2,4-triazol-1-yl)-4-methoxy-1H-pyrrolo[2,3-c]pyridin-3-yl)-2-(4-(pyridin-2-yl)-5,6-dihydropyrido[3,4-d]pyrimidin-7(8H)-yl)ethane-1,2-dione, Compound 23

To a solution of 2-(7-(3-(hydroxymethyl)-1H-1,2,4-triazol-1-yl)-4-methoxy-1H-pyrrolo[2,3-c]pyridin-3-yl)-2-oxoacetic acid (23 mg, 0.072 mmol), 4-(pyridin-2-yl)-5,6,7,8-tetrahydropyrido[3,4-d]pyrimidine (15.39 mg, 0.072 mmol) and 2-(1H-benzotriazol-1-yl)-1,1,3,3-tetramethyluronium tetrafluoroborate (27.9 mg, 0.087 mmol) in DMF (1 mL) was added N,N-diisopropylethylamine (0.127 mL, 0.725 mmol). The mixture was stirred at room temperature for 2 hours, diluted with MeOH and purified by prep. HPLC to give 1-(7-(3-(hydroxymethyl)-1H-1,2,4-triazol-1-yl)-4-methoxy-1H-pyrrolo[2,3-c]pyridin-3-yl)-2-(4-(pyridin-2-yl)-5,6-dihydropyrido[3,4-d]pyrimidin-7(8H)-yl)ethane-1,2-dione (9 mg, 0.016 mmol, 22% yield). LCMS: m/z 512.2 (M+H)⁺, 1.34 min (method 8). ¹H NMR (500 MHz, DMSO-d₆) d ppm 12.39-12.48 (m, 1H) 9.30-9.33 (m, 1H) 9.06-9.16 (m, 1H) 8.64-8.76 (m, 1H) 8.29-8.39 (m, 1H) 7.98-8.10 (m, 2H) 7.87 (s, 1H) 7.49-7.58 (m, 1H) 4.70-4.92 (m, 2H) 4.65-4.67 (m, 2H) 3.83-3.90 (m, 3H) 3.68 (t, J=5.80 Hz, 2H) 3.16 (t, J=5.65 Hz, 2H).

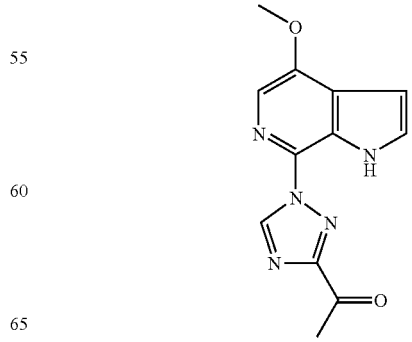

Preparation of 1-(1-(4-methoxy-1H-pyrrolo[2,3-c]pyridin-7-yl)-1H-1,2,4-triazol-3-yl)ethanone To a solution of 1-(4-methoxy-1H-pyrrolo[2,3-c]pyridin-7-yl)-1H-1,2,4-triazole-3-carbonitrile (500 mg, 2.081 mmol) in THF (50 mL) was added methylmagnesium bromide (2.081 mL, 6.24 mmol) dropwise at 0° C. After stirring at room temperature for 3 h, the reaction mixture was quenched with 0.5N H$_2$SO$_4$ (10 mL) and extracted with EtOAc (2×100 mL). The organic layers were combined, washed with brine (30 mL), dried and concentrated. The residue was purified via silica gel flash chromatography using 75% EtOAc in hexanes to give 1-(1-(4-methoxy-1H-pyrrolo[2,3-c]pyridin-7-yl)-1H-1,2,4-triazol-3-yl)ethanone (280 mg, 1.088 mmol, 52.3% yield). LCMS: m/z 258.1 (M+H)$^+$, 1.63 min (method 8). $^1$H NMR (500 MHz, chloroform-d) δ ppm 10.45 (s, 1H) 9.26 (s, 1H) 7.58 (s, 1H) 7.41 (t, J=2.59 Hz, 1H) 6.72-6.73 (m, 1H) 4.05 (s, 3H) 2.78 (s, 3H).

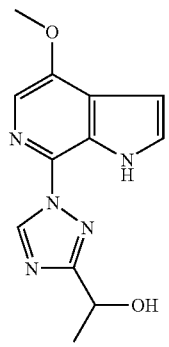

Preparation of 1-(1-(4-methoxy-1H-pyrrolo[2,3-c]pyridin-7-yl)-1H-1,2,4-triazol-3-yl)ethanol To a solution of 1-(1-(4-methoxy-1H-pyrrolo[2,3-c]pyridin-7-yl)-1H-1,2,4-triazol-3-yl)ethanone (50 mg, 0.194 mmol) in MeOH (3 mL) was added sodium borohydride (14.71 mg, 0.389 mmol) at 0° C. After stirring at room temperature for 3 h, the reaction was diluted with 5% NaHCO$_3$ (5 mL) and extracted with EtOAc (2×30 mL). The organic layers were combined and concentrated. The residue was purified by prep. HPLC to give 1-(1-(4-methoxy-1H-pyrrolo[2,3-c]pyridin-7-yl)-1H-1,2,4-triazol-3-yl)ethanol (29 mg, 0.112 mmol, 57.5% yield). LCMS: m/z 260.2 (M+H)$^+$, 1.47 min (method 8). $^1$H NMR (500 MHz, MeOD) δ ppm 9.17 (s, 1H) 7.51 (s, 1H) 7.45 (d, J=3.05 Hz, 1H) 6.67 (d, J=3.05 Hz, 1H) 5.09 (q, J=6.51 Hz, 1H) 4.02 (s, 3H) 1.63 (d, J=6.41 Hz, 3H).

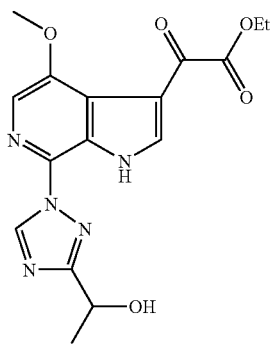

Preparation of ethyl 2-(7-(3-(1-hydroxyethyl)-1H-1,2,4-triazol-1-yl)-4-methoxy-1H-pyrrolo[2,3-c]pyridin-3-yl)-2-oxoacetate To a solution of 1-(1-(4-methoxy-1H-pyrrolo[2,3-c]pyridin-7-yl)-1H-1,2,4-triazol-3-yl)ethanol (100 mg, 0.386 mmol) in THF (8 mL) was added ethylmagnesium bromide (1.736 mL, 1.736 mmol) at −40° C. After stirring at −5° C. for 1 h, pyridine (0.016 mL, 0.193 mmol) was added quickly. The mixture was cooled to −40° C. and ethyl 2-chloro-2-oxoacetate (0.176 mL, 1.543 mmol) was added. After stirring at −40° C. for 30 min, the reaction was quenched by adding i-PrOH and water. The mixture was extracted with EtOAc (2×50 mL). The organic layers were combined, washed with brine (30 mL), dried over MgSO$_4$ and concentrated under vacuum to give crude product ethyl 2-(7-(3-(1-hydroxyethyl)-1H-1,2,4-triazol-1-yl)-4-methoxy-1H-pyrrolo[2,3-c]pyridin-3-yl)-2-oxoacetate (100 mg, 0.278 mmol, 72.2% yield). LCMS: m/z 360.1 (M+H)$^+$, 1.53 min (method 8).

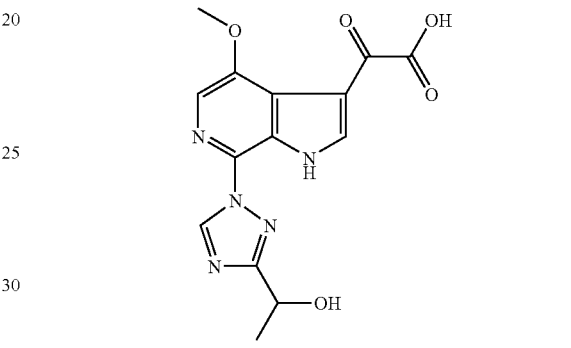

Preparation of 2-(7-(3-(1-hydroxyethyl)-1H-1,2,4-triazol-1-yl)-4-methoxy-1H-pyrrolo[2,3-c]pyridin-3-yl)-2-oxoacetic acid Ethyl 2-(7-(3-(1-hydroxyethyl)-1H-1,2,4-triazol-1-yl)-4-methoxy-1H-pyrrolo[2,3-c]pyridin-3-yl)-2-oxoacetate (100 mg, 0.278 mmol) and K$_2$CO$_3$ (77 mg, 0.557 mmol) were dissolved in MeOH (2 mL) and water (2 mL). The mixture was stirred at room temperature overnight, and neutralized with 1N HCl to pH 3. All solvents were removed and the residue was purified by prep. HPLC to give 2-(7-(3-(1-hydroxyethyl)-1H-1,2,4-triazol-1-yl)-4-methoxy-1H-pyrrolo[2,3-c]pyridin-3-yl)-2-oxoacetic acid (46 mg, 0.139 mmol, 49.9% yield). LCMS: m/z 332.1 (M+H)$^+$, 1.17 min (method 8).

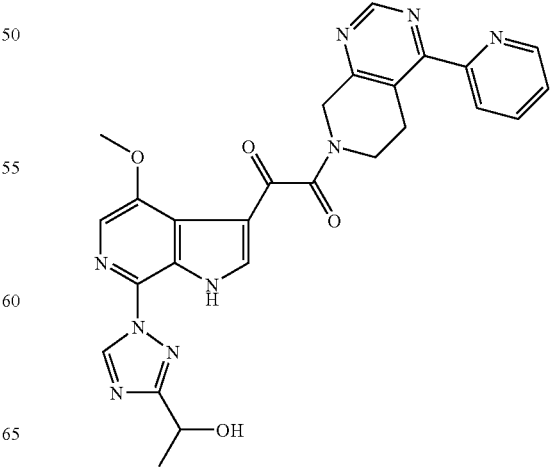

Preparation of 1-(7-(3-(1-hydroxyethyl)-1H-1,2,4-triazol-1-yl)-4-methoxy-1H-pyrrolo[2,3-c]pyridin-3-yl)-2-(4-(pyridin-2-yl)-5,6-dihydropyrido[3,4-d]pyrimidin-7(8H)-yl)ethane-1,2-dione, Compound 24

To a solution of 2-(7-(3-(1-hydroxyethyl)-1H-1,2,4-triazol-1-yl)-4-methoxy-1H-pyrrolo[2,3-c]pyridin-3-yl)-2-oxoacetic acid (18 mg, 0.054 mmol), 4-(pyridin-2-yl)-5,6,7,8-tetrahydropyrido[3,4-d]pyrimidine (1.53 mg, 0.054 mmol) and 2-(1H-benzotriazol-1-yl)-1,1,3,3-tetramethyluronium tetrafluoroborate (20.93 mg, 0.065 mmol) in DMF (1 mL) was added N,N-diisopropylethylamine (0.095 mL, 0.543 mmol). The mixture was stirred at room temperature for 2 hours, diluted with MeOH and purified by prep. HPLC to give 1-(7-(3-(1-hydroxyethyl)-1H-1,2,4-triazol-1-yl)-4-methoxy-1H-pyrrolo[2,3-c]pyridin-3-yl)-2-(4-(pyridin-2-yl)-5,6-dihydropyrido[3,4-d]pyrimidin-7(8H)-yl)ethane-1,2-dione (17 mg, 0.030 mmol, 54.8% yield). LCMS: m/z 526.2 (M+H)$^+$, 1.54 min (method 8). $^1$H NMR (500 MHz, MeOD) δ ppm 9.17 (s, 1H) 8.99-9.10 (m, 1H) 8.61-8.74 (m, 1H) 8.27-8.32 (m, 1H) 7.92-8.04 (m, 2H) 7.74-7.79 (m, 1H) 7.43-7.53 (m, 1H) 5.09 (q, J=6.41 Hz, 1H) 4.80-5.02 (m, 2H) 3.76-4.02 (m, 5H) 3.24-3.38 (m, 2H) 1.60-1.89 (m, 3H).

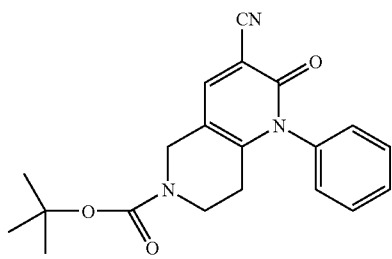

Preparation of tert-butyl 3-cyano-2-oxo-1-phenyl-1,2,7,8-tetrahydro-1,6-naphthyridine-6(5H)-carboxylate 2-Cyano-N-phenylacetamide (820 mg) in THF (20 mL) was treated with LDA (4.4 mL, 1.8M solution in heptane/THF/ethylbenzene) at −78° C. for 1 h, before (E)-tert-butyl-3-((dimethylamino)methylene)-4-oxopiperidine-1-carboxylate (1 g) was added. The reaction mixture was allowed to warm to room temperature, and quenched with saturated NaHCO$_3$ aqueous solution (20 mL). The aqueous solution was extracted with EtOAc (3×20 mL) and the combined organic layer was dried over MgSO$_4$. Concentration under vacuum provided a residue which was purified by HPLC to afford tert-butyl 3-cyano-2-oxo-1-phenyl-1,2,7,8-tetrahydro-1,6-naphthyridine-6(5H)-carboxylate. LCMS: m/z 352.2 (M+H)$^+$, 1.63 min (method 8). $^1$H NMR (500 MHz, DMSO-d$_6$) δ ppm 8.19 (s, 1H) 7.48-7.57 (m, 3H) 7.33 (d, J=7.02 Hz, 2H) 4.33 (s, 2H) 3.44 (t, J=5.65 Hz, 2H) 2.19 (t, J=5.80 Hz, 2H) 1.39 (s, 9H).

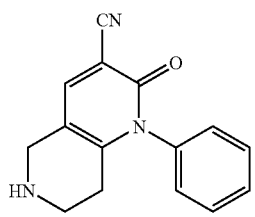

Preparation of 2-oxo-1-phenyl-1,2,5,6,7,8-hexahydro-1,6-naphthyridine-3-carbonitrile tert-Butyl 3-cyano-2-oxo-1-phenyl-1,2,7,8-tetrahydro-1,6-naphthyridine-6(5H)-carboxylate (150 mg, 0.427 mmol) was dissolved in CH$_2$Cl$_2$ (3 mL) and TFA (0.3 mL). The mixture was stirred at room temperature overnight. All solvents were removed under vacuum to give crude 2-oxo-1-phenyl-1,2,5,6,7,8-hexahydro-1,6-naphthyridine-3-carbonitrile. LCMS: m/z 252.15 (M+H)$^+$, 0.78 min (method 7).

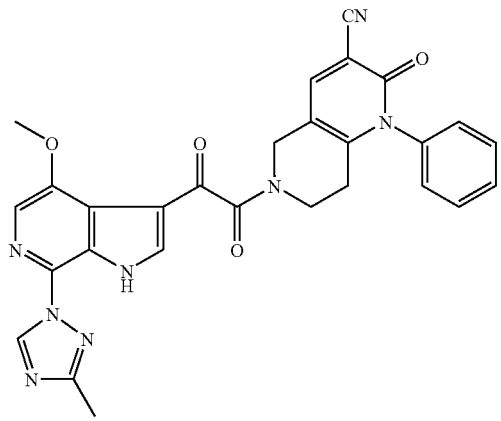

Preparation of 6-(2-(4-methoxy-7-(3-methyl-1H-1,2,4-triazol-1-yl)-1H-pyrrolo[2,3-c]pyridin-3-yl)-2-oxoacetyl)-2-oxo-1-phenyl-1,2,5,6,7,8-hexahydro-1,6-naphthyridine-3-carbonitrile, Compound 25

To a solution of 2-(4-methoxy-7-(3-methyl-1H-1,2,4-triazol-1-yl)-1H-pyrrolo[2,3-c]pyridin-3-yl)-2-oxoacetic acid (70 mg, 0.232 mmol), 2-oxo-1-phenyl-1,2,5,6,7,8-hexahydro-1,6-naphthyridine-3-carbonitrile (58.4 mg, 0.232 mmol) and 2-(1H-benzotriazol-1-yl)-1,1,3,3-tetramethyluronium tetrafluoroborate (90 mg, 0.279 mmol) in DMF (2 mL) was added N,N-diisopropylethylamine (0.406 mL, 2.324 mmol). The mixture was stirred at room temperature for 4 hours, and diluted with EtOAc (100 mL) and washed with 5% of NaHCO$_3$ (20 mL), and brine (20 mL). The organic layer was dried over MgSO$_4$ and concentrated under vacuum. The residue was purified by prep. HPLC and silica gel column (using EtOAc) to give 6-(2-(4-methoxy-7-(3-methyl-1H-1,2,4-triazol-1-yl)-1H-pyrrolo[2,3-c]pyridin-3-yl)-2-oxoacetyl)-2-oxo-1-phenyl-1,2,5,6,7,8-hexahydro-1,6-naphthyridine-3-carbonitrile (6.1 mg, 10.27 μmol, 4.42% yield). LCMS: m/z 535.09 (M+H)$^+$, 1.65 min (method 7). $^1$H NMR (500 MHz, chloroform-d) δ ppm 11.07 (s, 1H) 9.05-9.12 (m, 1H) 8.18-8.27 (m, 1H) 7.45-7.78 (m, 5H) 7.14-7.21 (m, 2H) 4.50-4.73 (m, 2H) 3.95-4.04 (m, 3H) 3.64-3.90 (m, 2H) 2.53-2.57 (m, 3H) 2.42-2.50 (m, 2H).

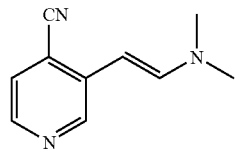

Preparation of (E)-3-(2-(dimethylamino)vinyl)isonicotinonitrile

To a solution of 3-methylisonicotinonitrile (10 g, 85 mmol) in DMF (100 mL) was added 1,1-dimethoxy-N,N-dimethylmethanamine (18.05 mL, 135 mmol). The mixture was heated to reflux overnight. The mixture was cooled to rt and an additional 3.0 mL of 1,1-dimethoxy-N,N-dimethylmethanamine was added to the mixture, and it was again heated to reflux. After heating the mixture overnight, it was cooled to rt and an additional 3.0 mL of 1,1-dimethoxy-N,N-dimethylmethanamine was added to the mixture. The mixture was heated overnight at reflux. The mixture was cooled to rt and an additional 3.0 mL of 1,1-dimethoxy-N,N-dimethylmethanamine were added. The mixture was again heated to reflux. After heating the mixture overnight, it was cooled to rt. To the mixture was added 3.0 mL of 1,1-dimethoxy-N,N-dimethylmethanamine. The mixture was heated to reflux overnight. The mixture was cooled to rt and was concentrated under reduced pressure. The residue was dissolved in dichloromethane and was loaded onto a BIOTAGE® 65+M cartridge and was purified using a 10-70% EtOAc in hexanes gradient. The expected product, (E)-3-(2-(dimethylamino)vinyl)isonicotinonitrile (7.97 g, 46.0 mmol, 54.4% yield), was isolated as a bright-yellow solid. LC/MS: m/z 174.11 (M+H)$^+$, 1.690 min (method 1). $^1$H NMR (500 MHz, chloroform-d) δ ppm $^1$H NMR (500 MHz, chloroform-d) δ ppm 8.69 (s, 1H) 8.14 (d, J=5.19 Hz, 1H) 7.23 (d, J=4.88 Hz, 1H) 7.15 (d, J=13.43 Hz, 1H) 5.21 (d, J=13.73 Hz, 1H) 2.95 (s, 6H)

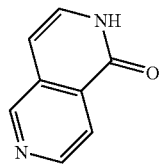

Preparation of 2,6-naphthyridin-1 (2H)-one

To a suspension of (E)-3-(2-(dimethylamino)vinyl)isonicotinonitrile (5 g, 28.9 mmol) in ethanol (50 mL) was added 49 mL of HBr (48% in water) dropwise over 20 minutes. The mixture was heated to reflux overnight for 19 h, and cooled to rt. Upon cooling, fine yellow crystals started to form. The mixture was cooled in the refrigerator for 1.5 h. The crystals were collected by filtration and were washed with ether. To the yellow solid was carefully added sat. aq. NaHCO$_3$ until gas evolution ceased. The off-white solid that formed was collected by filtration and was washed with water to give 1.83 g of the expected product. The mother liquors from both filtrations were combined and were concentrated under reduced pressure. The residue was neutralized with sat. aq. NaHCO$_3$, and the solvent removed under reduced pressure. The residue was diluted with 300 mL of dichloromethane and 300 mL of MeOH, and the mixture was warmed to reflux with a heat gun. The solids were removed by filtration, and the organic solution was concentrated under reduced pressure. The residue was purified by BIOTAGE® flash chromatography using a 0-6.5% MeOH in dichloromethane gradient. The expected product, was isolated as an off-white solid (0.96 g) and the two lots were combined to yield 2,6-naphthyridin-1 (2H)-one (2.79 g, 19.1 mmol, 66% yield). LC/MS: m/z 147.04 (M+H)$^+$, 1.407 min (method 1). $^1$H NMR (500 MHz, DMSO-d$_6$) δ ppm 11.63 (br. s., 1H) 9.07 (s, 1H) 8.62 (d, J=5.49 Hz, 1H) 7.98 (d, J=5.49 Hz, 1H) 7.33 (d, J=7.02 Hz, 1H) 6.67 (d, J=7.02 Hz, 1H).

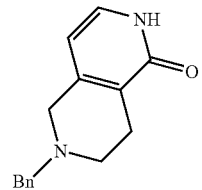

Preparation of 6-benzyl-5,6,7,8-tetrahydro-2,6-naphthyridin-1(2H)-one

To a suspension of 2,6-naphthyridin-1(2H)-one (2.04 g, 13.96 mmol) in acetonitrile (35 mL) was added benzylbromide (1.992 mL, 16.75 mmol). The mixture was heated to reflux. After 2 h the mixture was cooled to rt. The solvent was removed under reduced pressure and the residue was dissolved in EtOH (30 mL) and cooled to 0° C. Sodium borohydride (2.64 g, 69.8 mmol) was added portionwise over 30 min and the mixture was warmed to rt as the ice bath melted. After stirring the reaction mixture overnight at rt, the mixture was carefully acidified to pH=3 with 1N HCl and was stirred for 30 minutes at rt. The solution was concentrated under reduced pressure. The residue was neutralized with sat. aq. NaHCO$_3$ and was extracted with dichloromethane (3×150 mL). The organic solution was concentrated under reduced pressure, and the residue was purified by BIOTAGE® flash chromatography using a 0-10% MeOH in dichloromethane gradient. The fractions containing the expected product were combined and concentrated under reduced pressure to give 6-benzyl-5,6,7,8-tetrahydro-2,6-naphthyridin-1(2H)-one (2.56 g, 10.65 mmol, 76% yield) as a light-yellow solid. LC/MS: m/z 241.08 (M+H)$^+$, 1.362 min (method 1). $^1$H NMR (500 MHz, DMSO-d$_6$) δ ppm 11.29 (br. s., 1H) 7.31-7.37 (m, 4H) 7.24-7.30 (m, 1H) 7.12 (d, J=6.41 Hz, 1H) 5.89 (d, J=6.71 Hz, 1H) 3.63 (s, 2H) 3.32 (br. s., 2H) 2.62 (t, J=5.80 Hz, 2H) 2.40 (t, J=5.04 Hz, 2H).

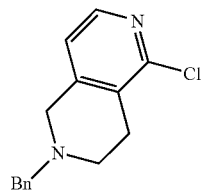

Preparation of 2-benzyl-5-chloro-1,2,3,4-tetrahydro-2,6-naphthyridine

To 6-benzyl-5,6,7,8-tetrahydro-2,6-naphthyridin-1(2H)-one (2.56 g, 10.65 mmol) was added POCl$_3$ (20 mL, 215 mmol). The mixture was heated to 100° C. for 17 h and cooled to rt. The excess POCl$_3$ was removed under reduced pressure, and the residue quenched with sat. NaHCO$_3$ (150 mL) and partitioned with dichloromethane (100 mL) and stirred for 30 minutes. The dichloromethane layer was collected, and the aqueous layer was extracted with dichloromethane (2×100). The combined organic layers were dried with Na$_2$SO$_4$. The drying agent was removed by filtration, and the organic solution was concentrated under reduced pressure. The residue was purified by BIOTAGE® flash chromatography using a 5-30% EtOAc in hexanes gradient. The fractions containing the expected product were combined and concentrated under reduced pressure to give 2-benzyl-5-chloro-1,2,3,4-tetrahydro-2,6-naphthyridine (2.334 g, 9.02 mmol, 85% yield) as a yellow oil. LC/MS: m/z 259.01 (M+H)$^+$, 0.775 min (method 2). $^1$H NMR (500 MHz, chloroform-d) δ ppm 8.10 (d, J=4.88 Hz, 1H) 7.26-7.41 (m, 5H) 6.86 (d, J=4.88 Hz, 1H) 3.69 (s, 2H) 3.58 (s, 2H) 2.84-2.89 (m, 2H) 2.78-2.83 (m, 2H).

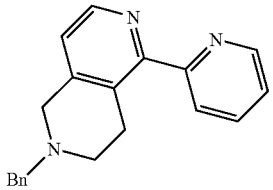

Preparation of 2-benzyl-5-(pyridin-2-yl)-1,2,3,4-tetrahydro-2,6-naphthyridine, 3 TFA To a rb flask containing a solution of 2-benzyl-5-chloro-1,2,3,4-tetrahydro-2,6-naphthyridine (0.2 g, 0.773 mmol) in NMP (3 mL) was added lithium chloride (0.098 g, 2.319 mmol), tri-2-furylphosphine (7.18 mg, 0.031 mmol), and Pd$_2$dba$_3$ (0.014 g, 0.015 mmol). The mixture was flushed with N$_2$ and was stirred for 10 minutes at rt. To the mixture was added 2-(1,1,1-tributylstannyl)pyridine (0.322 mL, 1.005 mmol) and it was heated to 60° C. for 23 h, then warmed to 85° C. and heated for an additional 23 h. The mixture was cooled to rt, filtered through a plug of glass wool and purified by prep HPLC. The expected product, 2-benzyl-5-(pyridin-2-yl)-1,2,3,4-tetrahydro-2,6-naphthyridine, 3 TFA (0.195 g, 0.303 mmol, 39.2% yield), was isolated as a pink oil and was used in the next step with no additional purification. LC/MS: m/z 302.16 (M+H)$^+$, 0.538 min (method 5). $^1$H NMR (500 MHz, chloroform-d) δ ppm 12.51 (br. s., 3H) 8.79 (d, J=4.58 Hz, 1H) 8.60 (d, J=5.19 Hz, 1H) 8.15 (td, J=7.86, 1.68 Hz, 1H) 7.92 (d, J=7.93 Hz, 1H) 7.64 (dd, J=7.17, 5.65 Hz, 1H) 7.42-7.51 (m, 5H) 7.22 (d, J=5.49 Hz, 1H) 4.34-4.47 (m, 4H) 3.51 (br. s., 2H) 3.38 (t, J=6.10 Hz, 2H).

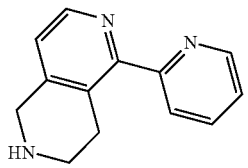

Preparation of 5-(pyridin-2-yl)-1,2,3,4-tetrahydro-2,6-naphthyridine, 3 TFA

To a solution of 2-benzyl-5-(pyridin-2-yl)-1,2,3,4-tetrahydro-2,6-naphthyridine, 3 TFA (0.188 g, 0.292 mmol) in MeOH (5 mL) was added Pd/C (0.062 g, 0.058 mmol). The mixture was flushed with N$_2$, then was purged with H$_2$ and stirred at rt under 1 atm. H$_2$ for 18 h. An additional 0.05 g of Pd/C was added and the mixture was flushed with N$_2$ and purged with H$_2$. After stirring the reaction mixture for an additional 6 h under 1 atm. H$_2$, the mixture was filtered through CELITE® and the solution was concentrated under reduced pressure. The residue was used directly in the next step with no additional purification.

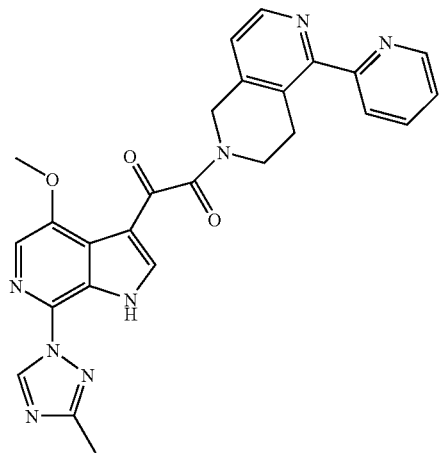

Preparation of 1-(4-methoxy-7-(3-methyl-1H-1,2,4-triazol-1-yl)-1H-pyrrolo[2,3-c]pyridin-3-yl)-2-(5-(pyridin-2-yl)-3,4-dihydro-2,6-naphthyridin-2(1H)-yl)ethane-1,2-dione, 1.4H$_2$O, Compound 26

To a suspension of 2-(4-methoxy-7-(3-methyl-1H-1,2,4-triazol-1-yl)-1H-pyrrolo[2,3-c]pyridin-3-yl)-2-oxoacetic acid (0.062 g, 0.205 mmol), 5-(pyridin-2-yl)-1,2,3,4-tetrahydro-2,6-naphthyridine (0.062 g, 0.205 mmol), and TBTU (0.086 g, 0.267 mmol) in DMF (3 mL) was added Hunig's Base (0.2 mL, 1.145 mmol). The mixture was stirred at rt for 15.75 h and quenched with 5 mL of water and concentrated under reduced pressure. The residue was dissolved in DMF, filtered through a plug of glass wool, and was purified by prep HPLC. The fractions containing the expected product were combined and concentrated. The residue was dissolved in dichloromethane and washed with sat. aq. NaHCO$_3$. The organic layer was dried with MgSO$_4$, was filtered, and was concentrated under reduced pressure to give the expected product as a light pink solid. The compound was further purified using BIOTAGE® flash chromatography with a 0-6% MeOH in dichloromethane gradient. The expected product, 1-(4-methoxy-7-(3-methyl-1H-1,2,4-triazol-1-yl)-1H-pyrrolo[2,3-c]pyridin-3-yl)-2-(5-(pyridin-2-yl)-3,4-dihydro-2,6-naphthyridin-2(1H)-yl)ethane-1,2-dione, 1.4 H$_2$O (0.041 g, 0.077 mmol, 37.7% yield), was isolated as an off-white solid. LC/MS: m/z 495.19 (M+H)$^+$, 0.922 min (method 4). $^1$H NMR (500 MHz, DMSO-d$_6$) δ ppm 11.04 (br. s., 1H) 9.07-9.12 (m, 1H) 8.48-8.71 (m, 2H) 8.20-8.26 (m, 1H) 7.79-7.90 (m, 2H) 7.71-7.74 (m, 1H) 7.27-7.37 (m, 1H) 7.00-7.23 (m, 1H) 4.80-5.00 (m, 2H) 3.75-3.96 (m, 5H) 3.22-3.36 (m, 2H) 2.50-2.61 (m, 3H) 1.57 (s, 3H).

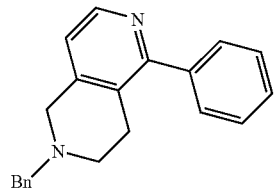

Preparation of 2-benzyl-5-phenyl-1,2,3,4-tetrahydro-2,6-naphthyridine, 2 TFA

To a rb flask containing a solution of 2-benzyl-5-chloro-1,2,3,4-tetrahydro-2,6-naphthyridine (0.49 g, 1.894 mmol) in NMP (9 mL) was added lithium chloride (0.241 g, 5.68 mmol), tri-2-furylphosphine (0.053 g, 0.227 mmol), and Pd₂dba₃ (0.104 g, 0.114 mmol). The mixture was flushed with N₂ and was stirred for 10 minutes at rt. To the mixture was added tributylphenyltin (0.807 mL, 2.462 mmol) and it was heated to 85° C. for 111 h. The mixture was cooled to rt, the solvent removed under reduced pressure, and the residue diluted with sat. aq. NaHCO₃ (40 mL) and extracted with dichloromethane (3×40 mL). The combined organic layers were dried with Na₂SO₄, filtered, and concentrated under reduced pressure. The residue was purified by BIOTAGE® flash chromatography using a 10-50% EtOAc in hexanes gradient. The product was further purified by prep HPLC to give 2-benzyl-5-phenyl-1,2,3,4-tetrahydro-2,6-naphthyridine, 2 TFA (0.48 g, 0.908 mmol, 48.0% yield) as an off-white foam. LC/MS: m/z 301.38 (M+H)⁺, 0.762 min (method 8). ¹H NMR (500 MHz, chloroform-d) δ ppm 9.45 (br. s., 2H) 8.61 (d, J=5.19 Hz, 1H) 7.41-7.54 (m, 10H) 7.29 (d, J=5.49 Hz, 1H) 4.39 (br. s., 2H) 4.32 (s, 2H) 3.34 (br. s., 2H) 3.14 (br. s., 2H).

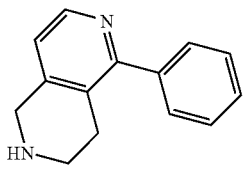

Preparation of 5-phenyl-1,2,3,4-tetrahydro-2,6-naphthyridine, 2 TFA

To a solution of 2-benzyl-5-phenyl-1,2,3,4-tetrahydro-2,6-naphthyridine, 2 TFA (0.48 g, 0.908 mmol) in MeOH (10 mL) was added Pd/C (0.193 g, 0.182 mmol). The mixture was flushed with N₂, then was purged with H₂ and stirred at rt under 1 atm. After stirring the reaction for 3 h it was filtered through a pad of CELITE®. The organic solution was concentrated under reduced pressure to give 5-phenyl-1,2,3,4-tetrahydro-2,6-naphthyridine, 2 TFA (0.398 g, 0.908 mmol, 100% yield) as a light-brown oil which crystallized under vacuum. The residue was used in the next step with no additional purification. LC/MS: m/z 211.00 (M+H)⁺, 0.270 min (method 7). ¹H NMR (500 MHz, MeOD) δ ppm 8.66 (d, 1H) 7.74 (d, J=5.49 Hz, 1H) 7.57-7.67 (m, 5H) 4.69 (s, 2H) 3.54 (t, J=6.10 Hz, 2H) 3.11 (t, J=6.10 Hz, 2H).

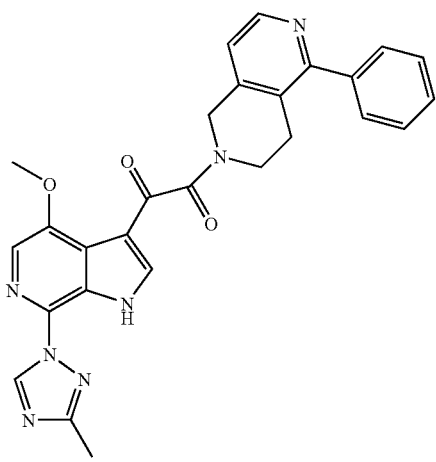

Preparation of 1-(4-methoxy-7-(3-methyl-1H-1,2,4-triazol-1-yl)-1H-pyrrolo[2,3-c]pyridin-3-yl)-2-(5-phenyl-3,4-dihydro-2,6-naphthyridin-2(1H)-yl) ethane-1,2-dione, TFA, Compound 27

To a suspension of 2-(4-methoxy-7-(3-methyl-1H-1,2,4-triazol-1-yl)-1H-pyrrolo[2,3-c]pyridin-3-yl)-2-oxoacetic acid (0.124 g, 0.413 mmol) and 5-phenyl-1,2,3,4-tetrahydro-2,6-naphthyridine, TFA (0.147 g, 0.454 mmol) in DMF (5 mL) was added Hunig's Base (0.5 mL, 2.86 mmol) followed by TBTU (0.172 g, 0.537 mmol). The solution was stirred at rt for 5 h and quenched with 5 mL of water. The solvent was removed under reduced pressure and the residue dissolved in DMF and passed through a plug of glass wool. The DMF solution was purified by prep HPLC. The fractions containing the expected product were combined and concentrated under reduced pressure. The residue was further purified by BIOTAGE® flash chromatography using a 0-5% MeOH in dichloromethane gradient. The expected product, 1-(4-methoxy-7-(3-methyl-1H-1,2,4-triazol-1-yl)-1H-pyrrolo[2,3-c]pyridin-3-yl)-2-(5-phenyl-3,4-dihydro-2,6-naphthyridin-2(1H)-yl)ethane-1,2-dione, TFA (0.192 g, 0.314 mmol, 76% yield), was isolated as an off-white solid. LC/MS: m/z 494.12 (M+H)⁺, 0.878 min (method 6). ¹H NMR (500 MHz, DMSO-d₆) δ ppm 12.40-12.47 (m, 1H) 9.24 (s, 1H) 8.47-8.58 (m, 1H) 8.25-8.32 (m, 1H) 7.87 (s, 1H) 7.30-7.63 (m, 6H) 4.75-4.96 (m, 2H) 3.59-3.88 (m, 5H) 2.78-2.99 (m, 2H) 2.48-2.52 (m, 3H).

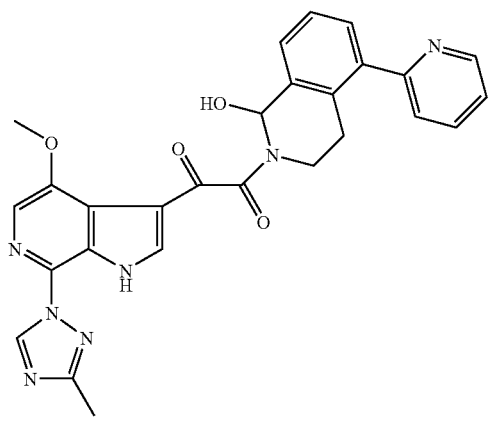

Preparation of 1-(1-hydroxy-5-(pyridin-2-yl)-3,4-dihydroisoquinolin-2(1H)-yl)-2-(4-methoxy-7-(3-methyl-1H-1,2,4-triazol-1-yl)-1H-pyrrolo[2,3-c]pyridin-3-yl)ethane-1,2-dione, Compound 28

A 700 mL mixture of 0.1 M potassium phosphate buffer (pH 7.4), 0.2 mM compound 2, 5 mM NADPH, and 3.6 mg/mL protein of liver S9 fraction of aroclor 1254-induced rats was incubated at 37° C. for 4.5 hours. The incubation mixture was extracted with ethyl acetate (700 mL). The ethyl acetate extract was evaporated to dryness with a rotovapor and the residue was suspended in 1 ml DMSO. The title compound (free base, 23 mg) was isolated from the DMSO suspension with semi-prep HPLC separation using a YMC ODS AQ column (20×150 mm, S5), and 0.1% formic acid in water/0.1% formic acid in acetonitrile as eluents. +ESI MS: [M+H]$^+$ m/z 510--→m/z 464, 256, 209.

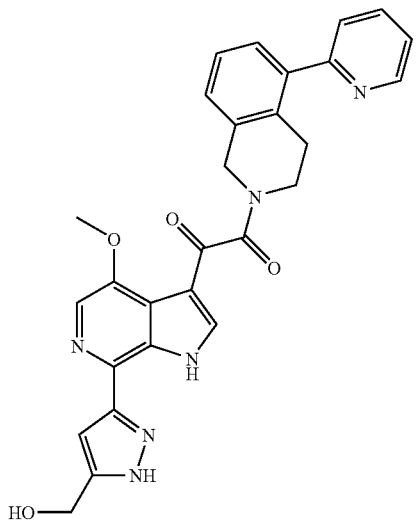

Preparation of 1-(7-(5-(hydroxymethyl)-1H-pyrazol-3-yl)-4-methoxy-1H-pyrrolo[2,3-c]pyridin-3-yl)-2-(5-(pyridin-2-yl)-3,4-dihydroisoquinolin-2(1H)-yl)ethane-1,2-dione, TFA, Compound 29

To a sealable rb flask containing 1-(7-bromo-4-methoxy-1H-pyrrolo[2,3-c]pyridin-3-yl)-2-(5-(pyridin-2-yl)-3,4-dihydroisoquinolin-2(1H)-yl)ethane-1,2-dione (0.1 g, 0.204 mmol) and (3-(tributylstannyl)-1H-pyrazol-5-yl)methanol (0.087 g, 0.224 mmol) in 1,4-dioxane (2 mL) was added tetrakis(triphenylphosphine)palladium(0) (0.047 g, 0.041 mmol). The flask was flushed with N$_2$, sealed, and heated to 110° C. After heating the mixture for 17 h, the mixture was cooled to rt, and concentrated under reduced pressure. The residue was dissolved in DMF and was passed through a plug of glass wool to remove any solids. The DMF solution was purified by prep HPLC. The fractions that contained the expected product were combined and concentrated under reduced pressure. A silica gel column was run using a 0-10% MeOH in dichloromethane gradient for further purification. The expected product, 1-(7-(5-(hydroxymethyl)-1H-pyrazol-3-yl)-4-methoxy-1H-pyrrolo[2,3-c]pyridin-3-yl)-2-(5-(pyridin-2-yl)-3,4-dihydroisoquinolin-2(1H)-yl)ethane-1,2-dione, TFA (19.2 mg, 0.029 mmol, 14.4% yield), was isolated as a light-yellow solid. LC/MS: m/z 509.12 (M+H)$^+$, 1.412 min (method 1). $^1$H NMR (500 MHz, DMSO-d$_6$) δ ppm 13.10 (br. s., 1H) 12.05 (br. s., 1H) 8.60-8.73 (m, 1H) 8.15-8.23 (m, 1H) 8.00-8.04 (m, 1H) 7.83-7.96 (m, 1H) 7.47-7.59 (m, 1H) 7.18-7.44 (m, 4H) 6.80 (br. s., 1H) 5.38 (br. s., 1H) 4.54-4.91 (m, 4H) 3.78-3.84 (m, 3H) 3.54-3.77 (m, 2H) 2.73-3.10 (m, 2H).

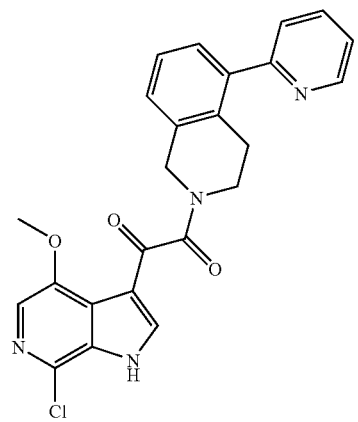

Preparation of 1-(7-chloro-4-methoxy-1H-pyrrolo[2,3-c]pyridin-3-yl)-2-(5-(pyridin-2-yl)-3,4-dihydroisoquinolin-2(1H)-yl)ethane-1,2-dione, Compound 30

A mixture of 1-(7-bromo-4-methoxy-1H-pyrrolo[2,3-c]pyridin-3-yl)-2-(5-(pyridin-2-yl)-3,4-dihydroisoquinolin-2(1H)-yl)ethane-1,2-dione (30 mg, 0.061 mmol), 3-(hydroxymethyl)-1H-1,2,4-triazol-1-ium chloride (18.15 mg, 0.183 mmol) and copper (11.64 mg, 0.183 mmol) in pyridine (1 mL) was heated at 145° C. for 2 hours, LCMS indicated no starting material remained. The reaction mixture was filtered and the clear solution purified by prep. HPLC to give 1-(7-chloro-4-methoxy-1H-pyrrolo[2,3-c]pyridin-3-yl)-2-(5-(pyridin-2-yl)-3,4-dihydroisoquinolin-2(1H)-yl)ethane-1,2-dione as a colorless oil (5.4 mg, 19%). LCMS: m/e 447.02 (M+H)$^+$, 1.52 min (method 9). $^1$H NMR (500 MHz, MeOD) δ ppm 2.80-3.06 (m, 2H) 3.67-3.99 (m, 5H) 4.75-5.08 (m, 2H) 7.32-7.67 (m, 3H) 7.72-7.83 (m, 1H) 7.94-8.18 (m, 2H) 8.32-8.42 (m, 1H) 8.51-8.67 (m, 1H) 8.84-8.95 (m, 1H).

Biology Data for the Examples

"μM" means micromolar;
"mL" means milliliter;
"μl" means microliter;
"mg" means milligram;
The materials and experimental procedures used to obtain the results reported in Tables 1-2 are described below.
Cells:
  Virus production—Human embryonic Kidney cell line, 293T, was propagated in Dulbecco's Modified Eagle Medium (Invitrogen, Carlsbad, Calif.) containing 10% fetal Bovine serum (FBS, Sigma, St. Louis, Mo.).
  Virus infection—Human epithelial cell line, HeLa, expressing the HIV-1 receptor CD4 was propagated in Dulbecco's Modified Eagle Medium (Invitrogen, Carlsbad, Calif.) containing 10% fetal Bovine serum (FBS, Sigma, St. Louis, Mo.) and supplemented with 0.2 mg/mL GENETICIN® (Invitrogen, Carlsbad, Calif.).
  Virus-Single-round infectious reporter virus was produced by co-transfecting human embryonic Kidney 293 cells with an HIV-1 envelope DNA expression vector and a proviral cDNA containing an envelope deletion mutation and the luciferase reporter gene inserted in place of HIV-1 nef sequences (Chen et al, Ref. 41). Transfections were performed using Lipofectamine Plus reagent as described by the manufacturer (Invitrogen, Carlsbad, Calif.).

Experimental Procedure

1. HeLa CD4 cells were plated in 96 well plates at a cell density of $1\times10^4$ cells per well in 100 µl Dulbecco's Modified Eagle Medium containing 10% fetal Bovine serum and incubated overnight.

2. Compound was added in a 2 µl dimethylsulfoxide solution, so that the final assay concentration would be $\leq$10 µM.

3. 100 µl of single-round infectious reporter virus in Dulbecco's Modified Eagle Medium was then added to the plated cells and compound at an approximate multiplicity of infection (MOI) of 0.01, resulting in a final volume of 200 µl per well.

4. Virally-infected cells were incubated at 37 degrees Celsius, in a $CO_2$ incubator, and harvested 72 h after infection.

5. Viral infection was monitored by measuring luciferase expression from viral DNA in the infected cells using a luciferase reporter gene assay kit, as described by the manufacturer (Roche Molecular Biochemicals, Indianapolis, Ind.). Infected cell supernatants were removed and 50 µl of lysis buffer was added per well. After 15 minutes, 50 µl of freshly-reconstituted luciferase assay reagent was added per well. Luciferase activity was then quantified by measuring luminescence using a Wallac MICROBETA® scintillation counter.

6. The percent inhibition for each compound was calculated by quantifying the level of luciferase expression in cells infected in the presence of each compound as a percentage of that observed for cells infected in the absence of compound and subtracting such a determined value from 100.

7. An $EC_{50}$ provides a method for comparing the antiviral potency of the compounds of this disclosure. The effective concentration for fifty percent inhibition ($EC_{50}$) was calculated with the Microsoft Excel Xlfit curve fitting software. For each compound, curves were generated from percent inhibition calculated at 10 different concentrations by using a four parameter logistic model (model 205). The $EC_{50}$ data for the compounds is shown in Table 2. Table 1 is the key for the data in Table 2.

Results

TABLE 1

| Biological Data Key for $EC_{50}$s | |
|---|---|
| Compounds with $EC_{50}$s >0.1 µM | Compounds with $EC_{50}$s <0.1 µM |
| Group "B" | Group "A" |

TABLE 2

| Compound | Structure | HIV_SC10PT (EC50, nM) |
|---|---|---|
| 1 | 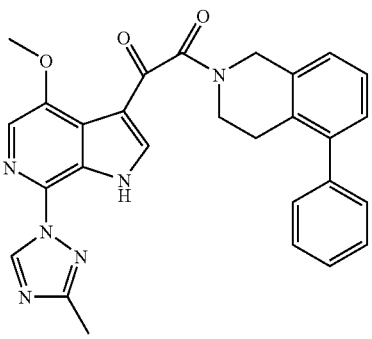 | 0.02 nM |
| 2 | 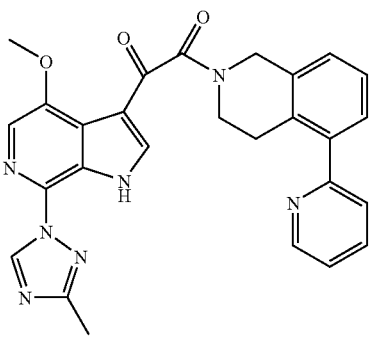 | A |

TABLE 2-continued

| Compound | Structure | HIV_SC10PT (EC50, nM) |
|---|---|---|
| 3 | 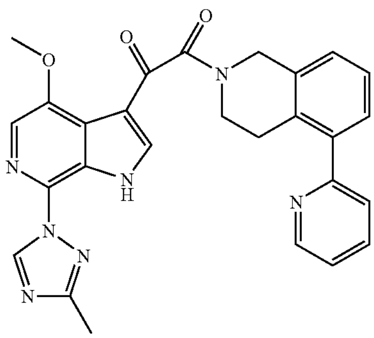 | A |
| 4 | 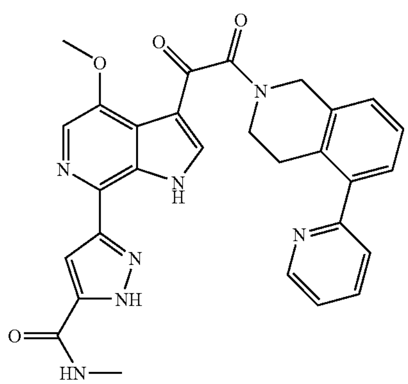 | A |
| 5 | 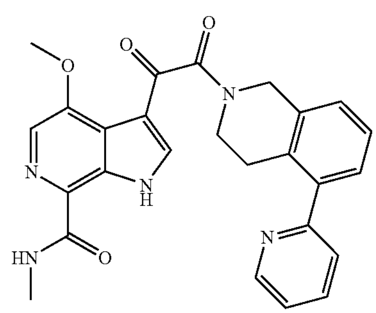 | A |
| 6 | 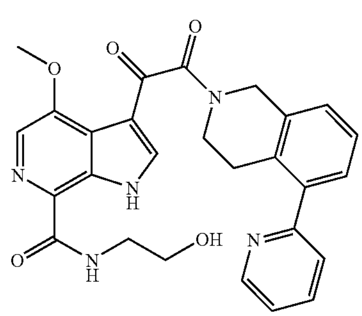 | A |

TABLE 2-continued
| Compound | Structure | HIV_SC10PT (EC50, nM) |
|---|---|---|
| 7 | 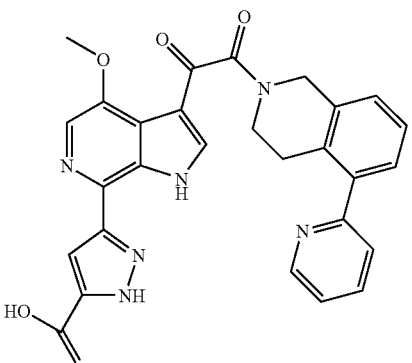 | A |
| 8 | 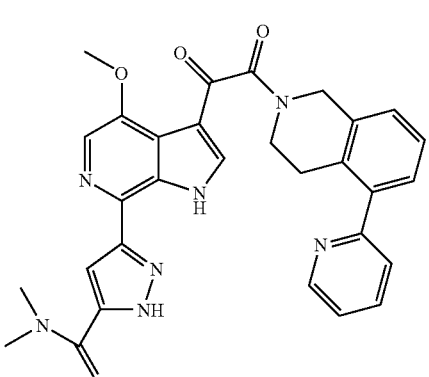 | A |
| 9 | 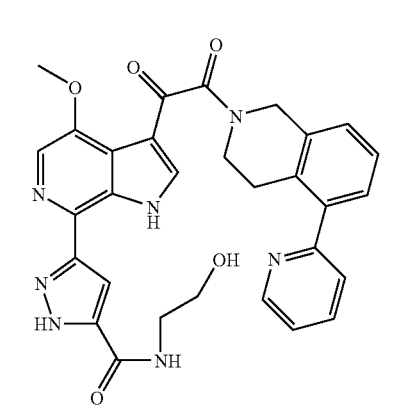 | 0.17 nM |
| 10 | 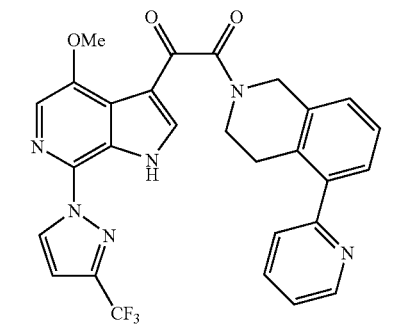 | A |

TABLE 2-continued

| Compound | Structure | HIV_SC10PT (EC50, nM) |
|---|---|---|
| 11 | 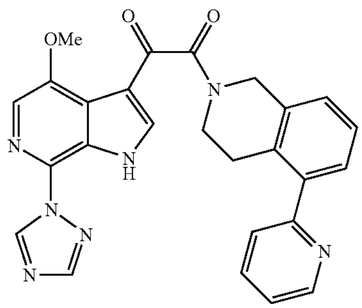 | A |
| 12 | 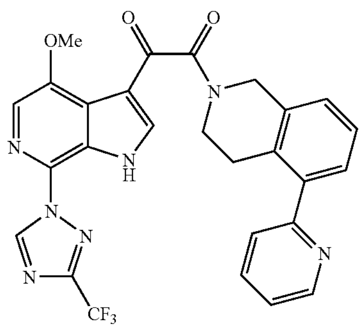 | A |
| 13 | 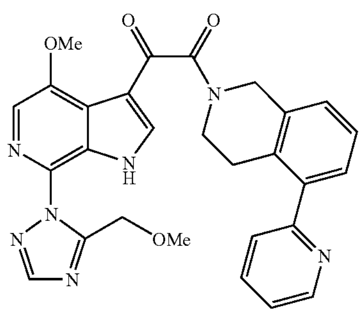 | A |
| 14 | 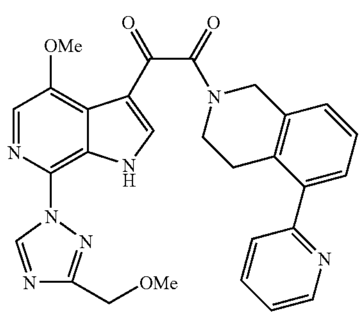 | A |
| 15 | 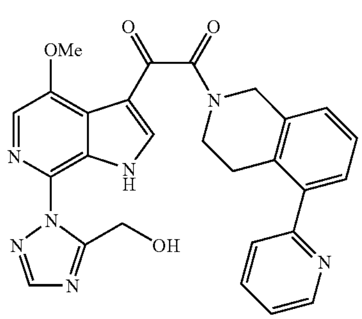 | A |

TABLE 2-continued
| Compound | Structure | HIV_SC10PT (EC50, nM) |
|---|---|---|
| 16 | 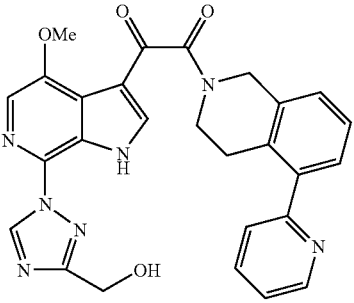 | A |
| 17 | 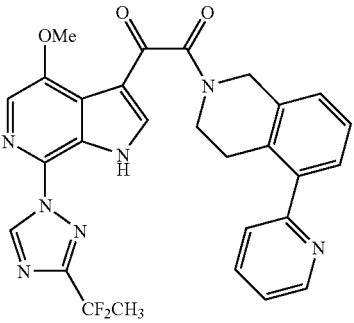 | A |
| 18 | 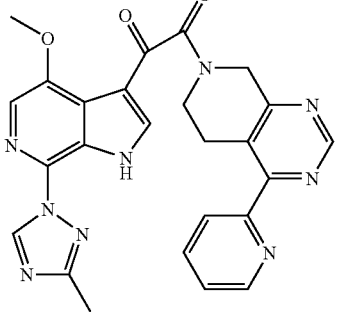 | 0.17 nM |
| 19 | 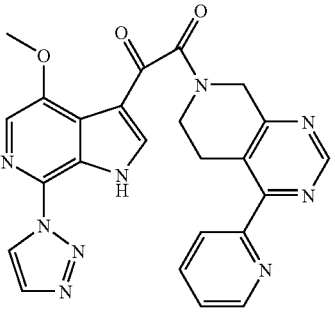 | A |

TABLE 2-continued

| Compound | Structure | HIV_SC10PT (EC50, nM) |
|---|---|---|
| 20 | 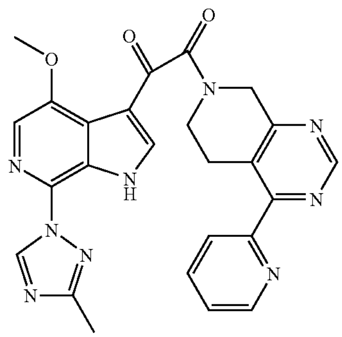 | A |
| 21 | 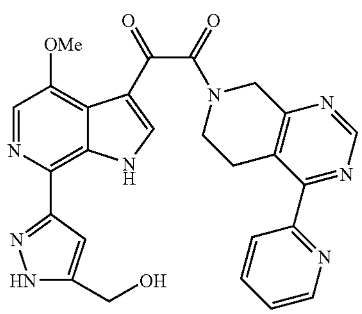 | A |
| 22 | 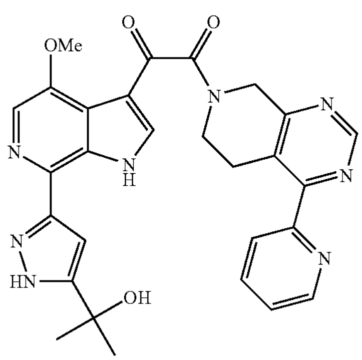 | A |
| 23 | 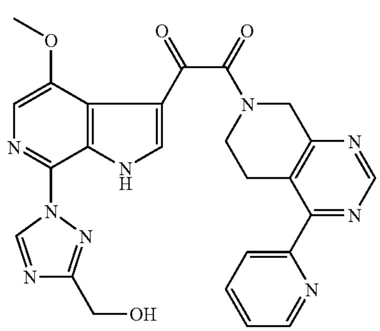 | A |

TABLE 2-continued

| Compound | Structure | HIV_SC10PT (EC50, nM) |
|---|---|---|
| 24 | 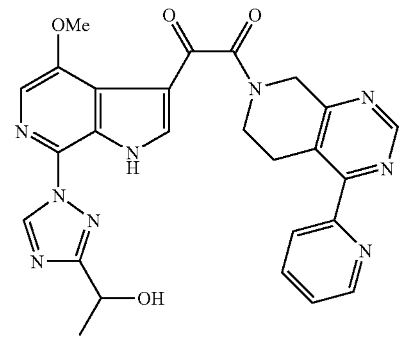 | A |
| 25 | 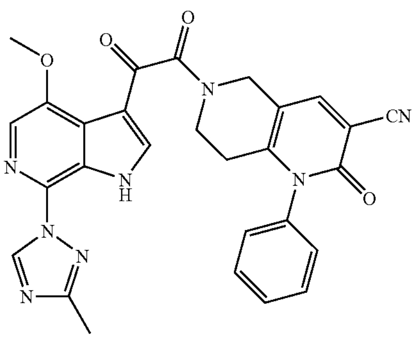 | A |
| 26 | 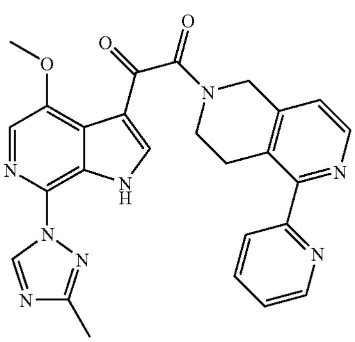 | A |
| 27 | 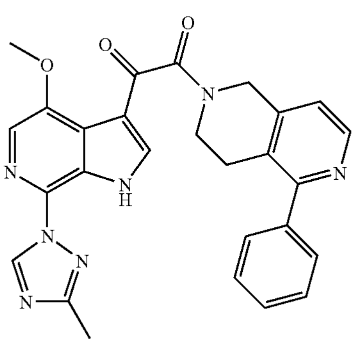 | A |

TABLE 2-continued

| Compound | Structure | HIV_SC10PT (EC50, nM) |
|---|---|---|
| 28 | 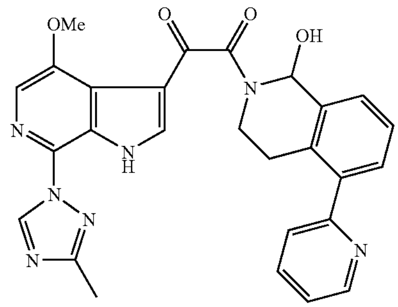 | A |
| 29 | 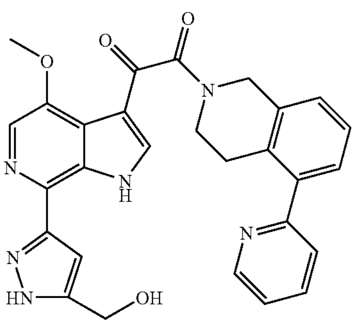 | A |
| 30 | 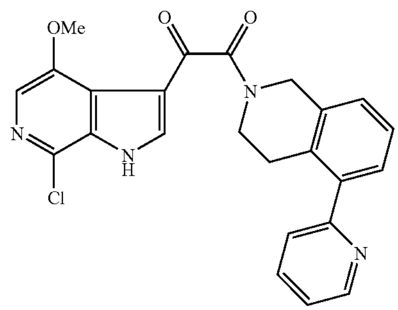 | 171 nM |

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

What is claimed is:

1. A compound of Formula I, including pharmaceutically acceptable salts thereof:

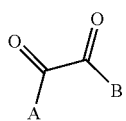

I wherein A is:

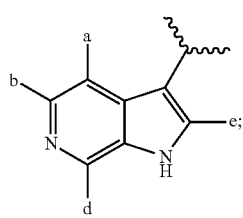

wherein B is selected from the group consisting of:

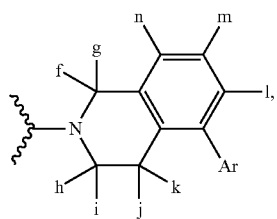

-continued

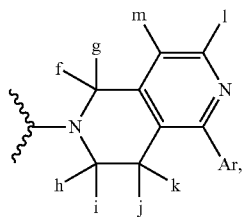

and further wherein
- a is selected from the group consisting of H, halogen and methoxy;
- b and c are selected from the group consisting of H and halogen;
- d is selected from the group consisting of H, halogen, methoxy and Group C;
- e is H;
- f and g are selected from the group consisting of H, ($C_1$-$C_4$) alkyl, and ($C_3$-$C_6$) cycloalkyl group, and wherein said alkyl or cycloalkyl group is optionally substituted with one to three substitutions selected from the group of F, OH, OR, $NR_1R_2$, COOR, and $CONR_1R_2$;
- h and i are selected from the group consisting of H, ($C_1$-$C_4$) alkyl, and ($C_3$-$C_6$) cycloalkyl group, wherein said alkyl or cycloalkyl group is optionally substituted with one to three substitutions selected from the group of F, OH, OR, $NR_1R_2$, COOR, and $CONR_1R_2$;
- j and k are selected from the group consisting of H, F, ($C_1$-$C_4$) alkyl, and ($C_3$-$C_6$) cycloalkyl group, and wherein said alkyl or cycloalkyl group is optionally substituted with one to three substitutions selected from the group of F, OH, OR, $NR_1R_2$, COOR, and $CONR_1R_2$;
- l, m and n are selected from the group consisting of H, OH, CN, ($C_1$-$C_4$) alkyl optionally substituted with one to three substitutions selected from F, OH, OR, $NR_1R_2$, COOR, $CONR_1R_2$, ($C_3$-$C_6$) cycloalkyl optionally substituted with one to three substitutions selected from F, OH, OR, $NR_1R_2$, COOR, $CONR_1R_2$, OR, halogen (attached to carbon only), $NR_1R_2$, COOR, $CONR_1R_2$;
- Ar is selected from the group consisting of phenyl and pyridinyl; wherein said phenyl and pyridinyl are independently optionally substituted with one to three same or different halogens or from one to three same or different substituents selected from Group E;
- Group C is selected from the group consisting of COOR, $CONR_1R_2$, and Group D;
- Group D is selected from the group consisting of pyrazinyl and triazolyl; wherein said pyrazinyl and triazolyl are independently optionally substituted with one to three same or different halogens or from one to three same or different substituents selected from Group E;
- Group E is selected from the group consisting of OH, OR, CN, COOR, $CONR_1R_2$, ($C_1$-$C_4$) alkyl, ($C_3$-$C_6$) cycloalkyl, and wherein said alkyl or cycloalkyl group is optionally substituted with one to three substitutions selected from the group of F, OH, OR, $NR_1R_2$, COOR, and $CONR_1R_2$;
- R, $R_1$ and $R_2$ are independently H, ($C_1$-$C_4$) alkyl, ($C_3$-$C_6$) cycloalkyl group; and wherein $R_1$ and $R_2$ can be connected by carbon, oxygen, nitrogen or sulfur atom to form a ring.

2. The compound of claim 1, wherein B is selected from the group consisting of:

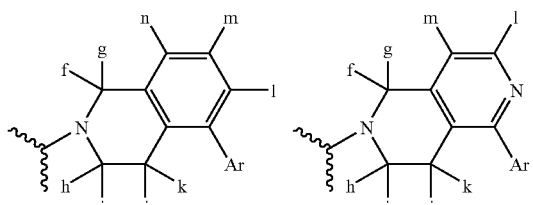

3. The compound of claim 2, wherein B is

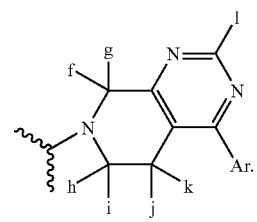

4. The compound of claim 2, wherein B is

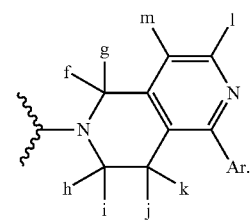

5. The compound of claim 2, wherein B is
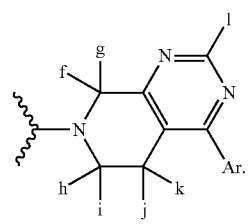
6. A compound which is selected from the group consisting of:
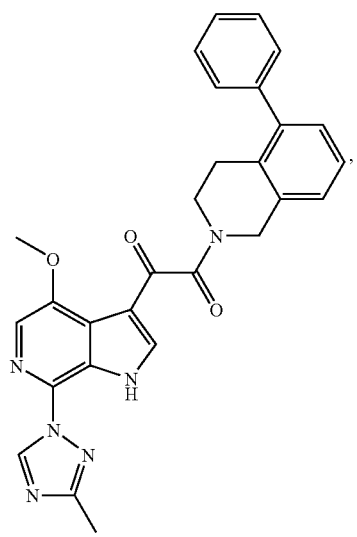
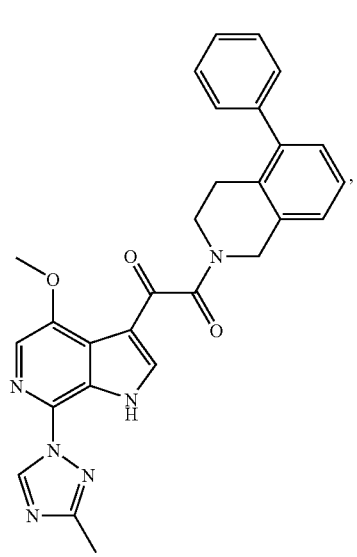
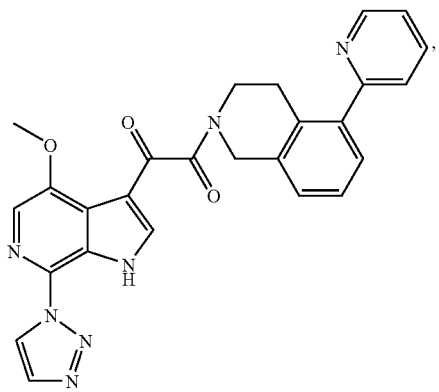
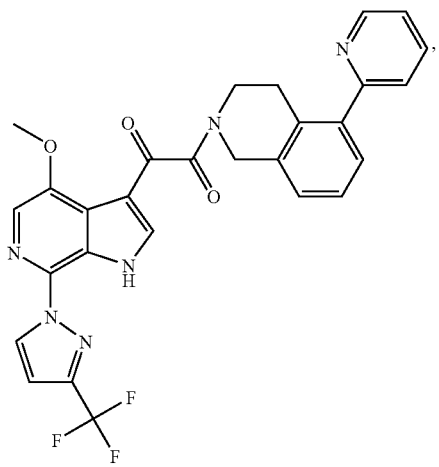
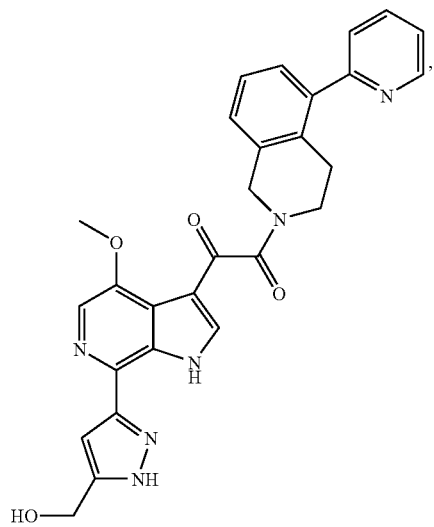

101
-continued
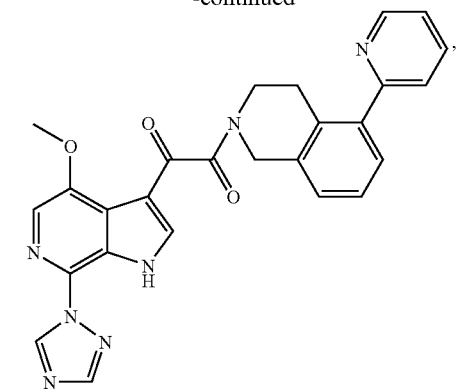
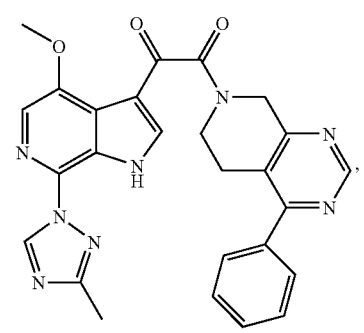
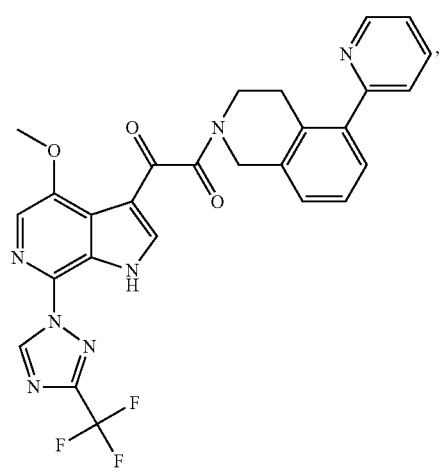
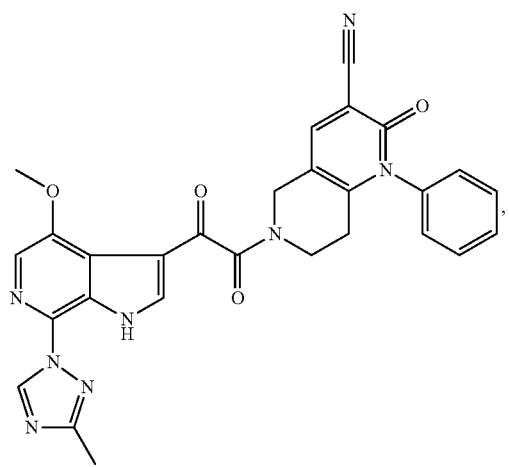
102
-continued
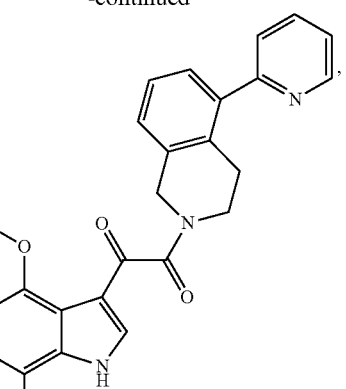
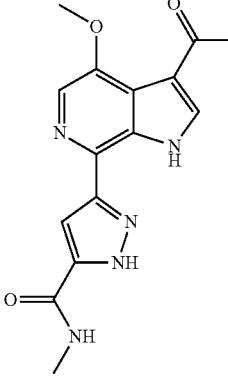
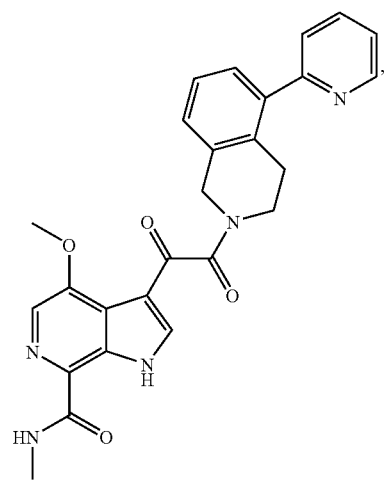
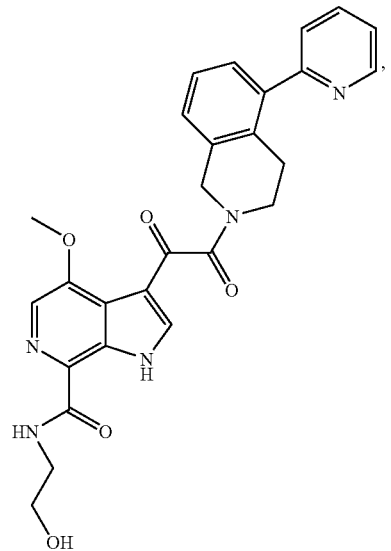

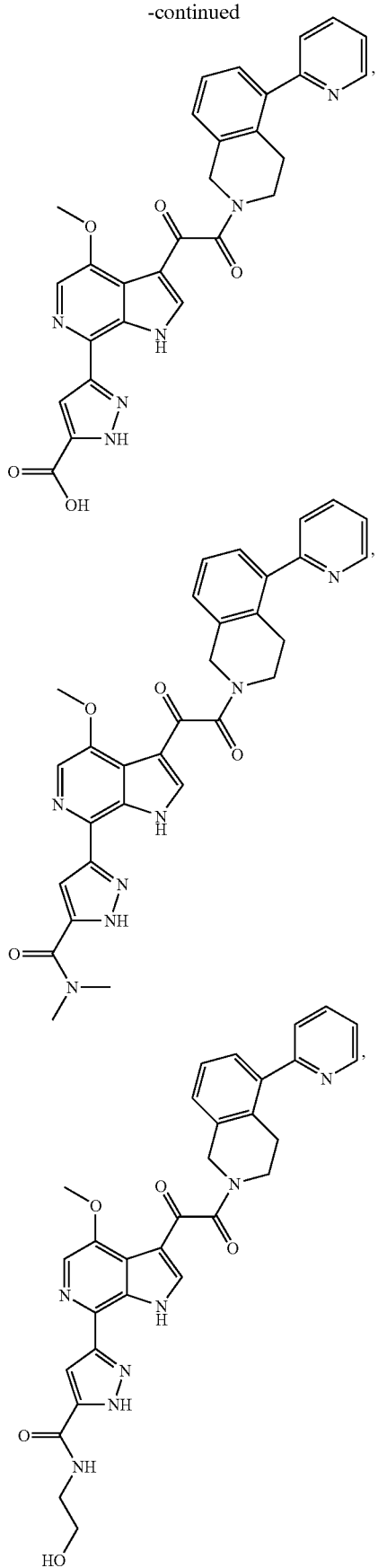
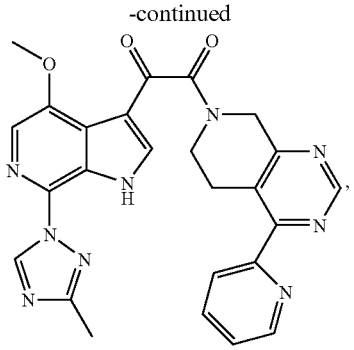
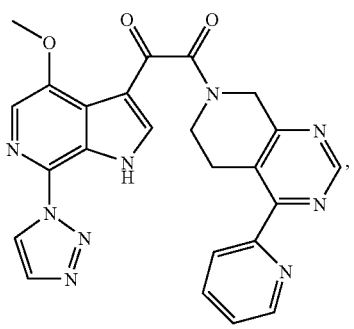
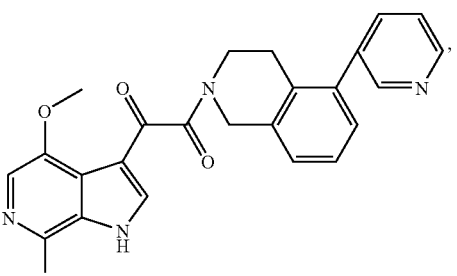
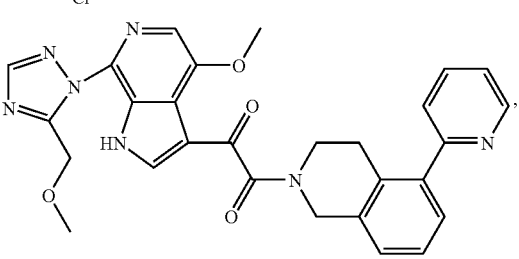
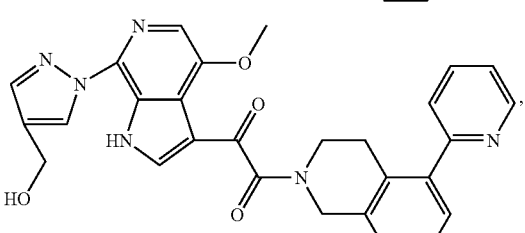
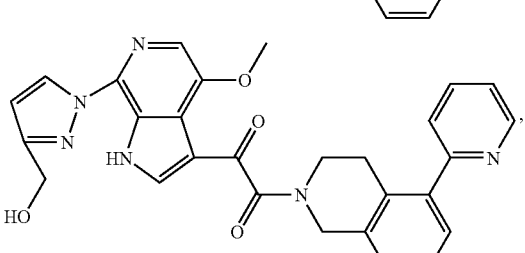

105
-continued

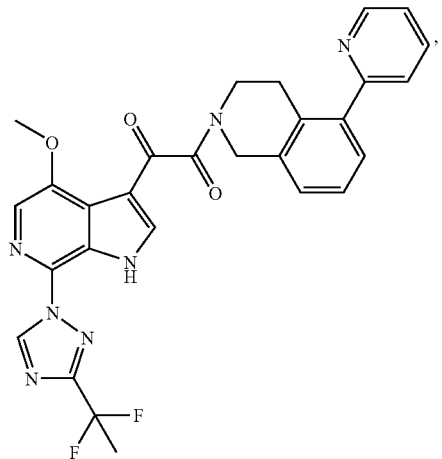

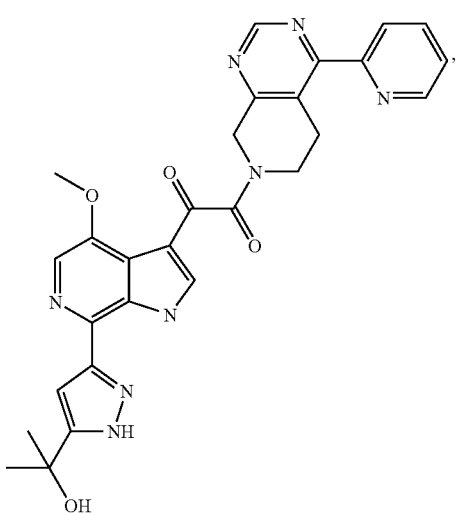

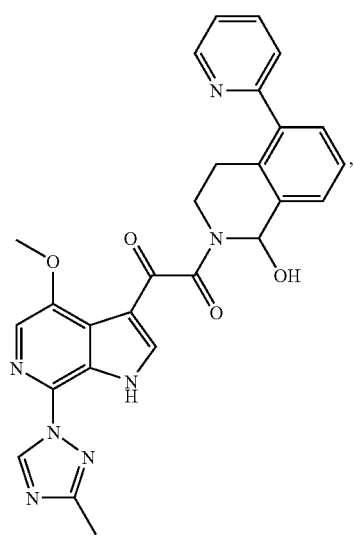

106
-continued

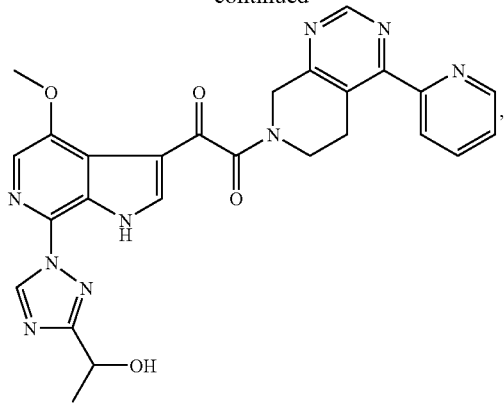

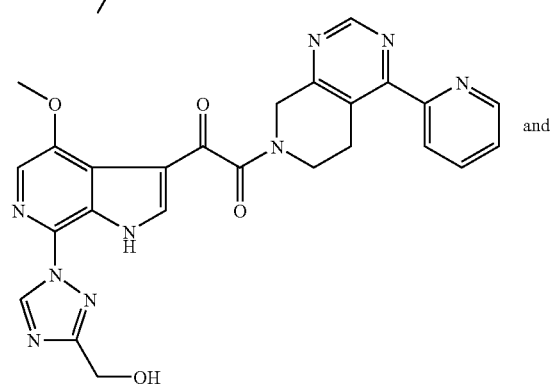

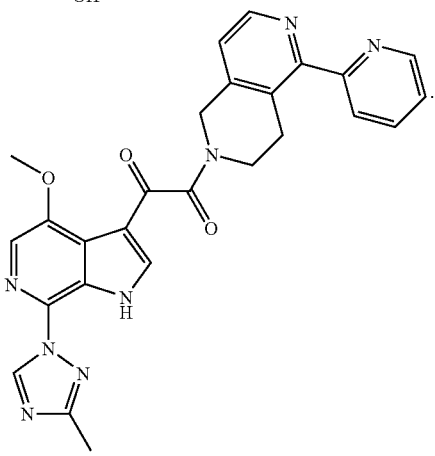

and

7. A pharmaceutical composition which comprises an antiviral effective amount of one or more of the compounds of Formula I as claimed in claim 1, together with one or more pharmaceutically acceptable carriers, excipients or diluents.

8. A pharmaceutical composition which comprises an antiviral effective amount of one or more of the compounds of Formula I as claimed in claim 2, together with one or more pharmaceutically acceptable carriers, excipients or diluents.

9. A pharmaceutical composition which comprises an antiviral effective amount of one or more of the compounds of Formula I as claimed in claim 3, together with one or more pharmaceutically acceptable carriers, excipients or diluents.

10. A pharmaceutical composition which comprises an antiviral effective amount of one or more of the compounds of Formula I as claimed in claim 4, together with one or more pharmaceutically acceptable carriers, excipients or diluents.

11. A pharmaceutical composition which comprises an antiviral effective amount of one or more of the compounds of Formula I as claimed in claim 5, together with one or more pharmaceutically acceptable carriers, excipients or diluents.

12. A pharmaceutical composition which comprises an antiviral effective amount of one or more of the compounds of Formula I as claimed in claim 6, together with one or more pharmaceutically acceptable carriers, excipients or diluents.

13. The pharmaceutical composition of claim 12, useful for treating infection by HIV, which additionally comprises an antiviral effective amount of an AIDS treatment agent selected from the group consisting of:
(a) an AIDS antiviral agent;
(b) an anti-infective agent;
(c) an immunomodulator; and
(d) another HIV entry inhibitor.

14. A method for inhibiting the expression of the HIV virus in a mammal comprising administering to said mammal an antiviral effective amount of a compound of Formula I as claimed in claim 1, and one or more pharmaceutically acceptable carriers, excipients or diluents.

15. The method of claim 14, comprising administering to said mammal an antiviral effective amount of a compound of Formula I, in combination with an antiviral effective amount of an AIDS treatment agent selected from the group consisting of an AIDS antiviral agent; an anti-infective agent; an immunomodulator; and another HIV entry inhibitor.

* * * * *